(12) United States Patent
Owens et al.

(10) Patent No.: US 9,303,092 B2
(45) Date of Patent: *Apr. 5, 2016

(54) METHAMPHETAMINE-LIKE HAPTEN COMPOUNDS, LINKERS, CARRIERS AND COMPOSITIONS AND USES THEREOF

(75) Inventors: Samuel M. Owens, Little Rock, AR (US); Frank Ivy Carroll, Durham, NC (US); Philip Abraham, Cary, NC (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 522 days.

This patent is subject to a terminal disclaimer.

(21) Appl. No.: 13/606,178

(22) Filed: Sep. 7, 2012

(65) Prior Publication Data

US 2013/0296537 A1 Nov. 7, 2013

Related U.S. Application Data

(60) Division of application No. 12/611,708, filed on Nov. 3, 2009, now Pat. No. 8,299,222, which is a division of application No. 11/733,085, filed on Apr. 9, 2007, now Pat. No. 7,632,929, which is a continuation-in-part of application No. 10/255,462, filed on Sep. 26, 2002, now Pat. No. 7,202,348, which is a continuation-in-part of application No. 09/839,549, filed on Apr. 20, 2001, now Pat. No. 6,669,937.

(60) Provisional application No. 60/198,902, filed on Apr. 20, 2000.

(51) Int. Cl.
| | |
|---|---|
| C07K 1/04 | (2006.01) |
| G01N 33/531 | (2006.01) |
| C07K 17/06 | (2006.01) |
| C07K 16/44 | (2006.01) |
| G01N 33/94 | (2006.01) |
| A61K 31/13 | (2006.01) |
| C07C 217/60 | (2006.01) |
| C07C 233/18 | (2006.01) |
| A61K 31/137 | (2006.01) |
| A61K 39/00 | (2006.01) |

(52) U.S. Cl.
CPC ............. C07K 16/44 (2013.01); A61K 31/13 (2013.01); C07C 217/60 (2013.01); C07C 233/18 (2013.01); G01N 33/946 (2013.01); A61K 31/137 (2013.01); A61K 2039/505 (2013.01); C07B 2200/07 (2013.01); C07K 2317/55 (2013.01); Y10S 436/823 (2013.01); Y10S 436/901 (2013.01); Y10T 436/173845 (2015.01)

(58) Field of Classification Search
CPC ..... G01N 33/94; G01N 33/946; C07K 16/44; A61K 2039/505; A61K 39/385; A61K 31/137; Y10S 436/901
See application file for complete search history.

(56) References Cited

U.S. PATENT DOCUMENTS

| | | | |
|---|---|---|---|
| 4,041,076 A | 8/1977 | Avenia et al. | |
| 4,329,281 A | 5/1982 | Christenson et al. | |
| 4,341,758 A | 7/1982 | Sakakibara | |
| 4,517,290 A | 5/1985 | Iwasa et al. | |
| 4,816,567 A | 3/1989 | Cabilly et al. | |
| 5,041,076 A | 8/1991 | Kantor | |
| 5,135,863 A * | 8/1992 | Hu et al. | 435/188 |
| 5,141,850 A | 8/1992 | Cole et al. | |
| 5,160,701 A | 11/1992 | Brown, III et al. | |
| 5,233,025 A * | 8/1993 | Miyazaki et al. | 530/388.9 |
| 5,238,652 A | 8/1993 | Sun et al. | |
| 5,328,828 A * | 7/1994 | Hu et al. | 435/7.9 |
| 5,415,994 A | 5/1995 | Imrich et al. | |
| 5,451,504 A | 9/1995 | Fitzpatrick et al. | |
| 5,492,841 A | 2/1996 | Craig | |
| 5,501,987 A | 3/1996 | Ordonez et al. | |
| 5,545,806 A | 8/1996 | Lonberg et al. | |
| 5,545,807 A | 8/1996 | Surani et al. | |
| 5,559,041 A | 9/1996 | Kang et al. | |
| 5,569,825 A | 10/1996 | Lonberg et al. | |
| 5,620,890 A | 4/1997 | Kamps-Holtzapple | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,690,942 A | 11/1997 | Hjorth | |
| 5,976,812 A | 11/1999 | Huber et al. | |
| 6,054,561 A | 4/2000 | Ring | |
| 6,087,184 A | 7/2000 | Magginetti et al. | |
| 6,306,616 B1 | 10/2001 | Shindelman | |

(Continued)

FOREIGN PATENT DOCUMENTS

| | | |
|---|---|---|
| EP | 0239400 A2 | 9/1987 |
| EP | 0343346 A1 | 11/1989 |

(Continued)

OTHER PUBLICATIONS

Nolli et al. Antibodes against the antibiotics: an overview. Ann. 1st. Super. Sanita., 1991, vol. 27, No. 1, pp. 149-154.*
Aoki et al. Enzyme immunoassay for methamphetamine. J. Pharm. Dyn. 1983, vol. 6, pp. 33-38.*
Kimura, K. et al., "Location of membrane-bound hapten with different length spacers," Immunology, 1990, pp. 323-328, vol. 69.
Office Action dated Oct. 11, 2012 from related U.S. Appl. No. 12/596,765; 10 pages.

(Continued)

*Primary Examiner* — Shafiqul Haq
(74) *Attorney, Agent, or Firm* — Polsinelli PC

(57) ABSTRACT

The invention generally relates to hapten compounds comprising either (+) methamphetamine or (+) amphetamine conjugated to a linker. Generally speaking, hapten compounds of the invention may be used to elicit an immune response to one or more of (+) methamphetamine, (+) amphetamine, or (+) MDMA.

6 Claims, 38 Drawing Sheets
(2 of 38 Drawing Sheet(s) Filed in Color)

(56) References Cited

U.S. PATENT DOCUMENTS

| | | | |
|---|---|---|---|
| 6,358,710 B1 | 3/2002 | Graves et al. | |
| 6,534,325 B1* | 3/2003 | McNally et al. | 436/533 |
| 6,669,937 B2 | 12/2003 | Owens et al. | |
| 7,037,669 B2 | 5/2006 | Zheng et al. | |
| 7,202,348 B2 | 4/2007 | Owens et al. | |
| 7,294,649 B2 | 11/2007 | Hui et al. | |
| 7,371,829 B2 | 5/2008 | McConnell et al. | |
| 7,632,929 B2 | 12/2009 | Owens et al. | |
| 7,674,884 B2 | 3/2010 | Elson et al. | |
| 7,858,756 B2 | 12/2010 | Owens et al. | |
| 8,299,222 B2* | 10/2012 | Owens et al. | 530/403 |
| 8,853,146 B2 | 10/2014 | Owens et al. | |
| 2001/0051158 A1 | 12/2001 | Owens et al. | |
| 2003/0119083 A1 | 6/2003 | Owens et al. | |
| 2003/0171435 A1 | 9/2003 | Pouletty et al. | |
| 2004/0242848 A1 | 12/2004 | Owens et al. | |
| 2007/0207145 A1 | 9/2007 | Owens et al. | |
| 2010/0055126 A1 | 3/2010 | Owens et al. | |
| 2010/0143391 A1 | 6/2010 | Owens et al. | |
| 2014/0271686 A1 | 9/2014 | Owens et al. | |

FOREIGN PATENT DOCUMENTS

| | | |
|---|---|---|
| EP | 0574782 A2 | 12/1993 |
| EP | 0375422 B1 | 7/1996 |
| EP | 1331219 A1 | 7/2003 |
| WO | 86/01533 A1 | 3/1986 |
| WO | 92/03163 A1 | 5/1992 |
| WO | 97/49732 A1 | 12/1997 |
| WO | 01/57182 A2 | 8/2001 |
| WO | 01/81424 A1 | 11/2001 |
| WO | 03/061595 A2 | 7/2003 |
| WO | 2004/050032 A2 | 7/2004 |
| WO | 2005/093417 A1 | 10/2005 |
| WO | 2007/147122 A2 | 12/2007 |
| WO | 2008/131216 A1 | 10/2008 |
| WO | 2010/033913 A1 | 3/2010 |
| WO | 2011/131407 A1 | 10/2011 |

OTHER PUBLICATIONS

International Preliminary Examination Report dated Jul. 29, 2004 from International Patent Application No. PCT/US2003/38384; 3 pages.

International Search Report and Written Opinion dated Mar. 10, 2008 from related International Patent Application No. PCT/US07/071354; 17 pages.

International Search Report dated Oct. 10, 2001 from International Patent Application No. PCT/US01/12899; 4 pages.

International Preliminary Examination Report dated Dec. 10, 2004 from International Patent Application No. PCT/US01/12899; 6 pages.

Interview Summary dated Jan. 31, 2012 from related U.S. Appl. No. 12/611,708, 3 pages.

Notice of Allowance with Examiner-Initiated Interview Summary dated Jun. 4, 2012 from related U.S. Appl. No. 12/611,708, 8 pages.

Office Action dated Nov. 8, 2011 from related U.S. Appl. No. 12/611,708, 15 pages.

Alt, F., et al., Selective Mulitiplication of Dihydrofolate Reductase Genes Methotrexate-resistance Variants of Cultured Murine Cells, J. Biological Chemistry, 1978, p. 1357-1370, vol. 253, No. 5.

Clark, M., Antibody Humanization: a case of the 'Emperor's new clothes'?, Rev. Immunology Today, 2000, pp. 397-402, vol. 21, No. 8.

Colburn, W.A., Specific Antibodies and Fab Fragments to Alter the Pharmacokinetics and Reverse the Pharmacologic/Toxicologic Effects of Drugs, Drug Metabolism Review, 1980, pp. 223-262, vol. 11, No. 2.

Coloma, M., et al., Novel vectors for the expression of anitbody molecules using variable regions generated by polymerasechain reaction, J. Immunological Methods, 1992, pp. 89-104, vol. 152.

Geisse, S., et al., [2] Protein Expression in Mammalian and Insect Cell Systems, Methods in Enzymology, 1999, pp. 19-42, vol. 306.

Giudicelli, V., et al., "IMGT/V-QUEST, an integrated software program for immunoglobulin and T cell receptor V-J and V-D-J rearrangement analysis," Nucleic Acid Res., 2004, pp. W435-W440, vol. 32.

Hardin, et al., A Single Dose of Monoclonal Anti-phencyclidine IgG Offers Long-Term Reductions in Phencyclidine Behavioral Effects in Rats, J Pharmacology and Experimental Therapeutics, 2002, pp. 119-126, vol. 302, No. 1.

International Search Report dated Jul. 2, 2004 from International Patent Application No. PCT/US2003/38384, 1 page.

International Search Report and Written Opinion dated Jul. 22, 2008 from PCT/US2008/060815, 8 pages.

Interview Summary dated Sep. 16, 2009 from related U.S. Appl. No. 11/738,789, 2 pages.

Kipriyanov, S. et al., Generation of recombinant antibodies, Molecular Biotechnology, 1999, p. 173-201, vol. 12, No. 2.

Kunert, R., et al., Stable Recombinant Expression of the Anti HIV-1 Monoclonal Antibody 2F5 After IgG3/IgG1 Subclass Switch in CHO Cells, Biotech and Bioeng, 2000, pp. 97-103, vol. 67, No. 1.

Kuus-Reichel, et al., Will Immunogenicity Limit the Use, Efficacy, and Future Development of Therapeutic Monoclonal Antibodies?, Clinical and Diagnostic Lab Immun., 1994, pp. 365-372, vol. 1, No. 4.

Lacy, et al., Engineering and Characterization of a Mouse/Human Chimeric Anti-Phencyclidine Monoclonal Antibody, Int Immuno, 2008, pp. 1-11, vol. 8.

Laurenzana, et al., Treatment of Adverse Effects of Excessive Phencyclidine Exposure in Rates with a Minimal Dose of Monoclonal Antibody, J Pharmacology and Exp. Therap., 2003, pp. 1092-1098, vol. 306, No. 3.

Lim, et al., Crystal Structure of Monoclonal 6B5 Fab Complexed with Phencyclidine, J Biol Chem, 1998, pp. 28576-28582, vol. 273, No. 44.

McClurkan, M., et al., Disposition of a Monoclonal Anti-phencyclidine Fab Fragment of Immunoglobulin G in Rats, J. Pharmacology and Exp. Therap., 1993, p. 1439-45, vol. 266, No. 3.

Notice of Allowance dated Aug. 19, 2010 from U.S. Appl. No. 11/763,948, 7 pages.

Notice of Allowance dated Aug. 3, 2009 from related U.S. Appl. No. 11/733,085, 7 pages.

Notice of Allowance mailed Jul. 11, 2003 from U.S. Appl. No. 09/839,549, 6 pages.

Office Action dated Nov. 26, 2001 from related U.S. Appl. No. 09/839,549, 12 pages.

Office Action dated Nov. 16, 2005 from related U.S. Appl. No. 10/255,462, 8 pages.

Office Action dated Feb. 22, 2006 from related U.S. Appl. No. 10/828,782, 8 pages.

Office Action dated Oct. 24, 2006 from related U.S. Appl. No. 10/828,782, 8 pages.

Office Action dated Feb. 13, 2007 from related U.S. Appl. No. 10/828,782, 5 pages.

Office Action dated May 12, 2008 from related U.S. Appl. No. 11/738,789, 12 pages.

Office Action dated Dec. 15, 2008 from related U.S. Appl. No. 11/738,789, 12 pages.

Office Action dated May 21, 2009 from related U.S. Appl. No. 11/736,789, 8 pages.

Office Action dated Sep. 25, 2009 from related U.S. Appl. No. 11/763,948, 11 pages.

Office Action dated Dec. 3, 2009 from related U.S. Appl. No. 11/738,789, 7 pages.

Office Action dated Mar. 24, 2010 from related U.S. Appl. No. 11/763,948, 10 pages.

Office Action dated Oct. 26, 2011 from related European Patent Application No. 07798645.3, 4 pages.

Owens, et al., Anti-Phencyclidine Fab as a Tool for Studying the Toxic Effects Phencyclidine, NIH Immunotoxicology Workshop, Oct. 17 and 18, 1983, Session B—Poster 27.

Owens, et al., New Generation of Medications for Drug Abuse, Pharmaceutical News, 1998, pp. 44-58, vol. 5, No. 6.

(56) References Cited

OTHER PUBLICATIONS

Owens, et al., Phencyclidine-Specific Fab Fragments Alter Phencyclidine Disposition in Dogs, Drug Metablolism and Disposition, 1986, pp. 52-58, vol. 14, No. 1.

Peakman, et al., Comparison of expression of a humanized monoclonal antibody in mouse NSO myeloma cells and Chinese Hamster Ovary cells, Hum. Antibod. Hybridomas, 1994, pp. 65-74, vol. 5, No. 1 and 2.

Proksch et al. The Effect of Rate of Drug Administration on the Extend and Time Course of Phencyclidine Distribution in Rat Brain, Testis, and Serum, DMD, 2000, p. 742-747, vol. 28, No. 7.

Proksch, et al., "Pharmacokinetic Mechanisms for Obtaining High Renal Coelimination of Phencyclidine and a Monoclonal Antiphencyclidine Antigen-Binding Fragment of Immunoglobulin G in the Rat1," JPET, 1998, pp. 616-624, vol. 287, No. 2.

Reichert, et al., Monoclonal antibodies in the clinic, Nature Biotechnology, 2001, pp. 819-822, vol. 19.

Simmons, L., et al., "Expression of full-length immunoglobulins in Escherichia coli: rapid and efficient production of aglycosylated antibodies," Journal of Immunol. Methods, 2002, pp. 133-147, vol. 263.

Sinacore, et al., Adaptation of Mammalian Cells to Growth in Serum-Free Media, Molecular Biotechnology, 2000, pp. 249-257, vol. 15.

Smith, TW. et al., Immunogenicity and kinetics of distribution and elimination of sheep digoxin-specific IgG and Fab fragments in the rabbit and baboon, Clin. Exp. Immunol., 1979, pp. 384-396, vol. 36.

Smith, TW. et al., Treatment of Life-Threatening Digitalis Intoxication With Digoxin-Specific Fab Antibody Fragments, The New England Journal of Medicine, 1982, pp. 1357-1362. vol. 307, No. 22.

Spectors, S., Antibodies as Pharmacological Agents, Biochemical Pharmacology, 1976, pp. 2427-2428, vol. 25.

Extended European Search Report mailed Jun. 14, 2010 from related European Patent Application No. 07798645.3, 7 pages.

Supplementary European Search Report mailed Nov. 3, 2010 from related European Patent Application No. 08746264.4, 8 pages.

Whitelegg, N. et al., "WAM: an improved algorithm for modeling antibodies on the WEB," Protein Engineering, 2000, pp. 819-824, vol. 13, No. 12.

Albertson et al, "Methamphetamine and the Expanding Complications of Amphetamines", West J. Med, 1999, pp. 214-219 vol. 170, No. 4.

Aoki et al, "Immunoassay for Methamphetamine With a New Antibody", Forensic Science International, 1990, pp. 245-255, vol. 44.

Byrnes-Blake et al, "Generation of anti-(+)methamphetamine antibodies is not impeded by (+) methamphetamine administration during active immunization of rats", International Immunopharmacology, 2001, pp. 329-338, vol. 1.

Byrnes-Blake et al, "Pharmacodynamic mechanisms of monoclonal antibody-based antagonism of (+)-methamphetamine in rats", European Journal of Pharmacology, 2003, pp. 119-128, vol. 461.

Byrnes-Blake et al, "Monoclonal IgG affinity and treatment time alters antagonism of (+)-methamphetamine effects in rats", European Journal of Pharmacology, 2005, pp. 86-94, vol. 521.

Chio et al, "Localization of the epitope in methamphetamine and its antibody use for the detection of methamphetamine and benzphetamine by polarization fluoroimmunoassay", Journal of Immunoassay, 1995, pp. 263-278, vol. 16(3).

Cody et al, "Detection of D,L-Amphetamine. D.L-Methamphetamine, and Illicit Amphetamine Analogs Using Diagnostic Products Corporation's Amphetamine and Methamphetamine Radioimmunoassay", Journal of Analytical Toxicology, 1990, pp. 321-324, vol. 14(5).

Colbert et al, "Single-Reagent Polarization Fluoroimmunoassay for Amphetamine in Urine" Clinical Chemistry, 1985, pp. 1193-1195, vol. 31, No. 7.

Cook et al, "Pharmacokinetic of methamphetamine self-administered to human subjects by smoking S-(+)-methamphetamine hydrochloride", Drug Metabolism and Dispositions, 1993, pp. 717-723, vol. 21, No. 4.

Danger et al, "Development of murine monoclonal antibodies to methamphetamine and methamphetamine analogues", Journal of Immunological Methods, 2006, pp. 1-10, vol. 309.

Faraj et al, "Specificity of an Antibody Directed against d-Methamphetamine. Studies with Rigid and Nonrigid Analogs", Journal of Medicinal Chemistry, 1976, pp. 20-25. vol. 19(1).

Farre et al, "Repeated doses administration of MDMA in humans: pharmacological effects and pharmacokinetics", Phsychopharmacology, 2004, pp. 364-375, vol. 173.

Hardin et al, "Pharmacodynamics of a Monoclonal Antiphencyclidine Fab with Broad Selectivity for Phencyclidine-Like Drugs", The Journal of Pharmacology and Experimental Therapeutics, 1998, pp. 1113-1122, vol. 285(3).

Kosten et al, "Immunotherapy for the treatment of drug abuse", Pharmacology and Therapeutics, 2005, pp. 76-85 vol. 108.

Laurenzana et al, "Use of Anti-(+)-Methamphetamine Monoclonal Antibody to Significantly Alter (+)-Methamphetamine and (+)-Amphetamine Disposition in Rats", Drug Metabolism and Disposition, 2003, pp. 1320-1326, vol. 31(11).

Li et al, "Four-choice drug discrimination in pigeons", Behavioural Pharmacology, 2001, pp. 621-628, vol. 12.

McMillan et al, "Schedule control of quantal and graded dosed effect curves in a drug-drug-saline discrimination", Pharmacology, Biochemistry and Behavior, 2001, pp. 395-402, vol. 68.

McMillian et al, "Discrimination of pentobarbital doses and drug mixtures under fixed-ratio and fixed-interval reinforcement schedules", Behavioural Pharmacology, 2001, pp. 195-208, vol. 12.

McMillian et al, "Pharmacokinetic antagonism of (+)-methamphetamine discrimination by low-affinity monoclonal antimethamphetamine antibody". Behavioural Pharmacology, 2002. pp. 466-473, vol. 13.

McMillian et al, "Effects of Murine-Derived Anti-Methamphetamine Monoclonal Antibodies on (+)-Methamphetamine Self-Administration in the Rat", Journal of Pharmacology and Experimental Therapeutics, 2004, pp. 1248-1255, vol. 309(3).

Nam et al, "Production and Characterization of Monoclonal Antibody That Simultaneously Recognizes Methamphetamine and Its Major Metabolite", Biological and Pharmaceutical Bulletin, 1993 pp. 490-492, vol. 16(5).

Owens et al, "Antibodies Against Arylcyclohexylamines and Their Similarities in Binding Specificity with the Phencyclidine Receptor", The Journal of Pharmacology and Experimental Therapeutics, 1998, pp. 472-478 vol. 246(2).

Peterson et al, "Using Hapten Design to Discover Therapeutic Monoclonal Antibodies for Treating Methamphetamine Abuse", Journal of Pharmacology and Experimental Therapeutics, 2007 pp. 30-39, vol. 322(1).

Peterson et al., "Monoclonal Antibody Form and Function. Manufacturing the Right Antibodies for Treating Drug Abuse", The AAPS Journal, 2006, pp. E383-E390, vol. 8(2).

Proksch et al. "Anti-Phencyclidine Monoclonal Antibodies Provide Long-Term Reductions in Brain Phencyclidine Concentrations during Chronic Phencyclidine Administration in Rats", The Journal of Pharmacology and Experimental Therapeutics, 2000, pp. 831-837, vol. 292(3).

Richards et al., "Methamphetamine Abuse and Emergency Department Utilization". West J Med, 1999, pp. 198-202, vol. 170, No. 4.

Riviere et al. "Spontaneous Locomotor Activity and Pharmacokinetics of Intravenous Methamhetamine and Its Metabolite Amphetamine in the Rat", The Journal of Pharmacology and Experimental Therapeatics. 1999. pp. 1220-1226, vol. 291(3).

Riviere et al. "Disposition of Methamphetamine and Its Metabolite Amphetamine in Brain and Other Tissues in Rats after Intravenous Administration", The Journal of Pharmacology and Experimental Therapeutics, 2000, pp. 1042-1047, vol. 292, No. 3.

Suttijitpaisal et al., "Immunoassays of Amphetamines: Immunogen Structure vs Antibody Specificity", Asian Pacific Journal of Allergy and Immunology, 1992, pp. 159-164, vol. 10.

Tempest et al. "Reshaping a Human Monoclonal Antibody to Inhibit Human Respiratory Syncytial Virus Infection in VIVO", Biotechnology, 1991, pp. 266-271, vol. 9.

(56) References Cited

OTHER PUBLICATIONS

Terazawa et al., "Development of Monoclonal Antibodies Reactive With Methamphetamine Raised Against a New Antigen", Journal of Immunoassay, 1991, pp. 277-292, vol. 12(2).
Tokura et al., "Inducation of Methamphetamine-Specific Antibody Using Biodegradable Carboxymethy-chitin", Analytical Biochemistry, 1987, pp. 117-122, vol. 161.
Usagawa et al. "Preparation of monoclonal antibodies against methamphetamine" Journal of Immunology Methods, 1989, pp. 111-115, vol. 119.
Ward et al. "Radioimmunoassy for the Dual Detection of Amphetamine and Methamphetamine" Journal of Forensic Science, 1994, pp. 1486-1496, vol. 39(6).
Daniels et al, "Effects of anti-phencyclidine and anti-(+)-methamphetamine monoclonal antibodies alone and in combination on the discrimination of phencyclidine and (+)-methamphetamine by pigeons", Psychopharmacology, 2006, pp. 36-44, vol. 185.
Gentry et al, "Safety and efficiency of an anti-(+)-methamphetamine monoclonal antibody in the protection against cardiovascular and central nervous system effects of (+)-methamphetamine in rats", International Immunopharmacology, 2006, pp. 968-977. vol. 6.
Niwaguchi et al, "Determination of d-Methamphetamine in Urine After Administration of d-or dl-Methamphetamine to Rats by Radioimmunoassay Using Optically Sensitive Antiserum", Journal of Forensic Sciences, 1982, pp. 592-597, vol. 27, No. 3.
Pitas et al, "Anti-Phencyclidine Monoclonal Antibody Binding Capacity is not the Only Determinant of Effectiveness, Disproving the Concept that Antibody Capacity is Easily Surmounted", American Society for Pharmacology and Experimental Therapeutics, 2006, pp. 906-912, vol. 34, No. 6.
Valentine et al, "Anti-phencyclidine Monoclonal Fab Fragments Markedly Alter Phencyclidine Pharmacokinetics in Rats", Journal of Pharmacology and Experimental Therapeutics, 1994, pp. 1079-1085, vol. 269(3).
Cho, et al., Relevance of Pharmacokinetic Parameters in Animal Models of Methamphetamine Abuse, 2001, pp. 161-166, Synapse, vol. 39.
Sato, et al., Relapse of Paranoid Psycotic State in Methamphetamine Model of Schizophrenia, 1992, pp. 115-122, Schizophrenia Bulletin, vol. 18. No. 1.
Valentine, et al., Antiphencyclidine Monoclonal Antibody Therapy Significantly Changes Phencyclidine Concentrations in Brain and Other Tissues and Rats, 1996, pp. 717-724, JPET, vol. 278, No. 2.
Valentine, et al., Antiphencyclidine Monoclonal Fab Fragments Reverse Phencyclidine-Induced Behavioral Effects and Ataxia in Rats, 1996, pp. 709-716, JPET, vol. 278, No. 2.
International Search Report dated Oct. 10, 2001.
International Search Report dated Mar. 10, 2008.
Office action dated Jun. 14, 2005 from related U.S. Appl. No. 10/255,462, 10 pgs.
Office action dated Jul. 31, 2006 from related U.S. Appl. No. 10/255,462, 4 pgs.
Office action dated Jun. 11, 2008 from related U.S. Appl. No. 11/733,085, 15 pgs.
Office action dated Dec. 15, 2008 from related U.S. Appl. No. 11/733,085, 16 pgs.
Bendig, "Humanization of Rodent Monoclonal Antibodies by CDR Grafting", Methods: A Companion to Methods in Enzymology, 1995, pp. 83-93, vol. 8.
Colman, "Effects of amino acid sequence changes on antibody-antigen interactions", Research in Immunology, Biomolecular Research Institute, 1994, pp. 33-35, vol. 145.
International Search Report and Written Opinion from related International Application No. PCT/US14/25890, dated Oct. 6, 2014; 9 pgs.
MacCallum et al., "Antibody-antigen Interactions: Contact Analysis and Binding Site Topography", J. Mol. Biol., 1996, pp. 732-745, vol. 262.
Notice of Allowance from related U.S. Appl. No. 13/802,688, dated Oct. 29, 2014; 7 pgs.
Notice of Allowance from related U.S. Appl. No. 13/802,688, dated Jul. 24, 2014; 10 pgs.
Notice of Allowance from related U.S. Appl. No. 12/596,765, dated Jun. 4, 2014; 14 pgs.
Office Action from related U.S. Appl. No. 13/802,688, dated May 8, 2014; 30 pgs.
Office Action from related U.S. Appl. No. 13/802,688, dated Jan. 3, 2014; 29 pgs.
Office Action from related European Patent Application No. 08746264.4, dated Nov. 5, 2014; 6 pgs.
Office Action from related European Patent Application No. 08746264.4, dated Aug. 20, 2013; 5 pgs.
Office Action from related U.S. Appl. No. 12/596,765, dated Jan. 22, 2014; 11 pgs.
Office Action from related U.S. Appl. No. 12/596,765, dated Mar. 25, 2013; 10 pgs.
Owens et al., "Mus musculus mAb3F2 immunoglobulin kappa light chain mRNA, partial cds", GenBank Accession No. DQ381545.1, dated Feb. 1, 2007; 2 pgs.
Paul, "Fundamental Immunology", Third Edition, 1993, Raven Press, New York, Chapter 9, pp. 292-295.
Rudikoff et al., "Single amino acid substitution altering antigen-binding specificity", Proc. Natl. Acad. Sci. USA, 1982, pp. 1979-1983, vol. 79.
Schmitt et al., "Synthesis of anorexigenic compounds from Pervitin", Chim. Ther., 1967, pp. 260-267, vol. 2, No. 4, English Abstract only; 2 pgs.
Wang et al., "Mus musculus anti-PRSV coat protein monoclonal antibody PRSV-H 10-9 immunoglobulin heavy chain variable region mRNA, complete cds", GenBank Accession No. AY571285.1, dated Jul. 21, 2004; 2 pgs.
Wu et al., "Humanization of a Murine Monoclonal Antibody by Simultaneous Optimization of Framework and CDR Residues", J. Mol. Biol., 1999, pp. 151-162, vol. 294.

* cited by examiner

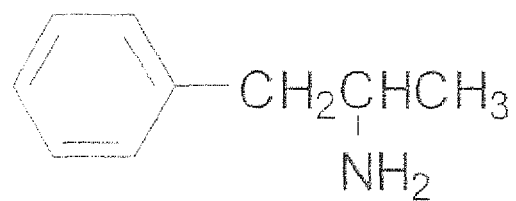
*d*-Amphetamine
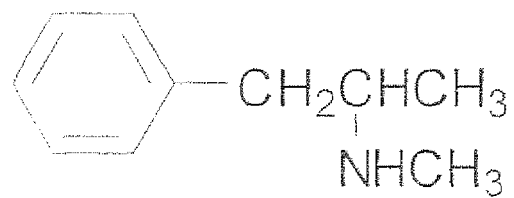
(+)Methamphetamine
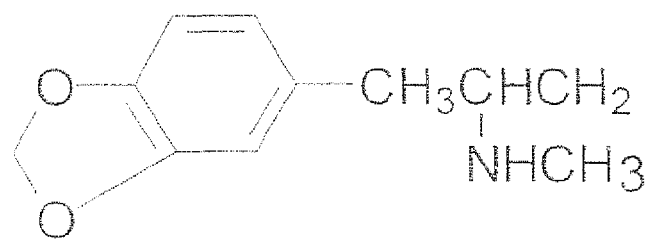
MDMA
Fig. 3

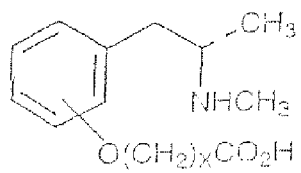
10
X = 2 to 9
connection at 2,
3, or 4 position
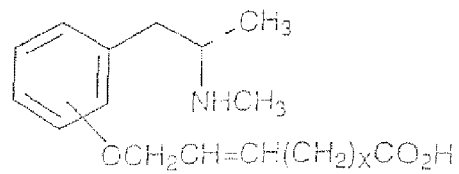
11
X = 1 to 6
connection at 2,
3, or 4 position
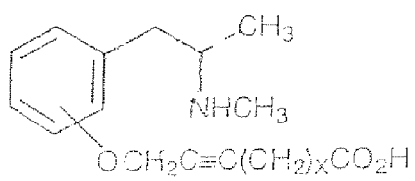
12
X = 1 to 6
connection at 2,
3, or 4 position
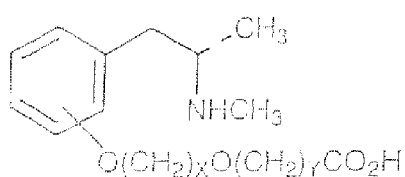
13
X = 2 to 4
Y = 1 to 5
connection at 2,
3, or 4 position
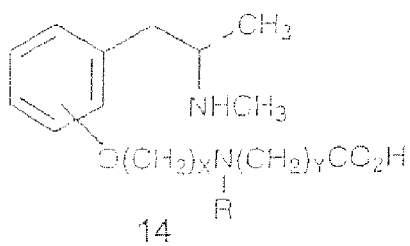
14
X = 2, 3
connection at 2,
3, or 4 position
R = alkyl 1-5 carbon
Fig. 4A

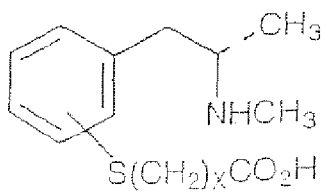
15
X = 2 to 9
connection at 2,
3, or 4 position
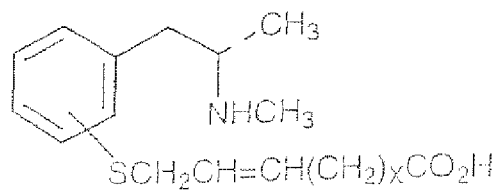
16
X = 1 to 6
connection at 2,
3, or 4 position
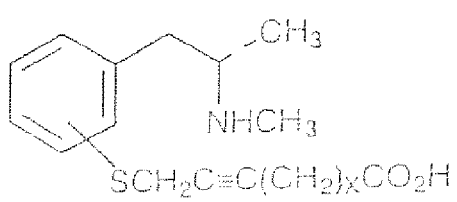
17
X = 1 to 6
connection at 2,
3, or 4 position
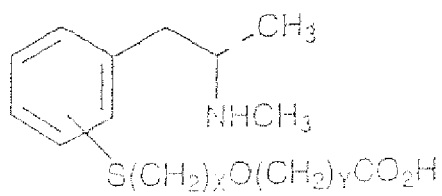
18
X = 2 to 4
Y = 1 to 5
connection at 2,
3, or 4 position
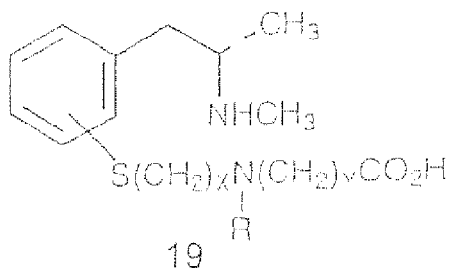
19
X = 2, 3
connection at 2,
3, or 4 position
R = alkyl 1-5 carbon
Fig. 4B

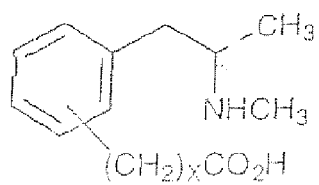
20
X = 3 to 8
connection at 2,
3, or 4 position
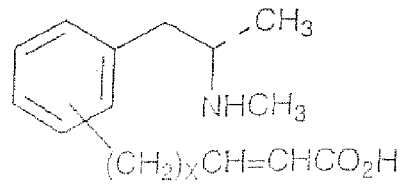
21
X = 2 to 7
connection at 2,
3, or 4 position
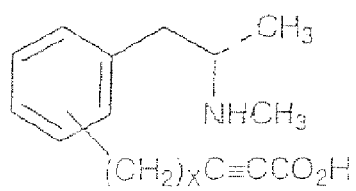
22
X = 2 to 7
connection at 2,
3, or 4 position
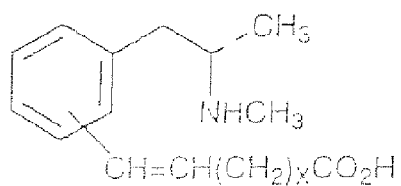
23
X = 1 to 6
connection at 2,
3, or 4 position
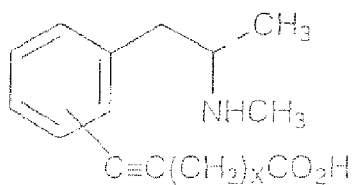
24
X = 1 to 6
connection at 2,
3, or 4 position
Fig. 4C (a) (R)-C₆H₅CH(NH₂)CH₃, toluene
(b) Raney Ni/H₂
(c) HCO₂H/Ac₂O
(d) BBr₃
(e) NaH/Br(CH₂)₅CO₂CH₃
(f) BH₃
(g) Pd/HCO₂H
(h) Dilute HCl

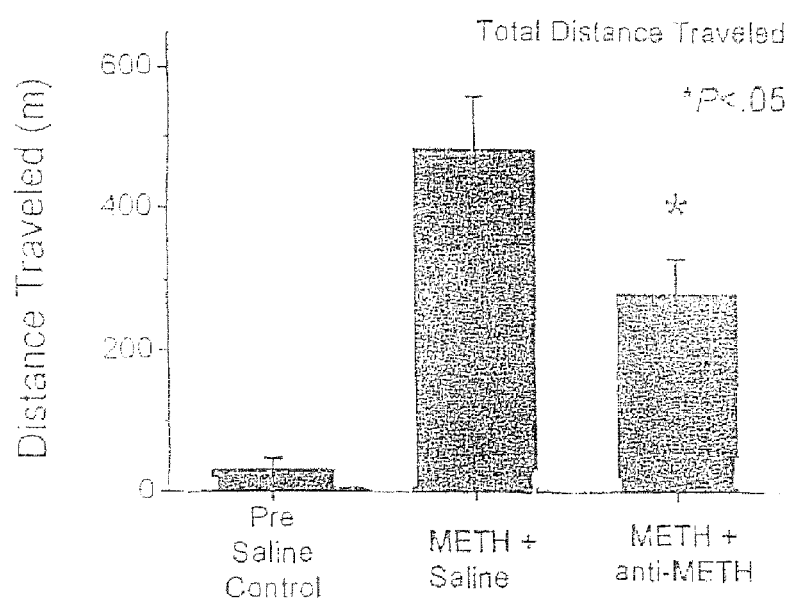
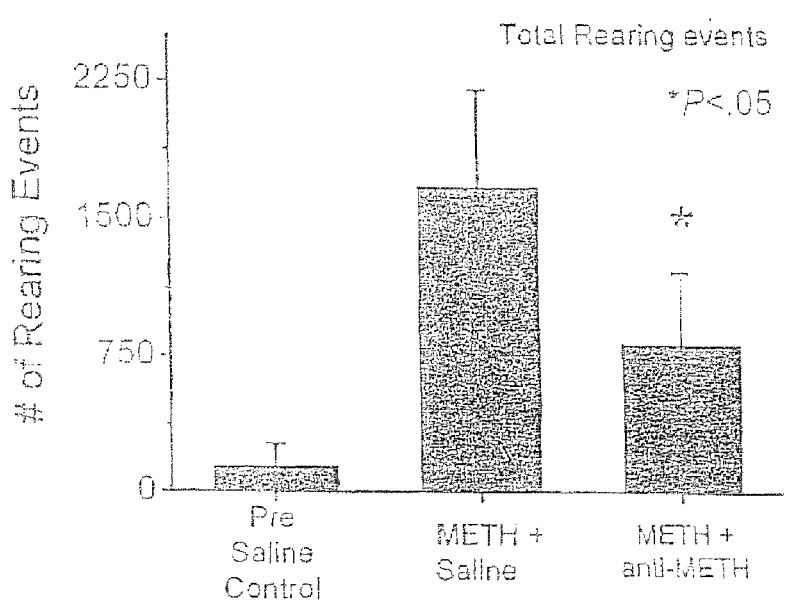
FIG. 16

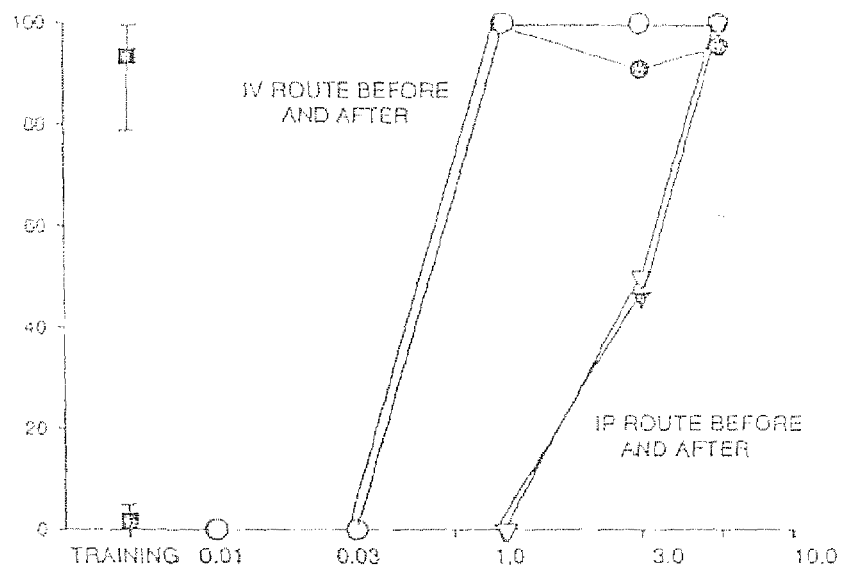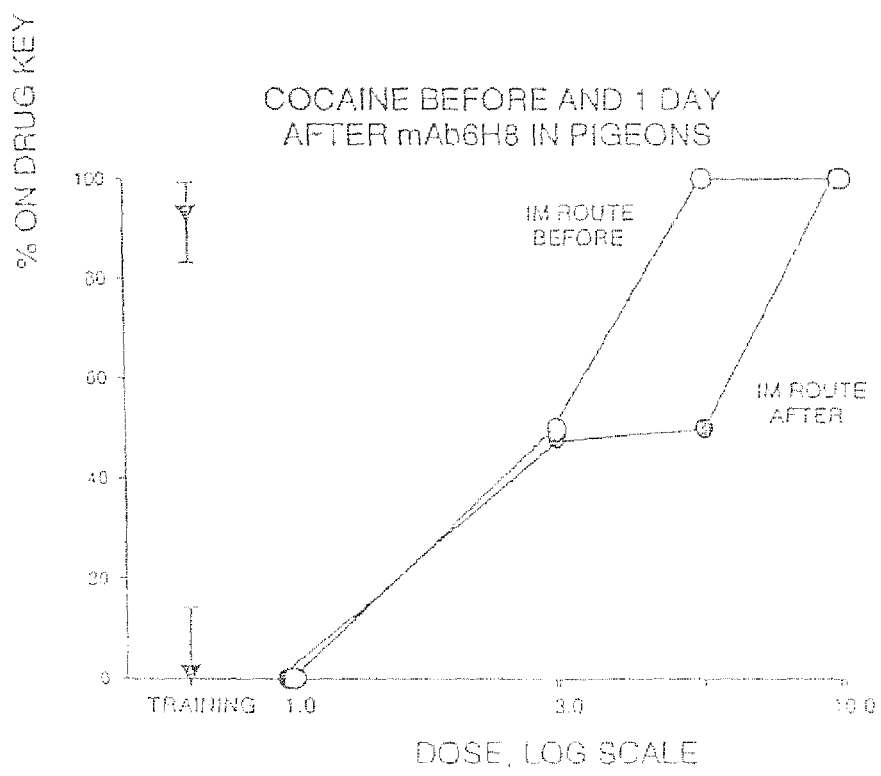
Fig. 24

FIG. 27A

| mAb name | KD (nM) | Heavy chain variable region sequence | SEQ ID NO |
|---|---|---|---|
| 6H8 | 250 | QVQLQQPGAELVKPGASMKISCKASGYTFTSFWMH-WVKQRPGQGLEWIGEINPSNGRNKYNEKFKNKATLTVDKSSSTAYMQLSSLTSEDSAVYYCTRDSFGGSYDGFYSMDYWGQGTSVTVS | SEQ. ID NO. 9 |
| 6H4 | 10 | EVQLQESGPSLVKPSQTLSLTCSVTGDSVTGSSAYYWS-WIRQFPGNKLDYMGYIS-YRGSTYYNPSLKNRISITRDTSKNQFFLKLNSVTTEDTATYYCSYFDSDD-YAMEY---WGQGTSVTVS | SEQ. ID NO. 10 |
| 6H7 | 41 | DVKLQESGPGLVKPSQSLSLTCSVTGSSITSAYYWN-WIRQFPGNKLEWMGYIRYDCYNN-YNPSLKNRISITRDTSKDNSKNQVFLKMNQFLKMNRLQTDDTARYFCARDDVDEAY-----WGQGTLVTVS | SEQ. ID NO. 11 |
| 9B11 | 41 | EVQLPESGPGLVAPSQSLSITCTVSGFSLTDGYGVNWVRQPPGKGLEWLGMIW-DDGDTDYSSVLKSRLSITKDNSKAKLTAVTSTSTAYMELSSLTNEDSAVYYCARDTLYTSYAMDY----WGQGISVIVS | SEQ. ID NO. 12 |
| 4G9 | 40 | EYQLQQSGTVIARPGASVKMSCKASGYTFTSYWMH-WVKQRPGQGLEWIGGIYPGNSDTIYNQKFKGKAKLTAVTSTAYMELSSLTNEDSAVYYCLYGNVDFDY------WGQGTTLTVS | SEQ. ID NO. 13 |

Regions indicated: FR1, CDR H1, FR2, CDR H2, FR3, CDR H3, FR4 (with position numbering 1–112, including 35A, 52A, 82A, 82B, 82C, 100A–100F).

| | | FR1 | | | | | | | | | | | | | | | | | | | | | | |
|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| 6H8 | 250 | Q | I | V | L | T | Q | S | P | A | I | M | S | A | S | P | G | E | K | V | T | I | S | C |
| 6H4 | 10 | Q | I | V | L | T | Q | S | P | A | I | M | S | A | S | P | G | E | K | V | T | L | T | C |
| 6H7 | 41 | Q | I | V | L | T | Q | S | P | A | I | M | S | A | S | P | G | E | K | V | T | L | T | C |
| 9B11 | 41 | Q | A | V | V | T | Q | E | S | A | L | T | T | S | P | G | E | T | V | T | L | T | C |  |
| 4G9 | 40 | D | V | Q | M | T | Q | S | P | S | S | L | S | A | S | L | G | G | K | V | T | I | T | C |

| | | CDR L1 | | | | | | | | | | | | | FR2 | | | | | | | | | | | CDR L2 | | | | | | | | FR3 | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | 24 | 25 | 26 | 27 | 27A | 27B | 27C | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 |
| 6H8 | 250 | S | A | S | S | S | - | - | V | S | - | Y | M | Y | W | Y | Q | Q | K | P | G | S | S | P | K | P | W | I | Y | R | T | S | I | L | A | S | G | V | P | A | R | F |
| 6H4 | 10 | S | A | S | S | S | - | - | V | S | - | Y | M | Y | W | Y | Q | Q | K | P | G | S | S | P | K | P | W | I | Y | R | T | S | N | L | A | S | G | V | P | A | R | F |
| 6H7 | 41 | S | A | S | S | S | V | R | S | S | Y | L | Y | - | - | W | Y | Q | Q | K | P | G | S | S | P | K | L | W | I | Y | S | T | S | N | L | A | S | G | V | P | A | R | F |
| 9B11 | 41 | R | S | S | A | G | A | V | T | A | S | N | Y | A | N | W | V | Q | E | K | P | D | H | L | F | T | G | L | I | G | G | T | N | I | R | A | P | G | I | P | A | R | F |
| 4G9 | 40 | K | A | S | Q | D | I | N | K | F | I | A | - | - | W | Y | Q | H | K | P | G | K | G | P | R | I | I | - | H | Y | T | S | T | L | Q | P | G | I | P | S | R | F |

| | | FR3 (cont.) | | | | | | | | | CDR L3 | | | | | | | | | | FR4 | | | | | | | | | | | |
|---|---|---|---|---|---|---|---|---|---|---|---|---|---|---|---|---|---|---|---|---|---|---|---|---|---|---|---|---|---|---|---|---|
| | | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 95A | 96 | 97 | 98 | 99 | 100 | 101 | 102 | 103 | 104 | 105 | 106 | 107 | 108A | 108 | |
| 6H8 | 250 | S | L | T | I | I | N | M | E | A | E | D | A | A | T | Y | Y | C | Q | H | Y | H | S | Y | P | - | L | T | F | G | A | G | T | K | L | E | L | K | R | A | SEQ. ID NO. 14 |
| 6H4 | 10 | S | L | T | I | S | S | M | E | A | E | D | A | A | S | Y | F | C | H | Q | W | S | S | F | P | - | F | T | F | G | S | G | T | K | L | E | I | K | R | A | SEQ. ID NO. 15 |
| 6H7 | 41 | S | L | T | I | S | S | M | E | A | E | D | A | A | S | Y | F | C | H | Q | W | S | S | Y | P | - | Y | T | F | C | G | G | G | T | K | L | E | I | K | R | A | SEQ. ID NO. 16 |
| 9B11 | 41 | A | L | T | I | T | G | A | Q | T | E | D | E | A | I | Y | F | C | V | L | W | F | S | N | H | S | V | - | F | G | G | G | T | K | L | T | V | L | G | L | SEQ. ID NO. 17 |
| 4G9 | 40 | S | F | S | I | S | N | L | E | P | E | D | I | A | T | Y | Y | C | L | Q | Y | A | N | L | L | P | W | T | F | G | G | G | T | K | L | E | I | K | R | A | SEQ. ID NO. 18 |

FIG. 27B

| mAb Name | CDR Regions and RMSD (Å) from mAb6H4 | | | | | |
| --- | --- | --- | --- | --- | --- | --- |
| | L1 | L2 | L3 | H1 | H2 | H3 |
| mAb6H8 | 2.27 | 0.84 | 0.67 | 1.85 | 3.36 | 6.67 |
| mAb4G9 | 2.44 | 0.88 | 3.72 | 1.39 | 3.59 | 7.22 |

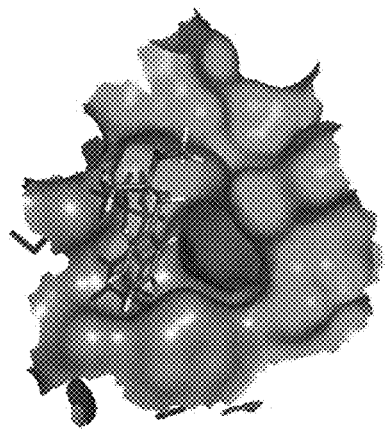
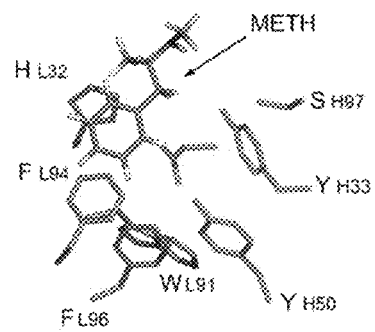
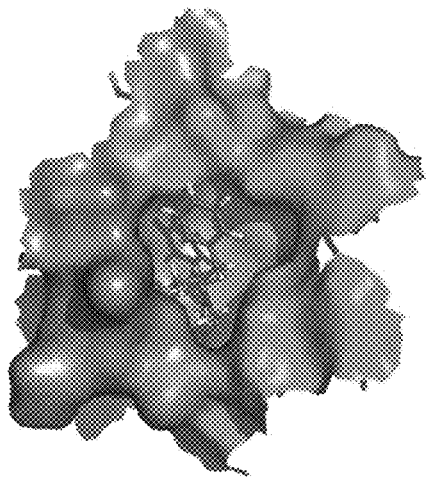
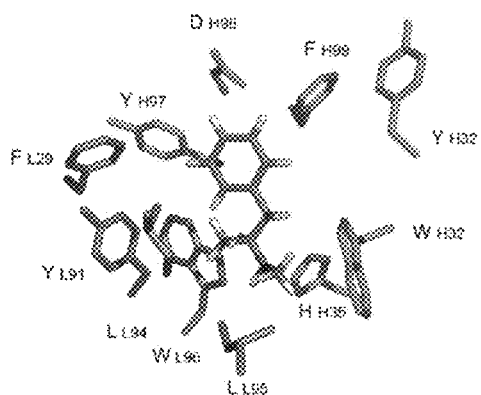
FIG. 29

METHAMPHETAMINE-LIKE HAPTEN COMPOUNDS, LINKERS, CARRIERS AND COMPOSITIONS AND USES THEREOF

PRIORITY STATEMENT

This application is a divisional of U.S. application Ser. No. 12/611,708, filed Nov. 3, 2009 now U.S. Pat. No. 8,299,222, which is a divisional of U.S. application Ser. No. 11/733,085, filed Apr. 9, 2007, now U.S. Pat. No. 7,632,929, which is a continuation in part of U.S. application Ser. No. 10/255,462, filed Sep. 26, 2002, now U.S. Pat. No. 7,202,348, which is a continuation in part of U.S. application Ser. No. 09/839,549, filed Apr. 20, 2001, now U.S. Pat. No. 6,669,937, which claims the benefit of provisional U.S. Application Ser. No. 60/198,902, filed Apr. 20, 2000, now abandoned.

GOVERNMENTAL RIGHTS

This invention was made with government support under DA11560, DA14361, and DA05477 awarded by the National Institute on Drug Abuse. The government has certain rights in the invention.

FIELD OF THE INVENTION

The invention generally relates to hapten compounds comprising either (+)methamphetamine or (+)amphetamine conjugated to a linker. Generally speaking, hapten compounds of the invention may be used to elicit an immune response to one or more of (+) methamphetamine, (+) amphetamine, or (+) 3,4-methylenedioxymethamphetamine ((+) MDMA).

BACKGROUND OF THE INVENTION

Knowledge gained from basic research into the neurobiology of drug abuse has led to major discoveries in medicine. Nevertheless, the development of medical strategies for treating the complex array of neurological problems associated with drug abuse has been frustratingly slow. In particular, development of medical treatments for alleviating the adverse psychosocial and health effects of d-methamphetamine and similar stimulants is badly needed.

d-Methamphetamine-related hospital emergency cases across the U.S. increased 256% from 1991 to 1994 (Collings, 1996). Toxic effects due to excessive d-methamphetamine use led to more than 10,000 hospital visits each year between 1994 and 1999 and were responsible for more than 2,000 deaths over those same 5 years (Drug Abuse Warning Network, December 2000). The 1995 Toxic Exposure Surveillance System data showed there were 7,601 people treated in health care facilities for amphetamine-like drugs and other stimulants. This is particularly striking since during the same period there were only 3,440 cases of cocaine treatment and a total of 5,170 cases of all types of legal and illegal narcotics (including morphine, codeine and heroin). The current rise in d-methamphetamine use is also alarming because, unlike cocaine, it does not have to be imported. Even an amateur chemist can synthesize this drug in his home using easily obtained reagents and equipment.

Methamphetamine overdose patients can be hyperactive, agitated, and paranoid; and even one-time use of a high dose can lead to a psychotic state lasting several days or weeks. Other complications include hyperthermia, seizures, hypertension, and cardiotoxicity. Recent studies suggest that signs of neurotoxicity (e.g., decreased dopamine transporter density) are present in chronic d-methamphetamine abusers, and these changes appear to correlate with a decrease in cognitive function.

Because there are no specific pharmacological therapies for d-methamphetamine overdose, patients receive palliative and supportive care for symptoms while waiting for the drug to be eliminated by metabolism and renal excretion. Emergency care of patients includes maintenance of ventilation, hydration, electrolyte balance and control of body temperature. Some physicians also choose to administer medications to treat seizures, agitation, or hypertensive crises. Such treatments can aid in managing patients' symptoms, but they do so without removing the causative agent. It would be advantageous to have a medication that could quickly antagonize d-methamphetamine effects by removing the drug from the central nervous system, thereby reversing many of the acute toxicities and reducing the potential for long-term neurological damage.

One reason why clinically effective d-methamphetamine agonists or antagonists have not been discovered is that d-methamphetamine acts at several sites in the central nervous system through multiple mechanisms of action. These mechanisms include, but are not limited to, disruption of vesicular storage of dopamine, inhibition of monoamine oxidase, increased dopamine and serotonin release, and inhibition of dopamine and serotonin reuptake by their respective transporters. In addition, it is likely that any chemical antagonist (or agonist) would share at least some of the adverse effects of d-methamphetamine (e.g., disruption of neurotransmitter homeostasis).

One biologically based approach to treat drug overdose is the use of high-affinity, drug-specific antibodies or Fab fragments. In addition to being relatively safe, except for occasional allergic reactions that can be prevented by the use of humanized monoclonal antibodies, antibody-based therapies act as pharmacokinetic antagonists which gives them several important advantages over treatment with more conventional receptor antagonists. Firstly, there is no receptor antagonist for d-methamphetamine effects at any of its sites of action in the CNS. One of the limitations of development of receptor antagonists is that they will only be capable of attenuating the effects at one type of receptor. Most drugs of abuse have multiple sites of action. Secondly, unlike conventional receptor antagonists (or agonists), antibodies do not inhibit the actions of normal endogenous ligands. In fact, it could be argued that removal of the drug by antibodies might allow for a more normal recovery than treatment with a chemically-derived small molecule competitive agonist or antagonist. Thirdly, since antibodies (and their derivatives like Fab) have extremely high affinities and do not cross the blood-brain barrier, they actually lower drug concentrations throughout the CNS. This allows for a rapid, neuroprotective effect at all sites of action in the CNS.

While monoclonal antibody (mAb) therapy could be a viable approach for antagonizing d-methamphetamine effects, several factors complicate the design of antibody therapy for this drug. First, knowledge of the relationship between antibody affinity and therapeutic efficacy is limited. Previous studies have shown that a single dose of a high-affinity anti-phencyclidine mAb Fab fragment ($K_D$=1.8 nM) is very effective at reversing a phencyclidine-induced overdose in rats (Valentine et al., 1996; Hardin et al., 1998), and that the intact IgG ($K_D$=1.3 nM) can produce long-term reductions in brain phencyclidine concentrations (Proksch et al., 2000). While these preclinical data for phencyclidine are impressive, the optimal conditions for achieving such profound effects are not clear. Second, unlike most drugs of abuse, d-methamphetamine (d-METH) has a major active metabolite, d-amphetamine (d-AMP). This metabolite is present at significant concentrations in study rats, and d-AMP area under the concentration-versus-time curves (AUC) constitutes 30% and 26% of the total AUC for d-METH and d-AMP in serum and brain, respectively (Riviere et al., 2000). Thus, pharmacological effects due to d-METH and d-AMP may need to be treated in rats. In humans, however, d-AMP's AUC is <15% of the total serum AUC of d-METH and d-AMP (Cook et al., 1993). Therefore, d-AMP may not contribute as significantly to d-METH's effects in humans.

Thus, the prior art is deficient in the lack of effective means of treating d-methamphetamine overdose and addiction by antibody-based therapy. The present invention fulfills this long-standing need and desire in the art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that the matter in which the recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the use of a long-acting anti-METH antibody medication for the treatment of drug addiction. In this clinical scenario, the patient has entered a drug treatment program for d-methamphetamine addiction and they are treated with a long acting anti-methamphetamine monoclonal antibody-based medication. In this example, the prototype long acting antagonist is an IgG antibody.

FIG. 2 shows the use of short-acting anti-methamphetamine monoclonal antibody fragment to treat an overdose resulting from d-methamphetamine-like drugs. In this case d-methamphetamine is used as the prototype drug and an anti-methamphetamine monoclonal Fab is used as the antibody-based medication.

FIG. 3 shows the structures of methamphetamine-like stimulants.

FIGS. 4A-4C show the hapten 10 to hapten 24 designed for generating antibodies that are specific for methamphetamine-like stimulants.

FIGS. 15 (A and B) shows the results from treatment of a methamphetamine-induced overdose in rats with a monoclonal anti-methamphetamine antibody or anti-phencyclidine monoclonal antibody (a control monoclonal antibody that does not bind amphetamine like drugs). Rats (n=4 per group) were administered saline (left most bar) or 1.0 mg/kg d-methamphetamine as an intravenous bolus dose. When drug effects were maximizing at 30 minutes, they were treated with saline (control), an anti-phencyclidine monoclonal antibody Fab fragment (anti-PCP), or an anti-d-methamphetamine-specific monoclonal antibody Fab fragment (anti-methamphetamine).

FIG. 16 shows the use of anti-(+)METH monoclonal antibodies as a pretreatment to reduce drug effects (administered the day before a 1 mg/kg methamphetamine challenge dose). The anti-(+) methamphetamine monoclonal antibody significantly ($P<0.05$) reduced (+)methamphetamine induced effects by 42% for distance traveled (FIG. 16A) and by 51% for rearing events (FIG. 16B).

FIG. 24 shows dose-response curves for cocaine administered by i.v. and i.p. routes (rats, top panel) or i.m. route (pigeons, bottom panel) before and 1 day after administration of mAb6H8. Abscissa: Mg/kg cocaine on a log scale. Ordinate: Percentage of responses on the drug key. Each point on the dose-response curves represents single observations in two animals from the Rat III group or Pigeon II group. Brackets at TRAINING represent six training sessions after saline and six training sessions for these same subjects.

FIG. 27 presents amino acid sequence alignments of the variable regions of five moderate to high affinity anti-METH and anti-METH/AMP mAb. Panel A presents the amino acid sequences of the heavy chains. Panel B present the amino acid sequences of the light chains. The sequences are presented in single letter amino acid notation and numbered according to Kabat and Wu (1991 J Immunol 147:1709-1719). Location of the framework (FR) and CDR residues are indicated for the heavy chains and light chains.

FIG. 29 illustrates modeled structures of the anti-METH mAb variable chains. In this model, METH (magenta) has been computationally docked into a pocket at the interface of the VH and VL chains with FlexX software. Left panels: Surface rendering of deep pocket in mAb6H4 and mAb4G9. The VL chain domain is on the left side in blue and the VH chain domain is on the right in green. Right panels: Stick representation of mAb6H4 and mAb4G9. Only side chains within 8 angstroms of the METH molecule are shown for clarity. The view is oriented in a "top view" with the same color scheme as in left panel. The side chains are labeled and numbered in the Kabat scheme as in FIG. 27.

SUMMARY OF THE INVENTION

One aspect of the invention encompasses a hapten compound of formula (I):

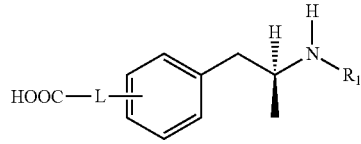

(I)

wherein:
$R_1$ is selected from the group consisting of hydrogen and methyl; and
L comprises a linker of at most 10 contiguous atoms, the atoms being selected from the group consisting of hydrogen, hydrocarbyl, and substituted hydrocarbyl.

Another aspect of the invention encompasses a hapten compound of formula (II):

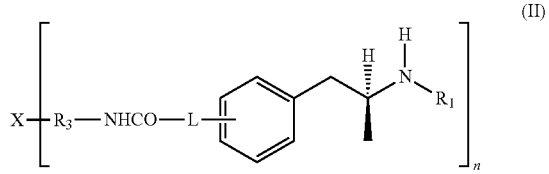

(II)

wherein:
$R_1$ and L are as described for hapten compounds corresponding to formula (I);
n is an integer greater than or equal to 2;
X is a carrier molecule that elicits an immunogenic response; and
$R_3$ is selected from the group consisting of a direct bond, hydrocarbyl, and substituted hydrocarbyl.

Yet another aspect of the invention encompasses a hapten compound of formula (III):

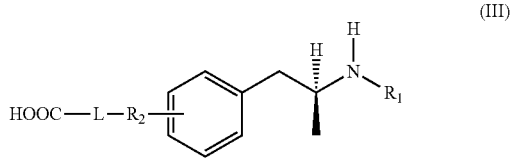

(III)

wherein:
$R_1$ and L is as described for hapten compounds corresponding to formula (I); and
$R_2$ is a heteroatom.

Still another aspect of the invention encompasses a hapten compound of formula (IV):

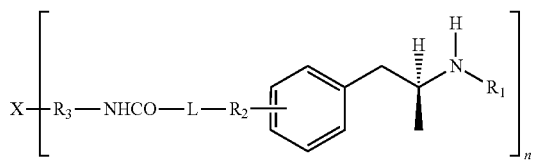

(IV)

wherein:
$R_1$ and L is as described for hapten compounds corresponding to formula (I);
$R_2$ is a heteroatom as described in formula (III); and
N, X, and $R_3$ are described in formula (II).

Still yet another aspect of the invention encompasses a composition. The composition may comprise a compound selected from the group consisting of a compound of formula (I), a compound of formula (II), a compound of formula (III), and a compound of formula (IV).

Other aspects of the invention encompass a method for eliciting an immune response. The method comprises administering a composition to the subject. The composition may comprise a compound selected from the group consisting of a compound of formula (I), a compound of formula (II), a compound of formula (III), and a compound of formula (IV).

Still other aspects of the invention encompass a method for generating specific antibodies for a compound. The compound may be selected from the group consisting of a compound of formula (I), a compound of formula (II), a compound of formula (III), and a compound of formula (IV). The method comprises administering the compound to a subject.

Yet other aspects of the invention encompass a method of treating drug addition. The method comprises eliciting an immune response in a drug-addicted subject by administering a composition to a subject. The composition may comprise a compound selected from the group consisting of a compound of formula (I), a compound of formula (II), a compound of formula (III), and a compound of formula (IV). The immune response elicited decreases the concentration of (+)methamphetamine, (+)amphetamine, or (+)MDMA in the brain of the subject.

DETAILED DESCRIPTION OF THE INVENTION

Part 1

Figure 1A:
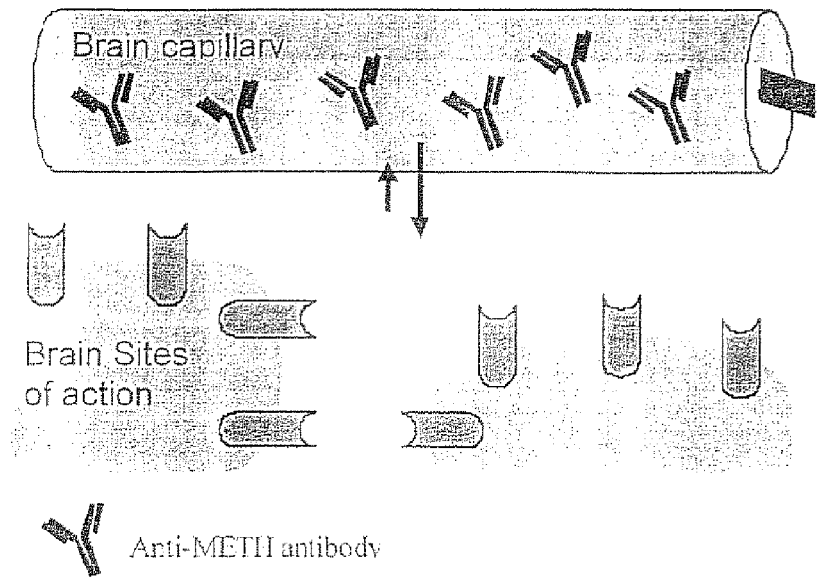
FIG. 1A shows the patient's brain after receiving a dose of a long-acting anti-METH antibody when they enter into a drug treatment program. This medication will serve as a treatment to help prevent or blunt the rewarding effects of methamphetamine-like drug usage by the recovering addict.
Figure 1B:
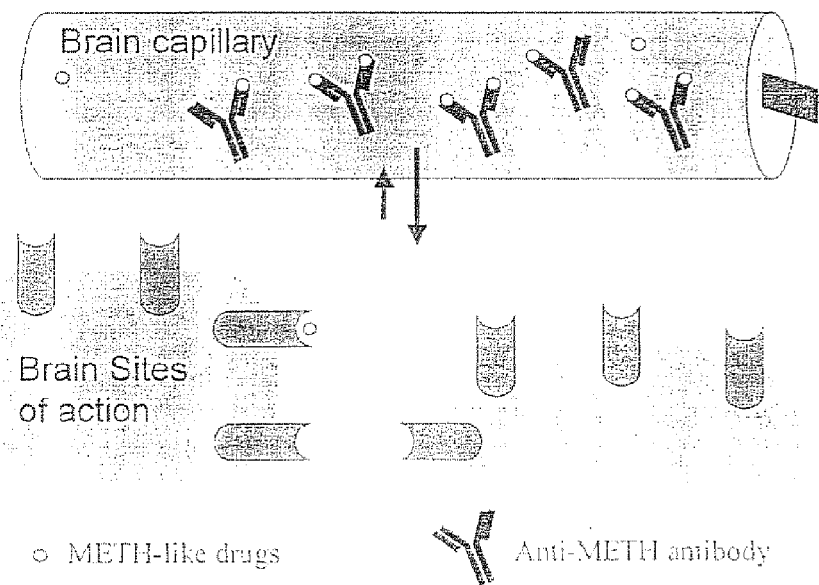
FIG. 1B shows after the patient is pre-treated with the anti-methamphetamine antibody medication, accidental or purposeful use of d-methamphetamine-like drugs by the patient will be blocked or at least significantly blunted. Thus, the drug(s) cannot reach their site of action in the central nervous system. This will prevent the patient from feeling the reinforcing effects of drug use, and aid in the prevention of relapse.
Figure 2A:
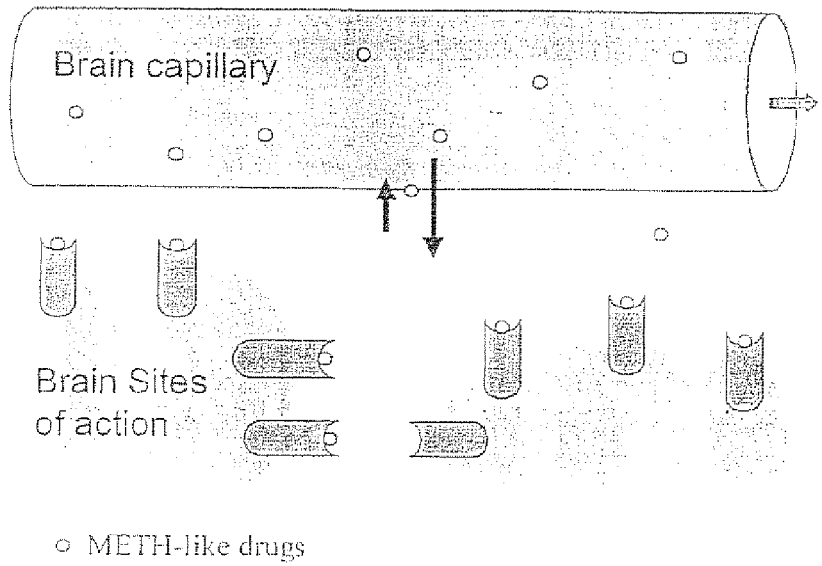
FIG. 2A shows that before the treatment with anti-METH antibody medication, the patient arrives in an emergency room with a high body burden of methamphetamine. This drawing shows that brain concentrations are very high and the drug is occupying drug sites of action in the patient's brain. This is producing the clinical overdose.
Figure 2B:
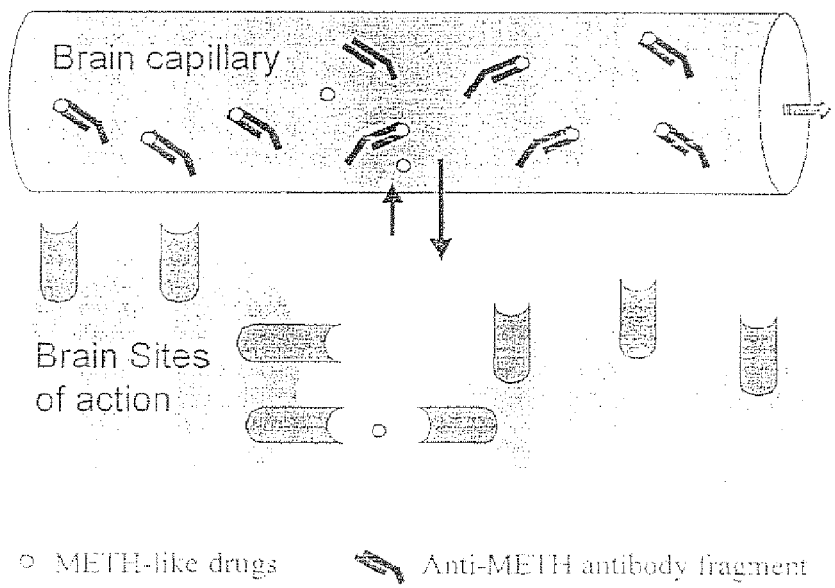
FIG. 2B shows after treatment with anti-methamphetamine antibody fragments, the drug is rapidly removed from the brain and the patient quickly recovers. In this example, the prototype short acting antibody based medication is anti-methamphetamine antibody fragments

This invention encompasses a method of generating high affinity monoclonal antibodies and their antigen binding fragments (e.g., Fab) for use in treating the medical problems associated with stimulant drug abuse. d-Methamphetamine is the prototypic stimulant molecule because it has severe addiction liability and produces significant acute and chronic medical problems. Anti-methamphetamine monoclonal antibody (of any mammalian source) can be used as a prototypic, long acting stimulant antagonist for treating addiction (FIG. 1). In contrast, smaller molecular weight fragments (like Fab) can be used as a prototypic shorter acting, less antigenic, more rapidly eliminated antagonist for treating drug overdose (FIG. 2). Since intact antibody and smaller fragments like Fab are cleared by different organ systems, this approach will also provide a greater potential for altering and controlling the endogenous clearance and biological safety of these proteins.

The current studies disclose the development of anti-d-methamphetamine monoclonal antibodies (mAb) and test the mAb-based therapy in a rat model of d-methamphetamine ((+)-METH) overdose. For all studies, the dose of monoclonal antibody was equimolar in binding sites to the body burden of a 1-mg/kg intravenous (+)-METH dose at 30 min. The results showed that a (+)-METH-specific, high-affinity murine mAb ($K_D$=11 nM) was 2-3 times more effective than a low-affinity mAb ($K_D$=250 nM) at antagonizing (+)-METH-induced locomotor effects. The high-affinity mAb completely reversed locomotor effects produced by 0.3 mg/kg dose of (+)-METH and decreased effects due to 1 mg/kg dose by >60-70%. It was also shown that anti-(+)-METH mAbs antagonize (+)-METH effects by altering brain distribution of (+)-METH. For these studies, rats received 1 mg/kg (+)-METH followed by no treatment (control group) or the mAb at 30 min. The areas under the (+)-METH concentration-versus-time curves showed that the mAb increased the serum area by >9,000% and decreased the brain area by >70%. (+)-Amphetamine serum and brain concentrations were only minimally affected.

Drugs can function as discriminative stimuli to control responding. This function may overlap with the reinforcing stimuli that are produced by the drugs, which in turn can contribute to their self administration and abuse liability. Some investigators suggest that the discriminative stimulus properties of drugs may be related to their subjective effects in humans, although evidence suggests that this relationship is complicated. The discriminative stimulus effects of a drug are often shared among drugs that produce similar pharmacological effects; and some investigators suggest that the shared discriminative-stimulus effects of drugs can be used to define drug classes. For these reasons, drug discrimination has been of great interest to drug abuse researchers.

If the mAbs disclosed herein bind to d-methamphetamine with high affinity, they should prevent the drug from penetrating into the central nervous system to produce its discriminative stimulus effects. If an anti-d-methamphetamine antibody could alter the d-methamphetamine dose-response curve for the discriminative stimulus effects of d-methamphetamine, it would suggest possible therapeutic usefulness of antibody treatment for methamphetamine abuse.

Rats and pigeons were trained to discriminate (+)-methamphetamine (rats), cocaine (rats), or (+)-amphetamine (pigeons) from saline after which dose-response curves were determined for (+)-methamphetamine and other drugs before and after administration of a (+)-methamphetamine specific monoclonal antibody (mAb6H8) ($K_D$=250 nM). Intravenous (+)-methamphetamine was about 3 times more potent as a discriminative stimulus in rats than intraperitoneal (+)-amphetamine. Also in rats, (+)-methamphetamine and (+)-amphetamine were about equipotent as discriminative stimuli and were about 3 times more potent than cocaine. In pigeons, (+)-methamphetamine and (+)-amphetamine were nearly equipotent, while cocaine was slightly less potent. In rats, administration of 1 g/kg of the antibody shifted both intravenous and intraperitoneal dose-response curves for (+)-methamphetamine discrimination approximately 3-fold to the right for up to 7 days. A similar shift of approximately 3-fold to the right that lasted for at least 7 days occurred when the 1 g/kg dose of the antibody was given to pigeons. The antibody did not affect the (+)-amphetamine or cocaine dose-response curves. The effects of a second (+)-methamphetamine monoclonal antibody (mAb6H4)($K_D$=10 nM) also were studied in both rats and pigeons. The higher affinity antibody produced a 3-10 fold shift to the right of the (+)-methamphetamine dose-response curve for drug discrimination in both species. These data showed that (+)-methamphetamine-specific antibodies can produce an antagonism of an effect of (+)-methamphetamine that is closely associated with its abuse.

As used herein, the term "monoclonal antibody" means an antibody composition recognizing a discrete antigen determinant. It is not intended to be limited with regard to the source of the antibody or the manner in which it is made. The term antibody is also intended to encompass whole antibodies, biologically functional fragments thereof, chimeric, humanized, and human antibodies comprising portions from more than one species, or other molecules whose binding properties are derived from antibody-like high affinity binding sites.

In this instance, monoclonal antibodies were produced by hybridomas. However, monoclonal Fab fragments and IgG fragments can also be produced by other methods, for example by using bacteriophage to display and select polypeptide chains expressed from a V-gene library or genetic engineering.

Biologically functional antibody fragments are those fragments sufficient for binding to the desired stimulant drug, such as Fab, Fv, F(ab')$_2$, sFv, scFv (single-chain antigen-binding protein), and scAb fragments. One can choose among these or whole antibodies for the properties appropriate to a particular method.

Chimeric antibodies can comprise proteins derived from two different species. The portions derived from two different species can be joined together chemically by conventional techniques or can be prepared as a single contiguous protein using genetic engineering techniques (See e.g. Cabilly et al., U.S. Pat. No. 4,816,567; Neuberger et al., WO 86/01533 and Winter, EP 0,239,400). Such engineered antibodies can be, for instance, a chimeric antibody comprising murine variable regions and human constant regions, or complementarity determining regions (CDR)-grafted antibodies (Tempest et al., 1991). The constant region domains can be chosen to have an isotype most suitable for the intended application of the antibodies.

It is contemplated that pharmaceutical compositions may be prepared using the antibodies of the present invention. In such a case, the pharmaceutical composition comprises the monoclonal antibodies or antigen-binding fragments thereof of the present invention and a pharmaceutically acceptable carrier. The present invention has included the calculation and administration of equimolar amount of antibodies, and a person having ordinary skill in this art would readily be able to determine, without undue experimentation, the appropriate dosages and routes of administration of the monoclonal antibodies of the present invention. When used in vivo for therapy, the monoclonal antibodies of the present invention are administered to the patient or an animal in therapeutically effective amounts, i.e., amounts that eliminate or reduce the effects of stimulant drug overdose or abuse.

In addition to the obvious benefits of a new therapeutic approach, other important contributions would be derived from the present invention. In as much as the binding properties of receptors and antibodies are similar in many ways, the careful design of amphetamine-like haptens could lead to the selection of antibodies that mimic aspects of the endogenous binding sites of these drugs in the CNS. Molecular studies of these antibody binding sites (through protein sequencing, structure-activity studies and molecular modeling) could aid in the prediction of the characteristics necessary for drug-receptor interaction including neuronal transporters, vesicular storage systems, and with monoamine oxidase. Molecular studies of the sequence of the antibody binding site and the neuronal transporters may also yield important clues concerning the structural rules for molecular interactions of biologically active compounds. Furthermore, the use of these antibody models for screening peptide and organic combinatorial libraries could lead to discovery of novel agonists or antagonists for these neuronal transporters.

The present invention is directed to a monoclonal antibody or an antigen binding fragment thereof that specifically recognizes a stimulant drug of abuse or a metabolite thereof. Representative drugs of abuse or such metabolites include d-methamphetamine, d-amphetamine, 3,4-methylenedioxymethamphetamine, 3,4-methylenedioxyamphetamine and structurally-related analogs of these compounds. In one form, the antibody is of murine origin. Alternatively, the antibody is of human origin or contains portions of a human antibody.

As used herein, "structurally-related analogs" refers to any known or unknown chemical moiety (including drug metabolites) that has a similar chemical structure, and similar pharmacological effects (e.g., behavioral and receptor binding effects) to other known d-methamphetamine-like drugs. For example, phencyclidine (a different drug of abuse) has structurally related analogs like N-ethyl-1-phenylcyclohexylamine (PCE) and 1-[1-(2-thienyl]piperidine (TCP), which are also drugs of abuse (see Owens et al. 1988 for a similar discussion for developing anti-PCP antibodies which recognize structural and pharmacologic similarities in drugs of abuse). Morphine has structurally related analogs like heroin, which is also abused. Fentanyl has a number of structurally related analogs, which have been used as drugs of abuse. In the cases phencyclidine and fentanyl these structurally related drugs are sometimes referred to as designer drugs, because they mimic the effects which are desired by drug abusers.

The present invention also provides methods of treating stimulant drug abuse or overdose, comprising the step of administering a pharmacological effective dose of the monoclonal antibody or an antigen binding fragment thereof of the present invention to an individual in need of such treatment. Representative stimulant drugs are described above.

The present invention is also directed to a method of generating a class-specific monoclonal antibody that recognizes methamphetamine-like stimulants, comprising the step of: immunizing animals with the substituted methamphetamines or hydrochlorides thereof disclosed herein.

Part 2

The present invention is also directed to hapten compounds.

I. Hapten Compounds

One aspect of the invention encompasses a hapten compound that comprises either (+) methamphetamine or (+) amphetamine conjugated to a linker. Generally speaking, the hapten compound is designed to elicit an immune response in a subject that generates antibodies that recognize one or more of (+) methamphetamine, (+) amphetamine, or (+) 3,4-methylenedioxymethamphetamine ((+) MDMA). In certain embodiments, the hapten compound is designed to generate antibodies that recognize at least two compounds from the group consisting of (+) methamphetamine, (+) amphetamine, and (+) MDMA. In an exemplary embodiment, the compound is designed to generate antibodies that recognize all three compounds of the group consisting of (+) methamphetamine, (+) amphetamine, and (+) MDMA.

In one embodiment, the hapten compound has formula (I):

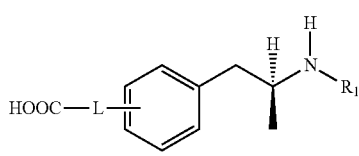

wherein:
$R_1$ is hydrogen or a methyl; and
L is a linker.

In some embodiments, $R_1$ is hydrogen (i.e., forming (+) amphetamine). In other embodiments, $R_1$ is a methyl group (i.e., forming (+) methamphetamine).

In general, L is comprised of atoms so as to facilitate an orientation of the (+) methamphetamine or (+) amphetamine sufficient to generate desired antibodies. In this context, "desired" antibodies include antibodies that recognize (+) methamphetamine, (+) amphetamine, or (+) MDMA. L is also typically not strongly immunogenic. In other words, L may be designed so that antibodies generated against a compound of the invention recognize the compound and not merely L.

Furthermore, in exemplary embodiments, L is designed to generate antibodies with a long functional half-life. For more details, see the examples.

The length of L may be expressed as the number of contiguous atoms forming the shortest path from one substructure that L connects to the other substructure. Typically, L may not be longer than 10 contiguous atoms. In one embodiment, L is at least 2, but not more than 10 contiguous atoms in length. In another embodiment, L may be 2, 3, 4, 5, 6, 7, 8, 9, or 10 contiguous atoms in length. In yet another embodiment, L may be about 5 to 10 contiguous atoms.

As will be appreciated by a skilled artisan, the atoms comprising L may vary widely. Typically, the atoms impart the appropriate degree of flexibility, as detailed above. Suitable atoms forming L may be selected from the group comprising hydrogen, hydrocarbyl, substituted hydrocarbyls, and heteroatoms. In some embodiments, L may be comprised of amino acids, such as glycine or proline. In other embodiments, L may be comprised of nucleotides. In further embodiments, L may be linear, branched, or may comprise ring structures.

It is also envisioned that L may be attached to the benzene ring of (+) methamphetamine or (+) amphetamine at a variety of positions without departing from the scope of the invention. For example, in one embodiment, L may be attached at the meta position of the benzene ring as shown in formula (V):

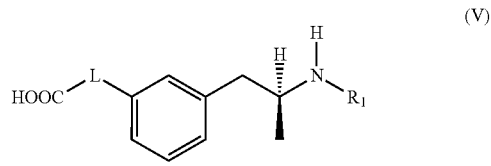

wherein:
L and $R_1$ have the same substituents as detailed for compounds corresponding to formula (I).

In another embodiment, L may be attached at the ortho position as shown in formula (VI):

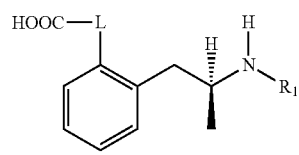

wherein:
L and $R_1$ have the same substituents as detailed for compounds corresponding to formula (I).

In yet another embodiment, L may be attached at the para position as shown in formula (VII):

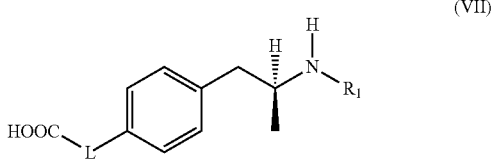
(VII)

wherein:
L and $R_1$ have the same substituents as detailed for compounds corresponding to formula (I).

Exemplary embodiments of L may be comprised of ⫯$(CH_2)_m$, wherein m is an integer between about 5 and about 10, wherein m is an integer between about 6 and about 10, wherein m is an integer between about 7 and 10; wherein m is an integer between about 8 and 10, wherein m is 9, and wherein m is 10. In other exemplary embodiments L may be comprised of ⫯$O(CH_2)_m$, wherein m is an integer between about 5 and 9, wherein m is an integer between about 6 and 9, wherein m is an integer between about 7 and 9; wherein m is 8, and wherein m is 9. In an alternative embodiment, L may be comprised of a group listed in Table A.

TABLE A

| L Group | Position on Benzene Ring |
|---|---|
| —$(CH_2)$ | Para |
| —$(CH_2)$ | Meta |
| —$(CH_2)$ | Ortho |
| —$(CH_2)_2$ | Para |
| —$(CH_2)_2$ | Meta |
| —$(CH_2)_2$ | Ortho |
| —$(CH_2)_3$ | Para |
| —$(CH_2)_3$ | Meta |
| —$(CH_2)_3$ | Ortho |
| —$(CH_2)_4$ | Para |
| —$(CH_2)_4$ | Meta |
| —$(CH_2)_4$ | Ortho |
| —$(CH_2)_5$ | Para |
| —$(CH_2)_5$ | Meta |
| —$(CH_2)_5$ | Ortho |
| —$(CH_2)_6$ | Para |
| —$(CH_2)_6$ | Meta |
| —$(CH_2)_6$ | Ortho |
| —$(CH_2)_7$ | Para |
| —$(CH_2)_7$ | Meta |
| —$(CH_2)_7$ | Ortho |
| —$(CH_2)_8$ | Para |
| —$(CH_2)_8$ | Meta |
| —$(CH_2)_8$ | Ortho |
| —$(CH_2)_9$ | Para |
| —$(CH_2)_9$ | Meta |
| —$(CH_2)_9$ | Ortho |
| —$(CH_2)_{10}$ | Para |
| —$(CH_2)_{10}$ | Meta |
| —$(CH_2)_{10}$ | Ortho |
| —$O(CH_2)$ | Para |
| —$O(CH_2)$ | Meta |
| —$O(CH_2)$ | Ortho |
| —$O(CH_2)_2$ | Para |
| —$O(CH_2)_2$ | Meta |
| —$O(CH_2)_2$ | Ortho |
| —$O(CH_2)_3$ | Para |
| —$O(CH_2)_3$ | Meta |
| —$O(CH_2)_3$ | Ortho |
| —$O(CH_2)_4$ | Para |

TABLE A-continued

| L Group | Position on Benzene Ring |
|---|---|
| —$O(CH_2)_4$ | Meta |
| —$O(CH_2)_4$ | Ortho |
| —$O(CH_2)_5$ | Para |
| —$O(CH_2)_5$ | Meta |
| —$O(CH_2)_5$ | Ortho |
| —$O(CH_2)_6$ | Para |
| —$O(CH_2)_6$ | Meta |
| —$O(CH_2)_6$ | Ortho |
| —$O(CH_2)_7$ | Para |
| —$O(CH_2)_7$ | Meta |
| —$O(CH_2)_7$ | Ortho |
| —$O(CH_2)_8$ | Para |
| —$O(CH_2)_8$ | Meta |
| —$O(CH_2)_8$ | Ortho |
| —$O(CH_2)_9$ | Para |
| —$O(CH_2)_9$ | Meta |
| —$O(CH_2)_9$ | Ortho |
| ‡—X | Para |
| ‡—X | Meta |
| ‡—X | Ortho |
| ‡—$X_2$ | Para |
| ‡—$X_2$ | Meta |
| ‡—$X_2$ | Ortho |
| ‡—$X_3$ | Para |
| ‡—$X_3$ | Meta |
| ‡—$X_3$ | Ortho |
| ‡—$X_4$ | Para |
| ‡—$X_4$ | Meta |
| ‡—$X_4$ | Ortho |
| ‡—$X_5$ | Para |
| ‡—$X_5$ | Meta |
| ‡—$X_5$ | Ortho |
| ‡—$X_6$ | Para |
| ‡—$X_6$ | Meta |
| ‡—$X_6$ | Ortho |
| ‡—$X_7$ | Para |
| ‡—$X_7$ | Meta |
| ‡—$X_7$ | Ortho |
| ‡—$X_8$ | Para |
| ‡—$X_8$ | Meta |
| ‡—$X_8$ | Ortho |
| ‡—$X_9$ | Para |
| ‡—$X_9$ | Meta |
| ‡—$X_9$ | Ortho |
| ‡—$X_{10}$ | Para |
| ‡—$X_{10}$ | Meta |
| ‡—$X_{10}$ | Ortho |

‡ wherein X may be any atom selected from the group comprising C, O, N, P and S; including the appropriate number of hydrogens to balance charge.

Figure 35:
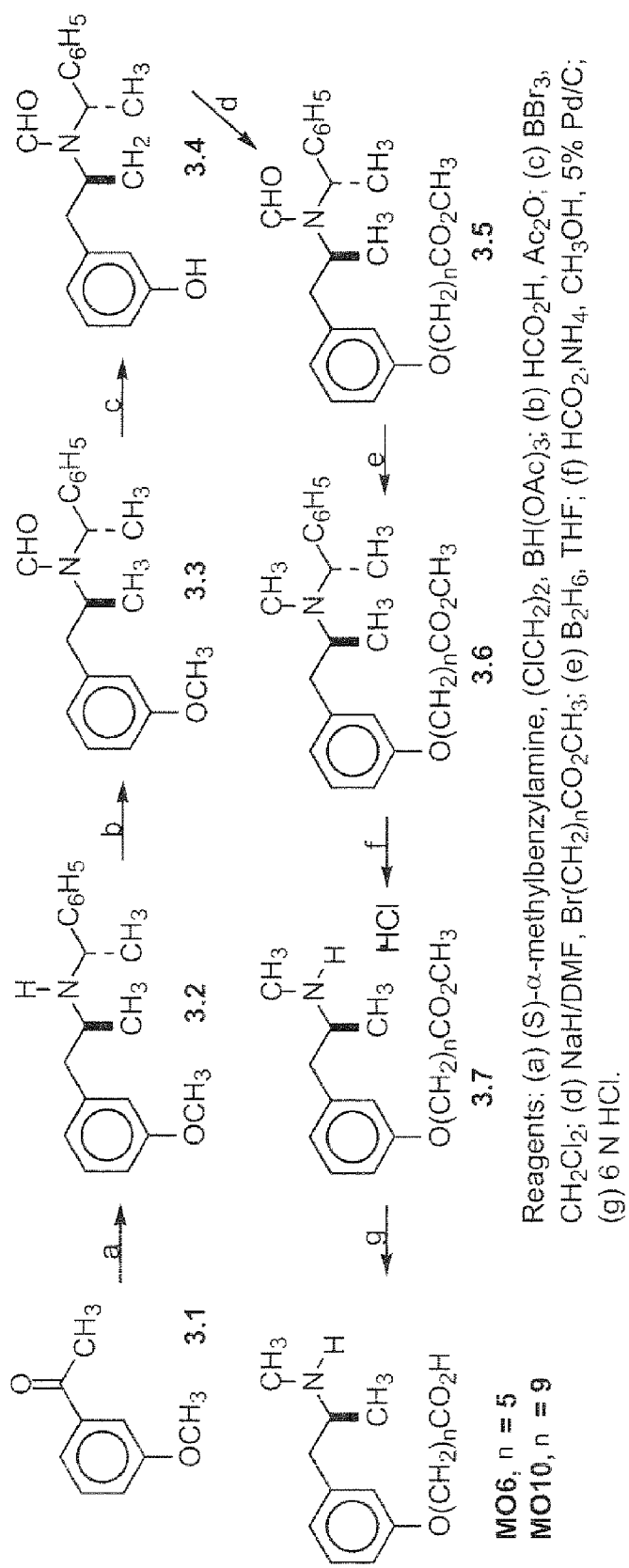
FIG. 35 presents a diagram illustrating the preparation of hapten compounds with carboxylic acid-ending groups.

Methods of making hapten compounds of formula (I) are known in the art or are otherwise described herein. For instance, see FIG. 35 depicting a scheme illustrating the preparation of hapten compounds of the invention with carboxylic acid-ending groups.

In another embodiment, the compound may have formula (III):

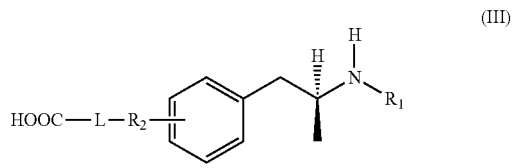
(III)

wherein:
$R_1$ and L are as described for hapten compounds corresponding to formula (I).; and
$R_2$ may be a heteroatom.

In certain embodiments for compounds corresponding to formula (III), $R_2$ may be a carbon atom, an oxygen atom, a nitrogen atom, a sulfur atom, or a phosphorous atom. In one alternative embodiment, $R_2$ may be a carbon atom. In another alternative embodiment, $R_2$ may be an oxygen atom. In yet another alternative embodiment, $R_2$ may be a nitrogen atom. In still yet another alternative embodiment, $R_2$ may be a phosphorous atom. In an additional alternative embodiment, $R_2$ may be a sulfur atom.

In an exemplary embodiment, a compound of formula (III) may have oxygen for $R_2$ and $(CH_2)_9$ as L.

Other exemplary hapten compounds having formula (I) or (III) are shown in Table A.

II. Hapten Compounds Conjugated to Carrier Molecules

In another aspect of the invention, any of the hapten compounds having formulas (I) or (III) may be conjugated, via a linker, L, to a carrier molecule X. Generally speaking, the carrier molecule is selected so that it enhances the immunogenicity of the hapten compound. For instance, the carrier molecule may provide a T-cell epitope to enhance the immunogenicity of the hapten compound. These compounds may be utilized for a variety of suitable uses, including, as a therapeutic immunogenic compound (described in more detail herein), and to elicit the generation of antibodies that may be utilized in passive therapies or in methods of purification or detection.

In one embodiment, a hapten compound corresponding to formula (I) is conjugated via L to a carrier molecule, X, to form a compound having formula (II):

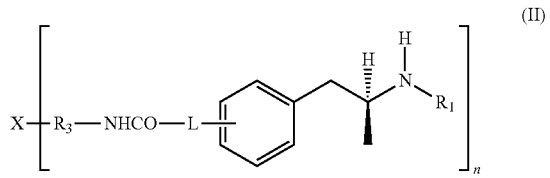

(II)

wherein:
$R_1$ and L are as described for hapten compounds corresponding to formula (I);
$R_3$ may be selected from the group comprising a direct bond, hydrocarbyl, and substituted hydrocarbyl;
X is a carrier molecule that is capable of eliciting an immune response; and
n is an integer greater than or equal to 2.

In one alternative embodiment, $R_3$ may be a direct bond. In another alternative embodiment, $R_3$ may be a hydrocarbyl. In yet another alternative embodiment, $R_3$ may be a substituted hydrocarbyl. In an exemplary alternative of this embodiment, $R_3$ may be $(CH_2)_4$ or $(CH_2)_4NHCO(CH_2)_5$.

Typically, X may be a protein, lipid, carbohydrate, or any combination thereof that is capable of eliciting an immune response. For instance, in one embodiment, X may be a polysaccharide, such as mannan. In another embodiment, X may be a lipopolysaccharide, such as a lipopolysaccharide derived from *Salmonella typhosa*.

In exemplary embodiments, X is a protein. In a particular embodiment X may be selected from the group of proteins comprising keyhole limpet hemocyanin (KLH), ovalbumin, bovine serum albumin (BSA), sheep albumin, thyroglobulin, and any modifications, derivatives, or analogues thereof. For instance, in one embodiment, X may be BSA or cationized BSA. In another embodiment, X may be KLH. In yet another embodiment, X may be thyroglobulin. In still yet another embodiment, X may be ovalbumin.

In another particular embodiment, X may be a bacterial toxin or toxoid. Non-limiting examples of suitable bacterial toxins or toxoids may include tetanus toxoid, diphtheria toxoid, non-toxic mutant diphtheria toxoid $CRM_{197}$, outer membrane protein complex (OMPC) from *Neisseria meningitidis*, the B subunit of heat-labile *Escherichia coli*, recombinant exoprotein A from *Pseudomonas aeruginosa* (rEPA), cholera toxin B-(CTB), pertussis toxin and filamentous hemagglutinin, shiga toxin, and the LTB family of bacterial toxins.

In yet another embodiment, X may be a lectin. Non-limiting examples of suitable lectins may include ricin-B subunit, abrin and sweet pea lectin.

In an alternative embodiment, X may be selected from the group comprising retrovirus nucleoprotein (retro NP), rabies ribonucleoprotein (rabies RNP), plant viruses (e.g. TMV, cow pea and cauliflower mosaic viruses), vesicular stomatitis virus-nucleocapsid protein (VSV-N), poxvirus subunits and Semliki forest virus subunits.

In another alternative embodiment, X may be an artificial molecular carrier. Non-limiting examples of an artificial molecular carrier include multiantigenic peptides (MAP) and microspheres. In an additional embodiment X may be yeast virus-like particles (VLPs). In another additional embodiment, X may be a malarial protein antigen.

Furthermore, X may be selected from the group comprising Diphtheria, Tetanus, and Pertussis vaccines or components thereof; poliovirus vaccines and components thereof; Rubella, Mumps, and Measles vaccines or components thereof; Hepatitis vaccines (A,B,C, and delta) and components thereof; *Haemophilus* (A and B) vaccines and components thereof; vaccinia and smallpox vaccines and components thereof; and varicella-zoster vaccines and components thereof.

In a preferred embodiment, X may be a pharmaceutically acceptable carrier for human subjects. In other words, X may be a carrier that safely elicits an antibody response in a subject. In this context, the term "safely" means that the carrier does not substantially elicit an immune response that cross-reacts with a self-protein, or a regularly ingested protein of the subject. Non-limiting examples of pharmaceutically acceptable carriers for use in human subjects include mutant diphtheria toxoid ($CRM_{197}$) and tetanus toxoid. In one preferred embodiment, X may be diphtheria toxoid $CRM_{197}$. In another preferred embodiment, X may be tetanus toxoid.

To increase the elicited immune response to a hapten compound of the invention, generally more than one hapten compound is conjugated to an individual carrier molecule, X, as expressed by n (i.e., the number of hapten compounds conjugated to X). Generally speaking, n is an integer greater than or equal to 2. In one embodiment, n may be 2, 3, 4, or 5. In another embodiment, n may be 6, 7, 8, or 9. In an exemplary embodiment, n is greater than or equal to 5.

In another embodiment, a hapten compound corresponding to formula (III) is conjugated via L to a carrier molecule, X, to form a compound having formula (IV):

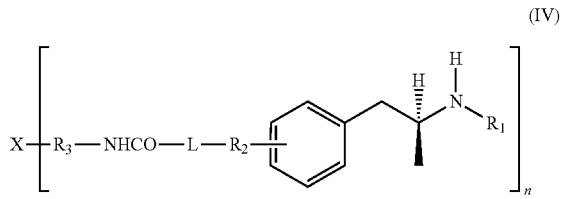

(IV)

wherein:
$R_1$, L, n, and X are as described for compounds corresponding to formula (II);

$R_2$ is as described for compounds corresponding to formula (III); and $R_3$ may be selected from the group comprising a direct bond, hydrocarbyl, and substituted hydrocarbyl. In an exemplary alternative of this embodiment, $R_3$ is $(CH_2)_4$ or $(CH_2)_4NHCO(CH_2)_5$.

Exemplary compounds of the invention having formulas (II) and (IV) are shown in Table B.

TABLE B

| L Group | Position on Benzene Ring | Carrier |
|---|---|---|
| —(CH$_2$) | Para | KLH |
| —(CH$_2$) | Para | Ovalbumin |
| —(CH$_2$) | Para | BSA |
| —(CH$_2$) | Para | Diptheria CRM$_{197}$ |
| —(CH$_2$) | Para | Tetanus toxoid |
| —(CH$_2$) | Meta | KLH |
| —(CH$_2$) | Meta | Ovalbumin |
| —(CH$_2$) | Meta | BSA |
| —(CH$_2$) | Meta | Diptheria CRM$_{197}$ |
| —(CH$_2$) | Meta | Tetanus toxoid |
| —(CH$_2$)$_2$ | Para | KLH |
| —(CH$_2$)$_2$ | Para | Ovalbumin |
| —(CH$_2$)$_2$ | Para | BSA |
| —(CH$_2$)$_2$ | Para | Diptheria CRM$_{197}$ |
| —(CH$_2$)$_2$ | Para | Tetanus toxoid |
| —(CH$_2$)$_2$ | Meta | KLH |
| —(CH$_2$)$_2$ | Meta | Ovalbumin |
| —(CH$_2$)$_2$ | Meta | BSA |
| —(CH$_2$)$_2$ | Meta | Diptheria CRM$_{197}$ |
| —(CH$_2$)$_2$ | Meta | Tetanus toxoid |
| —(CH$_2$)$_3$ | Para | KLH |
| —(CH$_2$)$_3$ | Para | Ovalbumin |
| —(CH$_2$)$_3$ | Para | BSA |
| —(CH$_2$)$_3$ | Para | Diptheria CRM$_{197}$ |
| —(CH$_2$)$_3$ | Para | Tetanus toxoid |
| —(CH$_2$)$_3$ | Meta | KLH |
| —(CH$_2$)$_3$ | Meta | Ovalbumin |
| —(CH$_2$)$_3$ | Meta | BSA |
| —(CH$_2$)$_3$ | Meta | Diptheria CRM$_{197}$ |
| —(CH$_2$)$_3$ | Meta | Tetanus toxoid |
| —(CH$_2$)$_4$ | Para | KLH |
| —(CH$_2$)$_4$ | Para | Ovalbumin |
| —(CH$_2$)$_4$ | Para | BSA |
| —(CH$_2$)$_4$ | Para | Diptheria CRM$_{197}$ |
| —(CH$_2$)$_4$ | Para | Tetanus toxoid |
| —(CH$_2$)$_4$ | Meta | KLH |
| —(CH$_2$)$_4$ | Meta | Ovalbumin |
| —(CH$_2$)$_4$ | Meta | BSA |
| —(CH$_2$)$_4$ | Meta | Diptheria CRM$_{197}$ |
| —(CH$_2$)$_4$ | Meta | Tetanus toxoid |
| —(CH$_2$)$_5$ | Para | KLH |
| —(CH$_2$)$_5$ | Para | Ovalbumin |
| —(CH$_2$)$_5$ | Para | BSA |
| —(CH$_2$)$_5$ | Para | Diptheria CRM$_{197}$ |
| —(CH$_2$)$_5$ | Para | Tetanus toxoid |
| —(CH$_2$)$_5$ | Meta | KLH |
| —(CH$_2$)$_5$ | Meta | Ovalbumin |
| —(CH$_2$)$_5$ | Meta | BSA |
| —(CH$_2$)$_5$ | Meta | Diptheria CRM$_{197}$ |
| —(CH$_2$)$_5$ | Meta | Tetanus toxoid |
| —(CH$_2$)$_6$ | Para | KLH |
| —(CH$_2$)$_6$ | Para | Ovalbumin |
| —(CH$_2$)$_6$ | Para | BSA |
| —(CH$_2$)$_6$ | Para | Diptheria CRM$_{197}$ |
| —(CH$_2$)$_6$ | Para | Tetanus toxoid |
| —(CH$_2$)$_6$ | Meta | KLH |
| —(CH$_2$)$_6$ | Meta | Ovalbumin |
| —(CH$_2$)$_6$ | Meta | BSA |
| —(CH$_2$)$_6$ | Meta | Diptheria CRM$_{197}$ |
| —(CH$_2$)$_6$ | Meta | Tetanus toxoid |
| —(CH$_2$)$_7$ | Para | KLH |
| —(CH$_2$)$_7$ | Para | Ovalbumin |
| —(CH$_2$)$_7$ | Para | BSA |
| —(CH$_2$)$_7$ | Para | Diptheria CRM$_{197}$ |
| —(CH$_2$)$_7$ | Para | Tetanus toxoid |
| —(CH$_2$)$_7$ | Meta | KLH |
| —(CH$_2$)$_7$ | Meta | Ovalbumin |
| —(CH$_2$)$_7$ | Meta | BSA |
| —(CH$_2$)$_7$ | Meta | Diptheria CRM$_{197}$ |
| —(CH$_2$)$_7$ | Meta | Tetanus toxoid |
| —(CH$_2$)$_8$ | Para | KLH |
| —(CH$_2$)$_8$ | Para | Ovalbumin |
| —(CH$_2$)$_8$ | Para | BSA |
| —(CH$_2$)$_8$ | Para | Diptheria CRM$_{197}$ |
| —(CH$_2$)$_8$ | Para | Tetanus toxoid |
| —(CH$_2$)$_8$ | Meta | KLH |
| —(CH$_2$)$_8$ | Meta | Ovalbumin |
| —(CH$_2$)$_8$ | Meta | BSA |
| —(CH$_2$)$_8$ | Meta | Diptheria CRM$_{197}$ |
| —(CH$_2$)$_8$ | Meta | Tetanus toxoid |
| —(CH$_2$)$_9$ | Para | KLH |
| —(CH$_2$)$_9$ | Para | Ovalbumin |
| —(CH$_2$)$_9$ | Para | BSA |
| —(CH$_2$)$_9$ | Para | Diptheria CRM$_{197}$ |
| —(CH$_2$)$_9$ | Para | Tetanus toxoid |
| —(CH$_2$)$_9$ | Meta | KLH |
| —(CH$_2$)$_9$ | Meta | Ovalbumin |
| —(CH$_2$)$_9$ | Meta | BSA |
| —(CH$_2$)$_9$ | Meta | Diptheria CRM$_{197}$ |
| —(CH$_2$)$_9$ | Meta | Tetanus toxoid |
| —(CH$_2$)$_{10}$ | Para | KLH |
| —(CH$_2$)$_{10}$ | Para | Ovalbumin |
| —(CH$_2$)$_{10}$ | Para | BSA |
| —(CH$_2$)$_{10}$ | Para | Diptheria CRM$_{197}$ |
| —(CH$_2$)$_{10}$ | Para | Tetanus toxoid |
| —(CH$_2$)$_{10}$ | Meta | KLH |
| —(CH$_2$)$_{10}$ | Meta | Ovalbumin |
| —(CH$_2$)$_{10}$ | Meta | BSA |
| —(CH$_2$)$_{10}$ | Meta | Diptheria CRM$_{197}$ |
| —(CH$_2$)$_{10}$ | Meta | Tetanus toxoid |
| —O(CH$_2$) | Para | KLH |
| —O(CH$_2$) | Para | Ovalbumin |
| —O(CH$_2$) | Para | BSA |
| —O(CH$_2$) | Para | Diptheria CRM$_{197}$ |
| —O(CH$_2$) | Para | Tetanus toxoid |
| —O(CH$_2$) | Meta | KLH |
| —O(CH$_2$) | Meta | Ovalbumin |
| —O(CH$_2$) | Meta | BSA |
| —O(CH$_2$) | Meta | Diptheria CRM$_{197}$ |
| —O(CH$_2$) | Meta | Tetanus toxoid |
| —O(CH$_2$)$_2$ | Para | KLH |
| —O(CH$_2$)$_2$ | Para | Ovalbumin |
| —O(CH$_2$)$_2$ | Para | BSA |
| —O(CH$_2$)$_2$ | Para | Diptheria CRM$_{197}$ |
| —O(CH$_2$)$_2$ | Para | Tetanus toxoid |
| —O(CH$_2$)$_2$ | Meta | KLH |
| —O(CH$_2$)$_2$ | Meta | Ovalbumin |
| —O(CH$_2$)$_2$ | Meta | BSA |
| —O(CH$_2$)$_2$ | Meta | Diptheria CRM$_{197}$ |
| —O(CH$_2$)$_2$ | Meta | Tetanus toxoid |
| —O(CH$_2$)$_3$ | Para | KLH |
| —O(CH$_2$)$_3$ | Para | Ovalbumin |
| —O(CH$_2$)$_3$ | Para | BSA |
| —O(CH$_2$)$_3$ | Para | Diptheria CRM$_{197}$ |
| —O(CH$_2$)$_3$ | Para | Tetanus toxoid |
| —O(CH$_2$)$_3$ | Meta | KLH |
| —O(CH$_2$)$_3$ | Meta | Ovalbumin |
| —O(CH$_2$)$_3$ | Meta | BSA |
| —O(CH$_2$)$_3$ | Meta | Diptheria CRM$_{197}$ |
| —O(CH$_2$)$_3$ | Meta | Tetanus toxoid |
| —O(CH$_2$)$_4$ | Para | KLH |
| —O(CH$_2$)$_4$ | Para | Ovalbumin |
| —O(CH$_2$)$_4$ | Para | BSA |
| —O(CH$_2$)$_4$ | Para | Diptheria CRM$_{197}$ |
| —O(CH$_2$)$_4$ | Para | Tetanus toxoid |
| —O(CH$_2$)$_4$ | Meta | KLH |
| —O(CH$_2$)$_4$ | Meta | Ovalbumin |
| —O(CH$_2$)$_4$ | Meta | BSA |
| —O(CH$_2$)$_4$ | Meta | Diptheria CRM$_{197}$ |
| —O(CH$_2$)$_4$ | Meta | Tetanus toxoid |
| —O(CH$_2$)$_5$ | Para | KLH |
| —O(CH$_2$)$_5$ | Para | Ovalbumin |
| —O(CH$_2$)$_5$ | Para | BSA |

TABLE B-continued

| L Group | Position on Benzene Ring | Carrier |
|---|---|---|
| —O(CH$_2$)$_5$ | Para | Diptheria CRM$_{197}$ |
| —O(CH$_2$)$_5$ | Para | Tetanus toxoid |
| —O(CH$_2$)$_5$ | Meta | KLH |
| —O(CH$_2$)$_5$ | Meta | Ovalbumin |
| —O(CH$_2$)$_5$ | Meta | BSA |
| —O(CH$_2$)$_5$ | Meta | Diptheria CRM$_{197}$ |
| —O(CH$_2$)$_5$ | Meta | Tetanus toxoid |
| —O(CH$_2$)$_6$ | Para | KLH |
| —O(CH$_2$)$_6$ | Para | Ovalbumin |
| —O(CH$_2$)$_6$ | Para | BSA |
| —O(CH$_2$)$_6$ | Para | Diptheria CRM$_{197}$ |
| —O(CH$_2$)$_6$ | Para | Tetanus toxoid |
| —O(CH$_2$)$_6$ | Meta | KLH |
| —O(CH$_2$)$_6$ | Meta | Ovalbumin |
| —O(CH$_2$)$_6$ | Meta | BSA |
| —O(CH$_2$)$_6$ | Meta | Diptheria CRM$_{197}$ |
| —O(CH$_2$)$_6$ | Meta | Tetanus toxoid |
| —O(CH$_2$)$_7$ | Para | KLH |
| —O(CH$_2$)$_7$ | Para | Ovalbumin |
| —O(CH$_2$)$_7$ | Para | BSA |
| —O(CH$_2$)$_7$ | Para | Diptheria CRM$_{197}$ |
| —O(CH$_2$)$_7$ | Para | Tetanus toxoid |
| —O(CH$_2$)$_7$ | Meta | KLH |
| —O(CH$_2$)$_7$ | Meta | Ovalbumin |
| —O(CH$_2$)$_7$ | Meta | BSA |
| —O(CH$_2$)$_7$ | Meta | Diptheria CRM$_{197}$ |
| —O(CH$_2$)$_7$ | Meta | Tetanus toxoid |
| —O(CH$_2$)$_8$ | Para | KLH |
| —O(CH$_2$)$_8$ | Para | Ovalbumin |
| —O(CH$_2$)$_8$ | Para | BSA |
| —O(CH$_2$)$_8$ | Para | Diptheria CRM$_{197}$ |
| —O(CH$_2$)$_8$ | Para | Tetanus toxoid |
| —O(CH$_2$)$_8$ | Meta | KLH |
| —O(CH$_2$)$_8$ | Meta | Ovalbumin |
| —O(CH$_2$)$_8$ | Meta | BSA |
| —O(CH$_2$)$_8$ | Meta | Diptheria CRM$_{197}$ |
| —O(CH$_2$)$_8$ | Meta | Tetanus toxoid |
| —O(CH$_2$)$_9$ | Para | KLH |
| —O(CH$_2$)$_9$ | Para | Ovalbumin |
| —O(CH$_2$)$_9$ | Para | BSA |
| —O(CH$_2$)$_9$ | Para | Diptheria CRM$_{197}$ |
| —O(CH$_2$)$_9$ | Para | Tetanus toxoid |
| —O(CH$_2$)$_9$ | Meta | KLH |
| —O(CH$_2$)$_9$ | Meta | Ovalbumin |
| —O(CH$_2$)$_9$ | Meta | BSA |
| —O(CH$_2$)$_9$ | Meta | Diptheria CRM$_{197}$ |
| —O(CH$_2$)$_9$ | Meta | Tetanus toxoid |
| ‡ —X$_1$ | Para | KLH |
| ‡ —X$_1$ | Para | Ovalbumin |
| ‡ —X$_1$ | Para | BSA |
| ‡ —X$_1$ | Para | Diptheria CRM$_{197}$ |
| ‡ —X$_1$ | Para | Tetanus toxoid |
| ‡ —X$_1$ | Meta | KLH |
| ‡ —X$_1$ | Meta | Ovalbumin |
| ‡ —X$_1$ | Meta | BSA |
| ‡ —X$_1$ | Meta | Diptheria CRM$_{197}$ |
| ‡ —X$_1$ | Meta | Tetanus toxoid |
| ‡ —X$_2$ | Para | KLH |
| ‡ —X$_2$ | Para | Ovalbumin |
| ‡ —X$_2$ | Para | BSA |
| ‡ —X$_2$ | Para | Diptheria CRM$_{197}$ |
| ‡ —X$_2$ | Para | Tetanus toxoid |
| ‡ —X$_2$ | Meta | KLH |
| ‡ —X$_2$ | Meta | Ovalbumin |
| ‡ —X$_2$ | Meta | BSA |
| ‡ —X$_2$ | Meta | Diptheria CRM$_{197}$ |
| ‡ —X$_2$ | Meta | Tetanus toxoid |
| ‡ —X$_3$ | Para | KLH |
| ‡ —X$_3$ | Para | Ovalbumin |
| ‡ —X$_3$ | Para | BSA |
| ‡ —X$_3$ | Para | Diptheria CRM$_{197}$ |
| ‡ —X$_3$ | Para | Tetanus toxoid |
| ‡ —X$_3$ | Meta | KLH |
| ‡ —X$_3$ | Meta | Ovalbumin |
| ‡ —X$_3$ | Meta | BSA |
| ‡ —X$_3$ | Meta | Diptheria CRM$_{197}$ |
| ‡ —X$_3$ | Meta | Tetanus toxoid |
| ‡ —X$_4$ | Para | KLH |
| ‡ —X$_4$ | Para | Ovalbumin |
| ‡ —X$_4$ | Para | BSA |
| ‡ —X$_4$ | Para | Diptheria CRM$_{197}$ |
| ‡ —X$_4$ | Para | Tetanus toxoid |
| ‡ —X$_4$ | Meta | KLH |
| ‡ —X$_4$ | Meta | Ovalbumin |
| ‡ —X$_4$ | Meta | BSA |
| ‡ —X$_4$ | Meta | Diptheria CRM$_{197}$ |
| ‡ —X$_4$ | Meta | Tetanus toxoid |
| ‡ —X$_5$ | Para | KLH |
| ‡ —X$_5$ | Para | Ovalbumin |
| ‡ —X$_5$ | Para | BSA |
| ‡ —X$_5$ | Para | Diptheria CRM$_{197}$ |
| ‡ —X$_5$ | Para | Tetanus toxoid |
| ‡ —X$_5$ | Meta | KLH |
| ‡ —X$_5$ | Meta | Ovalbumin |
| ‡ —X$_5$ | Meta | BSA |
| ‡ —X$_5$ | Meta | Diptheria CRM$_{197}$ |
| ‡ —X$_5$ | Meta | Tetanus toxoid |
| ‡ —X$_6$ | Para | KLH |
| ‡ —X$_6$ | Para | Ovalbumin |
| ‡ —X$_6$ | Para | BSA |
| ‡ —X$_6$ | Para | Diptheria CRM$_{197}$ |
| ‡ —X$_6$ | Para | Tetanus toxoid |
| ‡ —X$_6$ | Meta | KLH |
| ‡ —X$_6$ | Meta | Ovalbumin |
| ‡ —X$_6$ | Meta | BSA |
| ‡ —X$_6$ | Meta | Diptheria CRM$_{197}$ |
| ‡ —X$_6$ | Meta | Tetanus toxoid |
| ‡ —X$_7$ | Para | KLH |
| ‡ —X$_7$ | Para | Ovalbumin |
| ‡ —X$_7$ | Para | BSA |
| ‡ —X$_7$ | Para | Diptheria CRM$_{197}$ |
| ‡ —X$_7$ | Para | Tetanus toxoid |
| ‡ —X$_7$ | Meta | KLH |
| ‡ —X$_7$ | Meta | Ovalbumin |
| ‡ —X$_7$ | Meta | BSA |
| ‡ —X$_7$ | Meta | Diptheria CRM$_{197}$ |
| ‡ —X$_7$ | Meta | Tetanus toxoid |
| ‡ —X$_8$ | Para | KLH |
| ‡ —X$_8$ | Para | Ovalbumin |
| ‡ —X$_8$ | Para | BSA |
| ‡ —X$_8$ | Para | Diptheria CRM$_{197}$ |
| ‡ —X$_8$ | Para | Tetanus toxoid |
| ‡ —X$_8$ | Meta | KLH |
| ‡ —X$_8$ | Meta | Ovalbumin |
| ‡ —X$_8$ | Meta | BSA |
| ‡ —X$_8$ | Meta | Diptheria CRM$_{197}$ |
| ‡ —X$_8$ | Meta | Tetanus toxoid |
| ‡ —X$_9$ | Para | KLH |
| ‡ —X$_9$ | Para | Ovalbumin |
| ‡ —X$_9$ | Para | BSA |
| ‡ —X$_9$ | Para | Diptheria CRM$_{197}$ |
| ‡ —X$_9$ | Para | Tetanus toxoid |
| ‡ —X$_9$ | Meta | KLH |
| ‡ —X$_9$ | Meta | Ovalbumin |
| ‡ —X$_9$ | Meta | BSA |
| ‡ —X$_9$ | Meta | Diptheria CRM$_{197}$ |
| ‡ —X$_9$ | Meta | Tetanus toxoid |
| ‡ —X$_{10}$ | Para | KLH |
| ‡ —X$_{10}$ | Para | Ovalbumin |
| ‡ —X$_{10}$ | Para | BSA |
| ‡ —X$_{10}$ | Para | Diptheria CRM$_{197}$ |
| ‡ —X$_{10}$ | Para | Tetanus toxoid |
| ‡ —X$_{10}$ | Meta | KLH |
| ‡ —X$_{10}$ | Meta | Ovalbumin |
| ‡ —X$_{10}$ | Meta | BSA |
| ‡ —X$_{10}$ | Meta | Diptheria CRM$_{197}$ |
| ‡ —X$_{10}$ | Meta | Tetanus toxoid |

‡ wherein X may be any atom selected from the group comprising C, O, N, P and S; including the appropriate number of hydrogens to balance charge.

III. Conjugation Chemistry

The compounds detailed in part (II) corresponding to formulas (I), (II), (III), and (IV) may be made by a variety of methods generally known in the art or as described herein.

Irrespective of the process utilized for conjugation of a hapten compound to a carrier molecule (X) via a linker (L), the process selected will typically result in a compound having a relatively high epitope density, i.e., the number of hapten compounds conjugated to a single carrier molecule, (X), as expressed above as n. The conjugation method used will depend upon the chemistry of coupling a particular hapten compound to a molecular carrier. In general, a reactive site on a first compound is linked to a reactive site on a second compound, using a coupling agent or catalyst. An exemplary process is described below in more detail.

Figure 34:
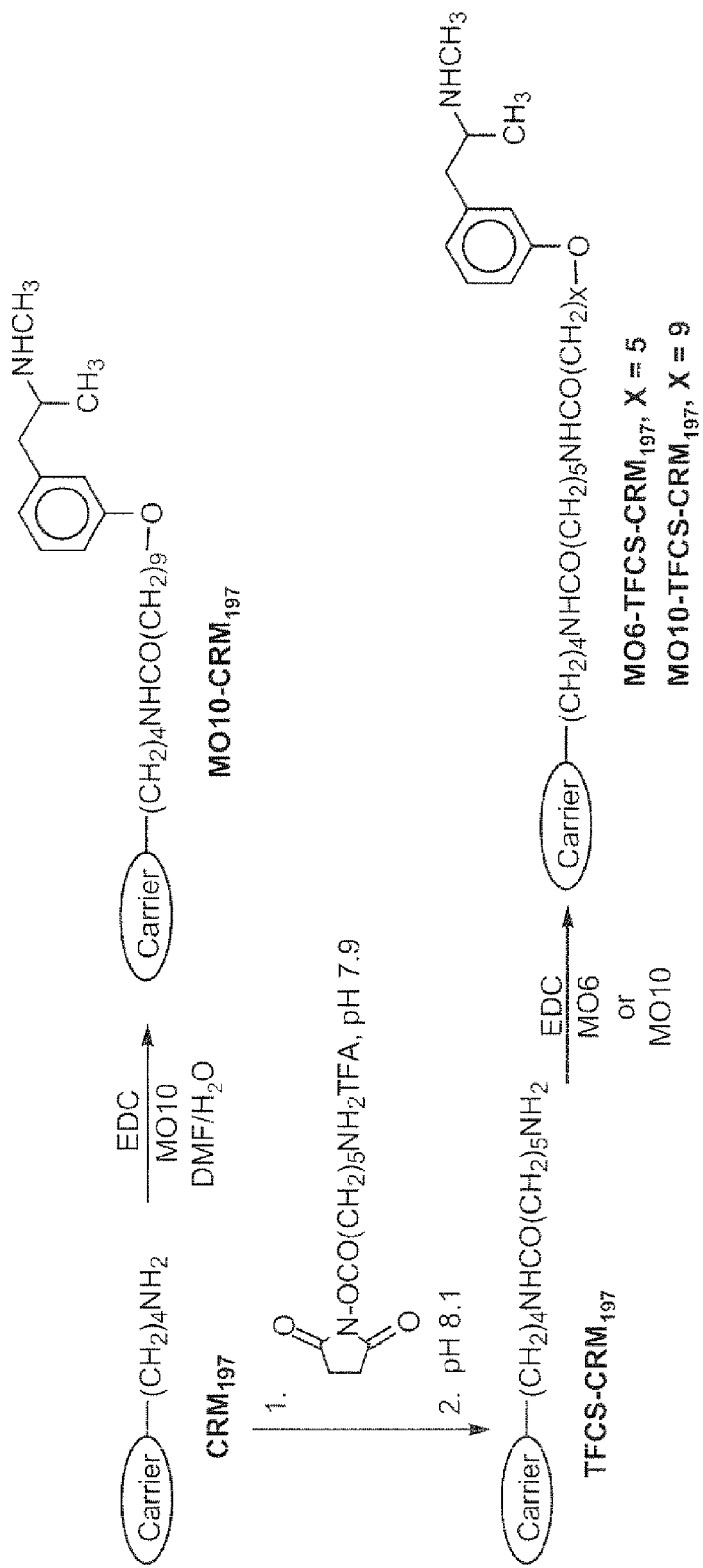
FIG. 34 presents a diagram illustrating a method of preparing a hapten conjugate with an amide-connection. The method comprises coupling of MO10 directly to $CRM_{197}$ using 1-ethyl-3-[3-dimethylaminopropyl]carbodiimide hydrochloride (EDC), or, to provide conjugates with different linkers, the conversion of $CRM_{197}$ to TFCS-$CRM_{197}$ by N-(ε-trifluoracetylcaproloxy)succinimide ester (TFCS), then coupling to MO6 and MO10 using EDC to give MO6-TFCS-$CRM_{197}$ or MO10-TFCS-$CRM_{197}$.

Referring to FIG. 34, in an exemplary embodiment to form compounds having formula (II) or (IV) the hapten compound may be conjugated via the linker (L) to a carrier molecule (X) by formation of an amide bond. Generally speaking, the carboxyl group of the linker is reacted with an amide group on the carrier molecule. However, in certain embodiments, the carboxyl group of the linker may be reacted with a second linker that is reacted with an amide group on the carrier molecule. Such second linkers may be homobifunctional or heterobifunctional linkers, and are well known in the art. Suitable coupling agents may include EDC, Carbodiimide-HCL, glutaraldehyde and other similar agents. In one embodiment, L of formula (II) or (III) may be conjugated to X by reaction with EDC (1-ethyl-3-[3-dimethylaminopropyl] carbodiimide hydrochloride) (see FIG. 34). Alternatively, X may be reacted with TFCS, and then reacted with EDC to form an amide bond with L of formula (II) or (IV) (see FIG. 34).

Typically, in a conjugation reaction that is based on an amide bond, the ratio of carrier molecule to hapten compound may be between about 1:25 and about 1:100. In one embodiment, the ratio may be between about 1:25 and about 1:50. In another embodiment, the ratio may be between about 1:50 and about 1:75. In yet another embodiment, the ratio may be between about 1:75 and about 1:100. In still another embodiment, the ratio may be between about 1:30 and about 1:90.

The ratio of carrier molecule to hapten compound should be selected to maximize the number of hapten compounds conjugated to the molecular carrier (i.e. n, as described in formulas (II) and (IV). Generally, n is an integer greater than or equal to 2. In one embodiment, n may be 3, 4, or 5. In another embodiment, n may be 6, 7, 8, or 9. In an exemplary embodiment, n is greater than or equal to 5. The ratio of carrier molecule to hapten compound may be determined by MALDI MS.

IV. Immunogenic Compositions Comprising Hapten Compounds

An additional aspect of the invention encompasses an immunogenic composition comprising a hapten compound. In some embodiments, the immunogenic composition may comprise a hapten compound selected from the group consisting of a compound of formula (I), a compound of formula (II), a compound of formula (III), and a compound of formula (IV). In one embodiment, the immunogenic composition may comprise a compound of formula (I). In another embodiment, the immunogenic composition may comprise a compound of formula (II). In yet another embodiment, the immunogenic composition may comprise a compound of formula (III). In still another embodiment, the immunogenic composition may comprise a compound of formula (IV).

In certain embodiments, an immunogenic composition comprising a hapten compound of the invention may further comprise an adjuvant. Generally speaking, an adjuvant may be used to increase the immune response to a hapten compound of the invention. For instance, an adjuvant may be used to increase antibody affinity, antibody titer, and the duration of the immune response in a subject. Non-limiting examples of adjuvants include alum, TiterMax Gold, Ribi, ASO4, Freund's complete adjuvant, and Freund's incomplete adjuvant. In one embodiment, the adjuvant may be alum. In another embodiment, the adjuvant may be TiterMax Gold. In yet another embodiment, the adjuvant may be Ribi. In still another embodiment, the adjuvant may be ASO4. In still yet another embodiment, the adjuvant may be Freund's complete adjuvant. In an additional embodiment, the adjuvant may be Freund's incomplete adjuvant. In an exemplary embodiment, the adjuvant is pharmaceutically acceptable for use in a human subject. Generally speaking, a pharmaceutically acceptable adjuvant is pyrogen free and will not induce anaphylactic shock in a subject. Non-limiting examples of pharmaceutically acceptable adjuvants for use in humans include alum and ASO4.

In some embodiments, an immunogenic composition comprising a hapten compound may further comprise a pharmaceutically acceptable carrier, as described in section II above. Briefly, a pharmaceutically acceptable carrier safely elicits an antibody response in a subject. In this context, safely means that the carrier does not substantially elicit an immune response that cross-reacts with a self-protein, or a regularly ingested protein of the subject. Those skilled in the art will recognize that the selection of a pharmaceutically acceptable carrier depends on large part on the subject that is administered the carrier.

In certain embodiments, it is envisioned that a particular molecular carrier may be conjugated to more than one type of hapten compound. For instance, a particular molecular carrier may be conjugated to a hapten compound of formula (II) and formula (IV). Alternatively, a particular molecular carrier may be conjugated to at least two hapten compounds listed in Table A.

In further embodiments, an immunogenic composition comprising a hapten compound may further comprise an adjuvant and a pharmaceutically acceptable carrier. In some embodiments, an immunogenic composition of the invention may comprise a combination of an adjuvant and carrier listed in Table C.

TABLE C

| Adjuvant | Carrier |
| --- | --- |
| Alum | Ovalbumin |
| Alum | BSA |
| Alum | KLH |
| Alum | Diptheria $CRM_{197}$ |
| Alum | Tetanus toxoid |
| Titermax gold | Ovalbumin |
| Titermax gold | BSA |
| Titermax gold | KLH |
| Titermax gold | Diptheria $CRM_{197}$ |
| Titermax gold | Tetanus toxoid |
| ASO4 | Ovalbumin |
| ASO4 | BSA |
| ASO4 | KLH |
| ASO4 | Diptheria $CRM_{197}$ |
| ASO4 | Tetanus toxoid |
| Ribi | Ovalbumin |
| Ribi | BSA |
| Ribi | KLH |
| Ribi | Diptheria $CRM_{197}$ |
| Ribi | Tetanus toxoid |
| Freund's complete adjuvant | Ovalbumin |
| Freund's complete adjuvant | BSA |
| Freund's complete adjuvant | KLH |
| Freund's complete adjuvant | Diptheria $CRM_{197}$ |
| Freund's complete adjuvant | Tetanus toxoid |
| Freund's incomplete adjuvant | Ovalbumin |
| Freund's incomplete adjuvant | BSA |

TABLE C-continued

| Adjuvant | Carrier |
| --- | --- |
| Freund's incomplete adjuvant | KLH |
| Freund's incomplete adjuvant | Diptheria $CRM_{197}$ |
| Freund's incomplete adjuvant | Tetanus toxoid |

In an alternative embodiment, an immunogenic composition comprising a hapten compound may further comprise a pharmaceutically acceptable excipient. Non-limiting examples of pharmaceutically acceptable excipients include sterile water, salt solutions such as saline, sodium phosphate, sodium chloride, alcohol, gum arabic, vegetable oils, benzyl alcohols, polyethylene glycol, gelatine, mannitol, carbohydrates, magnesium stearate, viscous paraffin, fatty acid esters, hydroxy methyl cellulose, and buffer. Other suitable excipients may be used by those skilled in that art.

V. Eliciting an Immune Response

Another additional aspect of the invention encompasses administering a hapten compound to a subject to elicit an immune response in the subject. Typically, such an immune response will generate specific antibodies that recognize one or more of (+) methamphetamine, (+)amphetamine, and (+)MDMA. In one embodiment, the specific antibodies may recognize two compounds from the group consisting of (+) methamphetamine, (+)amphetamine, and (+)MDMA. In an exemplary embodiment, the specific antibodies may recognize all three compounds of the group consisting of (+) methamphetamine, (+)amphetamine, and (+)MDMA. In another exemplary embodiment, the specific antibodies may recognize all three compounds of the group consisting of (+) methamphetamine, (+)amphetamine, and (+)MDMA, and not recognize (−) methamphetamine, (−)amphetamine, and (−)MDMA. In still another exemplary embodiment, the specific antibodies may recognize all three compounds of the group consisting of (+) methamphetamine, (+)amphetamine, and (+)MDMA, and not recognize over the counter medications.

In one embodiment, the elicited immune response may generate antibodies specific for a compound administered to a subject. In certain embodiments, a method for generating specific antibodies for a compound selected from the group consisting of a compound of formula (I), a compound of formula (II), a compound of formula (III), and a compound of formula (IV), may comprise administering the compound to a subject. In another embodiment, the elicited immune response may generate antibodies specific for more than one hapten compound of the invention administered to a subject. For instance, a compound of formula (II) and a compound of formula (IV) may be administered to a subject simultaneously in the same composition, contemporaneously in separate compositions, or sequentially. Alternatively, more than one compound listed in Table A may be administered to a subject simultaneously, contemporaneously, or sequentially.

As used herein, subject refers to any vertebrate capable of mounting an immune response. In one embodiment, a subject may be a rodent. Non-limiting examples of rodents include mice and rats. In another embodiment, a subject may be a livestock animal. Non-limiting examples of livestock animals include cows, pigs, sheep, goats, llamas, and poultry. In still another embodiment, a subject may be a companion animal. Non-limiting examples of companion animals include dogs, cats, rabbits, and horses. In an additional embodiment, a subject may be a primate. Non-limiting examples of primates include lemurs, monkeys, apes, and humans. In a further embodiment, a subject may be a non-human primate. In an alternative embodiment, a subject may be human.

In each of the above embodiments, the subjects may be subjects addicted to (+) methamphetamine, (+)amphetamine, and (+)MDMA (and/or ecstasy). Alternatively, the subjects may be at risk for addiction to (+) methamphetamine, (+)amphetamine, and (+)MDMA (and/or ecstasy). In another alternative, the subjects may be recovering addicts to (+) methamphetamine, (+)amphetamine, and (+)MDMA (and/or ecstasy).

One skilled in the art will appreciate that a hapten compound of the invention may be administered in a variety of ways to elicit an immune response. (See generally, Herbert and Fristensen (1986) and Poole (1987).) Generally speaking, the method of administration will depend on the volume of the composition administered, the solubility of the composition, and on the speed of the immune response desired. Moreover, the method of administration may be limited by the subject involved. Typically, a method of administration should be chosen that provides increased antibody titer, affinity, and duration of antibody response. Non-limiting examples of possible administration methods include subcutaneous administration, intraperitoneal administration, intravenous administration, intramuscular administration and intradermal administration. In one embodiment, a composition comprising a hapten compound of the invention may be administered subcutaneously. In another embodiment, a composition may be administered intraperitoneally. In yet another embodiment, a composition may be administered intravenously. In still another embodiment, a composition may be administered intramuscularly. In still yet another embodiment, a composition may be administered intradermally.

The dosage of hapten compound administered will typically vary with the subject involved. Generally speaking, in formulating a dosage to be administered, one skilled in the art should consider the weight of the subject and the method of administration. Moreover, the dosage may be chosen to increase antibody titer, antibody affinity, and/or duration of antibody response. For instance, a high dosage may lead to higher titer antibodies, but lower affinity antibodies. In one embodiment, the dosage used may be the lowest dosage possible to generate an antibody response in at least 70% of the subjects involved. In another embodiment, the dosage used may be the lowest dosage possible to generate an antibody response in at least 75%, 80%, 85%, or 90% of the subjects involved. In yet another embodiment, the dosage used may be the lowest dosage possible to generate an antibody response in at least 91%, 92%, 93%, 94%, 95%, 96%, 97%, 98%, or 99% of the subjects involved. In still yet another embodiment, the dosage used may be the lowest dosage possible to generate an antibody response in 100% of the subjects involved. Non-limiting examples of specific dosages for various subjects may be found in the examples.

The schedule of administration should also, generally speaking, be chosen to increase antibody titer, antibody affinity, and the duration of immune response. For instance, a subject might be initially administered a hapten compound of the invention, and then receive booster administrations thereafter. The frequency and number of booster administrations can and will vary with the subject involved. Frequent administrations may increase titer, but not affinity. Alternatively, less frequent administrations may result in increased affinity. For instance, in humans, a schedule may include booster administrations for one or more years following the initial administration. Non-limiting examples of booster schedules may be found in the examples.

VI. Uses for the Specific Antibodies

A further aspect of the invention encompasses both therapeutic and non-therapeutic uses for the specific antibodies generated using the methods of section V above.

In certain embodiments, the specific antibodies may be used in non-therapeutic assays, such as immunostaining, immunoprecipitation, immunoblotting, immunoaffinity purification, and ELISAs. In one embodiment, the specific antibodies may be used for immunostaining. In another embodiment, the specific antibodies may be used for immunoprecipitation. In yet another embodiment, the specific antibodies may be used for immunoblotting. In still another embodiment, the specific antibodies may be used for immunoaffinity purification. In still yet another embodiment, the specific antibodies may be used for ELISAs. Protocols for each of the above non-therapeutic uses are well known in the art, and may be found, for instance, in Harlow and Lane, *Antibodies*, Cold Spring Harbor, 1988, Chapters 9-14.

Additionally, the specific antibodies may be used for therapeutic purposes. Generally speaking, the specific antibodies may be used to antagonize the effects of (+) methamphetamine, (+)amphetamine, and/or (+)MDMA in a subject. In certain embodiments, the subjects may be addicted to (+) methamphetamine, (+)amphetamine, and/or (+)MDMA. For instance, in one embodiment, the specific antibodies may antagonize the effects of (+) methamphetamine, (+)amphetamine, and/or (+)MDMA in a subject by decreasing the concentration of (+)methamphetamine, (+)amphetamine, or (+)MDMA in the brain of a subject. In another embodiment, the specific antibodies may be used to decrease drug-seeking behavior in a subject. In yet another embodiment, the specific antibodies may be used to decrease self-dosing behavior in a subject.

In each of the above embodiments, the specific antibodies may be administered passively, actively, or in a combination of passive and active administration. Active administration typically refers to administering a hapten compound of the invention to a subject so as the subject generates antibodies in vivo. Passive administration typically refers to administering at least one specific antibody, generated by a subject or produced via ex vivo methods, into a second subject.

In one embodiment, the invention may encompass a method of treating drug addiction. The method may comprise eliciting an immune response in a drug-addicted subject by administering a hapten composition to a subject, wherein the immune response decreases the concentration of (+)methamphetamine, (+)amphetamine, or (+)MDMA in the brain of the subject.

Definitions

To facilitate understanding of the invention, a number of terms are defined below:

As used herein "(d)" stands for dextrorotatory and (l) stands for levorotatory, and refers to the direction in which an enantiomer rotates the plane of polarized light. Herein, (d) is used interchangeably with (+), and (l) is used interchangeably with (−).

Unless otherwise indicated, the alkyl groups described herein are preferably lower alkyl containing from one to eight carbon atoms in the principal chain and up to 30 carbon atoms or more. They may be straight or branched chain or cyclic and include methyl, ethyl, propyl, isopropyl, butyl, hexyl and the like. Unless otherwise indicated, the alkenyl groups described herein are preferably lower alkenyl containing from two to eight carbon atoms in the principal chain and up to 30 carbon atoms or more. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 30 carbon atoms or more. They may be straight or branched chain and include ethynyl, propynyl, butynyl, isobutynyl, hexynyl, and the like.

As used herein, antibody generally means a polypeptide or protein that recognizes and can bind to an epitope of an antigen. An antibody, as used herein, may be a complete antibody as understood in the art, i.e., consisting of two heavy chains and two light chains, or be selected from a group comprising polyclonal antibodies, ascites, Fab fragments, Fab' fragments, monoclonal antibodies, chimeric antibodies, humanized antibodies, human antibodies, and a peptide comprising a hypervariable and/or framework region of an antibody.

As used herein, antibody affinity refers to the attraction between and antibody and a target epitope. Affinity may be measured by calculating a $K_D$ value for a particular antibody and a particular epitope. Typically, affinity can be equated with $(1/K_D)$ "$K_D$" as used herein, refers to disassociation constant. Methods of calculating $K_D$ values are well known in the art.

As used herein, antibody titer refers to the concentration of antibodies present in the highest dilution of a serum sample at which visible clumps with an appropriate antigen are formed. Titer may be measured using an ELISA or RIA assay, by methods commonly known in the art.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "conjugate" refers to a substance formed from the joining together of two parts. Representative conjugates in accordance with the present invention include those formed by the joining together of a small molecule and a large molecule, such as a protein. Methamphetamine attached to a carrier protein via a linker is an example of conjugation.

The term "contiguous" is used herein to describe the number of atoms forming a linker. The number of atoms in a linking group or linker is determined by counting the contiguous atoms other than hydrogen. In this context, "contiguous" is the number of atoms in a chain within a linking group determined by counting the number of atoms other than hydrogen along the shortest route between the substructures being connected.

The term "derivative" refers to a chemical compound or molecule made from a parent compound by one or more chemical reactions.

The term "hapten" refers to a partial or incomplete antigen. Haptens are protein-free substances that generally are not capable of stimulating antibody formation, but may react with antibodies. Amphetamine, methamphetamine, and their derivatives are haptens.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring.

The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo groups include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl.

As used herein, a "linking group" or "linker" refers to a portion of a chemical structure that connects two or more substructures such as haptens, carriers, immunogens, labels, tracers or other linkers. A linking group has at least 1 uninterrupted chain of atoms other than hydrogen (or other monovalent atoms) extending between the substructures. The atoms of a linking group and the atoms of a chain within a linking group are themselves connected by chemical bonds. Linkers may be straight or branched, saturated or unsaturated, hydrocarbyl or substituted hydrocarbyl chains.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents may include one or more of the following groups: halogen, carbocycle, carboxy, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various embodiments of the invention.

Example 1

Protocol for Generation of High Affinity Monoclonal Antibodies and Fab Fragments that Bind to D-Methamphetamine and Other Stimulant Drugs.

The haptens are coupled to a bovine serum albumin antigen by using a general synthesis procedure (Minh-Tam et al., 1981). This two-step, modified carbodiimide procedure permits a defined number of haptens to be covalently bound to the protein in a controlled molecular orientation. It also minimizes cross linking of protein molecules and the unwanted conjugation of the haptens through the free amino group on the d-methamphetamine haptens. A complimentary ovalbumin-d-methamphetamine hapten was also generated for use in screening hybridoma products in an enzyme-linked immunosorbent assay (ELISA). This general synthesis procedure has been used in the past to generate anti-drug antibodies (Owens et al., 1988) and anti-peptide antibodies (Laurenzana et al., 1995).

For the production of monoclonal antibodies, BALB/c mice (n=6-10 per hapten) are immunized with 100 µg of the BSA-d-methamphetamine, emulsified in an equal volume of an adjuvant (e.g., Titer Max, RIBI, Freund's Complete Adjuvant). One month later the animals were boosted with the same reagents and two weeks later the serum was tested for specific antibodies using the ovalbumin-d-methamphetamine conjugates in an ELISA. The spleen from the animal with the highest titer of anti-d-methamphetamine antiserum was used for the first fusion. The other animals were boosted every three to four weeks to maintain titers of anti-d-methamphetamine in anticipation of future immunizations. After fusion of spleen cells from the mice with a myeloma cell line, hybridomas secreting anti-d-methamphetamine antibodies were identified using an ELISA with the appropriate ovalbumin-d-methamphetamine conjugate as described (Laurenzana et al., 1995).

Wells with a positive reaction to d-methamphetamine were subcloned to monoclonality. For specificity determinations, the antibodies were tested in an ELISA format using a series of ligands. These ligands include (but are not limited to) d- and l-methamphetamine, d- and l-amphetamine, MDMA, MDA, ephedrine, pseudoephedrine, and other potentially cross reacting stimulant-like molecules and endogenous neurotransmitters. Antibodies specific for the d-isomers and having a low $K_D$ value (e.g., <1-30 nM) were selected. Although a range of antibody affinities (as great as 250 nM) has been studied, the objective was to have affinity constants for methamphetamine in the range of 1-30 nM.

Once an anti-d-methamphetamine secreting hybridoma was chosen, large quantities of the antibody were produced in a hollow fiber bioreactor (Valentine and Owens, 1996). A representative method for the monoclonal antibody purification process is as follows. Monoclonal antibody-containing tissue culture media was combined and concentrated to one-tenth of the original volume using an Amicon spiral cartridge concentration system. This technique takes approximately 10 minutes to concentrate 2 L down to 100-200 ml. The procedure recovers 95% of the monoclonal antibody and removes >95% of the bovine albumin in the media. The concentrated monoclonal antibody was dialyzed against 50 mM MES buffer (2-(N-Morpholino)-ethanesulfonic acid), pH 6.0 for further purification using a large, glass chromatography column packed with 1 L of SP-Sepharose Big Bead media (Pharmacia LKB Biotechnology). The sample was loaded on the column and washed with the MES buffer to remove non-specifically bound proteins. The monoclonal antibody was eluted in one step using 50 mM MES/0.15 M NaCl. This elution also serves to reconcentrate the monoclonal antibody. The purity and concentration of the purified anti-d-methamphetamine monoclonal antibody were determined by SDS-PAGE and spectrophotometry respectively.

Fab fragments of the monoclonal antibody were produced by the papain digestion method described by Coding (1983) using an mAb:papain ratio of 500:1 (w/w). After digestion, the Fab was purified using a HPLC column containing Pharmacia Streamline DEAE Sepharose anion exchange media. Purity was checked by SDS-PAGE and the protein concentration was measured with a Coomassie protein assay or spectrophotometrically. For every 100 g of monoclonal antibody, one may expect to yield at least 55-68 g of Fab fragments. For use in animals, the Fab and monoclonal antibody were dialyzed against PBS, pH 7.4 and concentrated with an Amicon ultrafiltration device to 50-100 mg/ml (depending on the needs of the in vivo testing procedure). Both Fab and monoclonal antibody were stored at −80° C. until needed. There was no decrease in binding activity or solubility after long-term storage of the monoclonal antibody or Fab.

Example 2

Protocol for the Synthesis of Hapten Compounds

The methamphetamine-like stimulants that are most often abused are methamphetamine, amphetamine and MDMA (FIG. 3). Based on review of the literature on anti-methamphetamine antibodies (e.g., Faraj et al., 1976; Usagawa et al., 1989; Ward et al., 1994) and analysis of the molecular features of the molecules shown in FIG. 3, it is hypothesized that coupling of a spacer group (with a carboxylic acid terminus) at the para or meta position of the aromatic ring structure will offer the best chance for generating a class-specific antibody. The resulting antibodies are expected to react best with the parent compound, as opposed to metabolites, and would also be less likely to significantly cross react with natural neurotransmitters. If the protein was coupled to the amine groups at the other end of the molecule (which would be more convenient), this would not generate antibodies that would cross react with MDMA. The haptens designed for generating antibodies specific for methamphetamine-like stimulants are illustrated in FIGS. 4A-4C.

Figure 5:
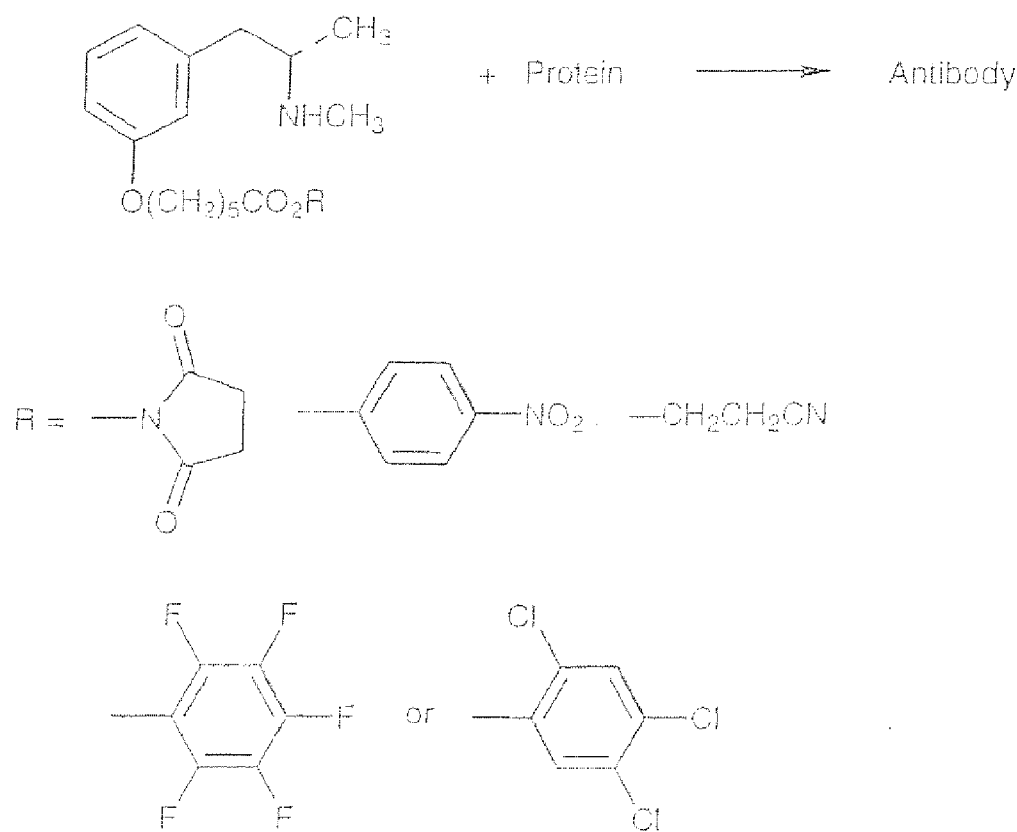
FIG. 5 shows a method of using activated ester to couple the hapten to a protein to make the antibody. Similar chemistry would apply to all other structures shown in FIGS. 4A-4C.

A method of using activated ester to couple the hapten to a protein to make the antibody is shown in FIG. 5. Similar chemistry would apply to all other structures shown in FIGS. 4A-4C.

Figure 6:
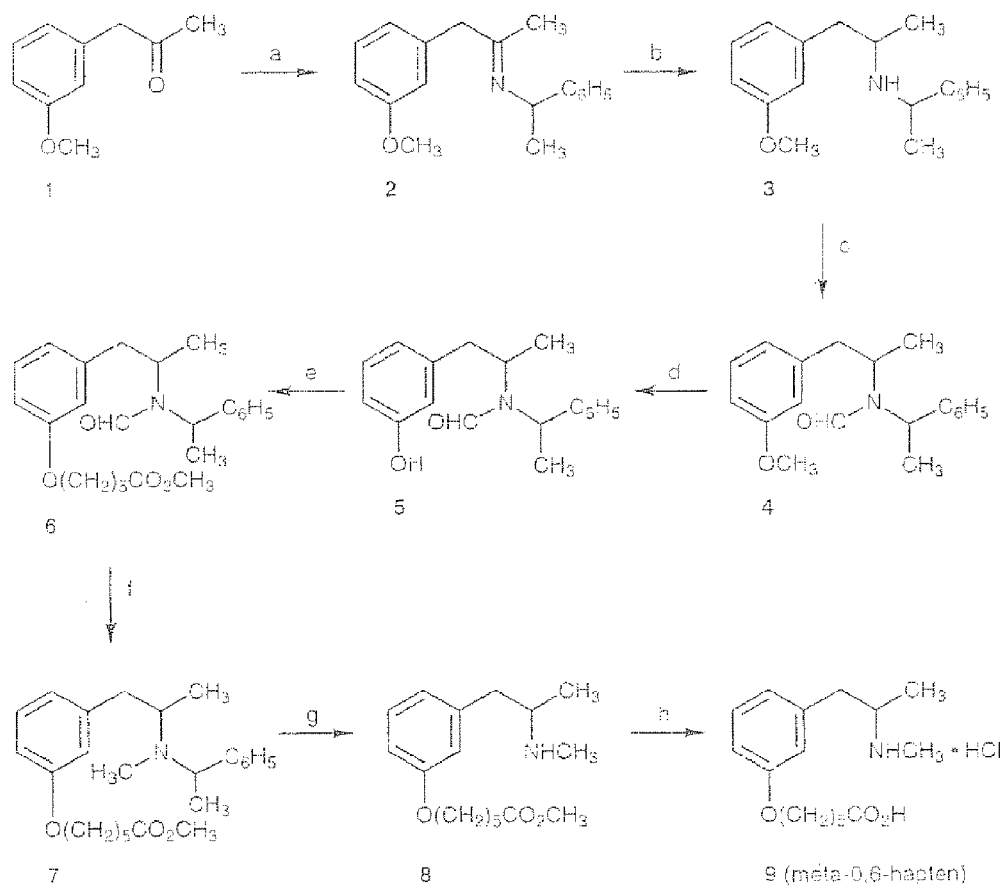
FIG. 6 shows the scheme of synthesis for 3-(5'-carboxypentyloxy)methamphetamine hydrochloride.

The synthesis of one of the haptens (hapten 1 in FIG. 4A with X=5 and connected at the 3-position) is outlined in FIG. 6. The goal is to prepare the (S)-(+)-isomer of 3-(5'-carboxypentyloxy)methamphetamine (compound 9 of FIG. 6). To establish the feasibility of the synthetic methods, the synthesis of (R)-(−)-9 is presented. Those skilled in the art will know that (S)-(+)-9 can be prepared using the same method starting with (S)-α-methylbenzylamine.

Thus, to prepare (R)-9,3-methoxyphenylacetone (compound 1 of FIG. 6) was condensed with (R)-α-methylbenzylamine to give compound 2. Raney nickel reduction of compound 2 followed by separation provided the pure (R,R)-diastereoisomer of compound 3. The N-formyl-protected intermediate compound 4 was obtained by treating compound 3 with a formic acid-acetic anhydride mixture. O-Demethylation of compound 4 using boron tribromide yielded the phenol compound 5. Alkylation of compound 5 with methyl 6-bromohexanoate afforded compound 6. Reduction of compound 6 using diborane provided the N—CH$_3$ intermediate compound 7, which yielded compound 8 on reduction using palladium on carbon catalyst in refluxing formic acid. The desired final optically pure hapten compound 9 as the hydrochloride salt was obtained by treating compound 8 with dilute hydrochloric acid.

Example 3

Synthesis of the Intermediate Compound (R,R)—N-α-Methylbenzyl-3-Methoxyamphetamine Hydrochloride A solution of 3-methoxyphenylacetone (10 g, 0.061 mol) and (R)-α-methylbenzylamine (7.38 g, 0.061 mol) in 100 mL of dry toluene was heated to reflux in a flask fitted with a Dean-Stark condenser for 20 h. After cooling the reaction mixture, the solvent was removed, and the residue was dried under vacuum. The residual oil was dissolved in absolute EtOH (60 mL), and a slurry of EtOH washed Raney nickel was added. The resulting mixture was hydrogenated for 96 h at 40 psi hydrogen. The catalyst was removed by filtration over a Celite bed, and the filtrate was treated with HCl gas. Evaporation of the solvent gave a white solid which was triturated with hot acetone to provide the target compound 3 of FIG. 6 as a white solid. An analytical sample was prepared from an aliquot removed. The sample recrystallized from MeOH/diethyl ether had mp 215-218° C.; [a]$^{21}$D (17.85°, c 1.95, MeOH). $^1$H NMR (CD$_3$OD) δ 1.17 (d, 3H), 1.69 (d, 3H), 2.53 (dd, 1H), 3.17 (m, 1H), 3.31 (m, 1H), 3.74 (s, 3H), 4.63 (q, 1H), 6.59 (s, 1H), 6.62 (d, 1H), 6.82 (d, 1H), 7.21 (t, 1H), 7.54 (m, 5H). Elemental analysis: calcd. for C$_{18}$H$_{23}$NO.HCl: C, 70.69; H, 7.91; N, 4.58; Cl, 11.59. Found: C, 70.51; H, 7.99; N, 4.53; Cl, 11.65.

Example 4

Synthesis of the Intermediate Compound (R,R)—N-formyl-N-α-methylbenzyl-3-methoxyamphetamine To a stirred solution of formic acid (7.5 mL, 0.2 mol) at 0° C. was added acetic anhydride (18.9 mL, 0.2 mol) dropwise. After 30 min, the amine compound 3 of FIG. 6 (3.9 g, 13.7 mmol) in a minimum volume of formic acid was added, and the mixture was stirred overnight. Water was carefully added, and the mixture was neutralized with dilute NH$_4$OH. The mixture was extracted with CH$_2$Cl$_2$, washed with saturated sodium chloride solution, and dried over NaSO$_4$. The residue obtained after evaporation was purified on a silica gel column eluting with a solvent mixture of hexane/CH$_2$Cl$_2$/CH$_3$OH (5:14:1) to give 3.83 g (94%) of compound 4 of FIG. 6 as a white solid.

Example 5

Synthesis of the Intermediate Compound (R,R)—N-formyl-N-α-methylbenzyl-3-hydroxy amphetamine To a stirred solution of compound 4 of FIG. 6 (2.85 g, 10 mmol) in CH$_2$Cl$_2$ (30 mL) was added a solution of BBr$_3$ (4.84 g, 20 mmol) in 50 mL of CH$_2$Cl$_2$. After stirring overnight, the excess of BBr$_3$ was quenched by careful addition of water and the organic fraction separated. The aqueous layer was further extracted with CH$_2$Cl$_2$, and the combined CH$_2$Cl$_2$ fraction was dried over Na$_2$SO$_4$. Evaporation gave 2.01 g (74%) of compound 5 of FIG. 6 as a white solid. Further purification on a silica gel column eluting with hexane/CH$_2$Cl$_2$/MeOH (4:8: 1) gave 1.65 g (61%) pure product. The analytical sample was triturated with ether to give white crystals; mp 174-177° C.

Elemental analysis: calcd. for C$_{18}$H$_{21}$NO$_2$.1.25 H$_2$O: C, 75.69; H, 7.50; N, 4.91. Found: C, 75.67; H, 7.46; N, 5.00.

Example 6

Synthesis of the Intermediate Compound (R)-3-(5'-carbomethoxypentyloxy) methamphetamine To a suspension of hexane washed sodium hydride (216 mg, 4.32 mmol) in 5 mL of DMF was added a solution of (R,R)-3-hydroxyphenyl-2-propyl-N-formamido-N-α-methylbenzylamine (compound 5 of FIG. 6) (1.22 g, 4.32 mmol). After stirring for 30 min at room temperature, a solution of methyl 6-bromohexanoate (1.36 g, 6.48 mmol) in DMF (3 mL) was added and stirred overnight at room temperature. The reaction mixture was diluted with H$_2$O (50 mL) and extracted with methylene chloride (3×10 mL). The combined organic fraction was washed with saturated sodium chloride solution and dried over Na$_2$SO$_4$. After removal of the solvent, the residue was purified on a silica gel column. Eluting with a solvent mixture (CH$_2$Cl$_2$:hexane:MeOH, 4:14:1) to give 1.68 g (95%) of compound 6 of FIG. 6. $^1$H NMR (CDCl$_3$) δ1.28 (dd, 3H), 1.53 (m, 2H), 1.58 (dd, 3H), 1.72 (m, 4H), 2.36 (m, 2H), 2.41 (m, 1H), 2.89 (m, 1H), 3.25 (m, 1H), 3.41 (t, 2H), 3.68 (s, 3H), 3.82 (q, 2H), 4.58, 6.07 (2 q, 1H), 6.17, 6.67 (2 s, 1H), 6.57, 6.40 (2d, 1H), 6.67 (dd, 1H), 7.05 (dd, 1H), 7.36 (m, 5H), 8.41, and 8.48 (two s, 1H). The sample was used in the next step without further characterization.

A solution of the above formamide compound 6 of FIG. 6 (1.63 g) was treated with BH$_3$.THF (10 mL) and stirred for 30 min when the excess of BH$_3$ was decomposed with MeOH followed by dilute HCl. The reaction mixture was basified with dilute NH$_4$OH and extracted with methylene chloride (3×25 mL). The organic fraction was dried over Na$_2$SO$_4$ and evaporated to dryness. The oily material was dissolved in MeOH (25 mL), and Pd/C (250 mg) was added. The mixture was heated to reflux with formic acid (3 mL in three portions) for an hour. The filtrate, obtained after removal of the catalyst, was evaporated and the resulting residue purified on a silica gel column. Elution with 10% MeOH in methylene chloride gave 0.84 g (70% overall in two steps) of a clear oil compound 8. $^1$H NMR (CDCl$_3$) 1.06 (d, 3H), 1.50 (m, 2H), 1.71 (m, 2H), 1.80 (m, 2H), 2.33 (t, 2H), 2.41 (s, 3H), 3.67 (s, 3H), 3.95 (t, 2H), 6.75 (m, 3H), 7.19 (m, 1H). The sample was converted to HCl salt; mp 53-57° C. Elemental analysis: calcd. for C$_{17}$H$_{27}$NO$_3$.HCl.0.75 H$_2$O: C, 59.50; H, 8.50; N, 4.10. Found: C, 59.65; H, 8.45; N, 4.21.

Example 7

Synthesis of Intermediate (R)-3-(5'-carboxypentyloxy) methamphetamine hydrochloride A solution of compound 8 of FIG. 6 (400 mg, 1.15 mmol) in dilute hydrochloric acid (6N, 5 mL) was heated to reflux for 4 h. The reaction was evaporated to dryness, and the residue was crystallized from MeOH/ether to give 215 mg (59%) of an off-white crystalline material: mp 73-77° C. $^1$H NMR (CD$_3$OD) 1.25 (d, 3H), 1.34 (m, 2H), 1.40 (m, 2H), 1.67 (m, 2H), 2.65 (t, 2H), 2.72 (s, 3H), 4.22 (m, 2H), 6.73 (m, 3), 7.13 (s, 1H). Elemental Analysis: calcd. for C$_{16}$H$_{25}$NO$_3$.HCl.0.25 H$_2$O: C, 59.99; H, 8.34; N, 4.37; Cl, 11.07. Found: C, 60.09; H, 8.33; N, 4.37; Cl, 11.13.

Example 8

Effect of Hapten Design on Antibody Specificity for D-Methamphetamine Like Drugs In these experiments, rabbit antiserum was generated against two unique d-methamphetamine like haptens. Each hapten included the basic chemical structure of d-methamphetamine, along with a new chemical linker group attached at the para (para-O,6 hapten) or meta (meta-O,6 hapten) positions of the aromatic ring structure (see Table 3 herein). The distal end of this linker group had a carboxy terminus for use in forming a peptide bond with protein antigens. After synthesis of a hapten-bovine serum albumin conjugate, this antigen was used for immunizing two rabbits. The first immunization for each rabbit was with 200 μg of either para-O,6 antigen or meta-O,6 antigen in Freund's complete adjuvant. The first booster immunization was with 100 μg of antigen in Freund's incomplete adjuvant. Seven to ten days later each animal was bled and the serum was collected for testing.

After titering each antiserum for selection of an appropriate serum dilution for radioimmunoassay, the relative cross-reactivity of each antiserum was determined. In this assay, a constant dilution of antiserum and a constant amount of [$^3$H]-methamphetamine was added to each test tube. Next, increasing amounts of either d-amphetamine or d-methamphetamine were added to separate tubes. After an overnight incubation at 4-8° C., the antibody bound [$^3$H]-methamphetamine was separated from the free [$^3$H]-methamphetamine using a goat anti-rabbit second antibody. The antibody precipitate in each tube was then transferred to a scintillation vial and the amount of radioactivity in each tube was determined by liquid scintillation spectrometry. For each of the test drugs (either d-amphetamine or d-methamphetamine), the ED$_{50}$ value for inhibition of [$^3$H]-methamphetamine binding to each antiserum was determined using a sigmoidal (logistic) fit to the percentage of [$^3$H]-methamphetamine binding versus log ligand dose.

Figure 7:
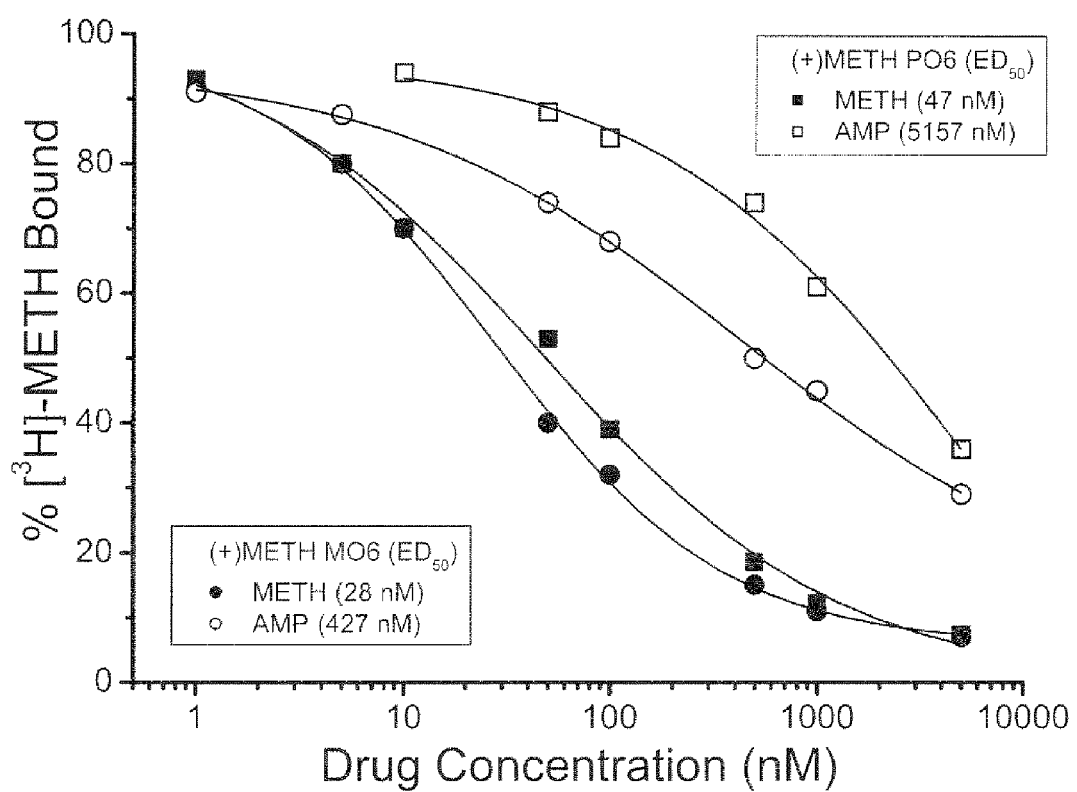
FIG. 7 shows radioimmunoassay cross-reactivity studies. The two dose response curves with squares for symbols show antiserum generated from immunization of two different rabbits with a (+)METH PO6 hapten (hapten 10 in FIG. 4A with X=5 and connected at the 4 position). The two curves with circles for symbols show antiserum generated from immunization with a (+)METH MO6 hapten (hapten 10 in FIG. 4A with X=5 and connected at the 3 position). The inhibition of [$^3$H]-methamphetamine binding for both antiserum was tested using both (+)amphetamine and (+)methamphetamine. These data show that careful hapten design can lead to antiserum that has significant cross-reactivity with both (+)amphetamine and (+)methamphetamine.

Results from these studies show that the antiserum generated from the para-O,6 hapten (right two dose-response curves, FIG. 7) is significantly more specific for d-methamphetamine (ED$_{50}$=427 nM) than it is for d-amphetamine (ED$_{50}$=5157 nM). Indeed the relative cross reactivity for d-amphetamine is only 8.3% (427 nM/5157 nM×100%) of the value for d-methamphetamine. Thus, while this hapten might be useful in developing a highly specific assay for detection of d-methamphetamine, it would not be useful in generating a monoclonal antibody-based medication with high affinity and broad recognition for d-amphetamine like drugs.

In contrast, results from the radioimmunoassay analysis of the meta-O,6 antiserum (left two dose-response curves, FIG. 7) showed d-amphetamine (ED$_{50}$=47 nM) cross-reactivity is 59.6% (28 nM/47 nM×100%) of the value for d-methamphetamine (ED$_{50}$=28 nM). In these studies the meta-O,6 hapten also generated higher affinity antiserum than the para-O,6 hapten, as determined from the significantly lower ED$_{50}$ values for both d-amphetamine and d-methamphetamine. As an object of this invention is to generate a widely cross-reacting antiserum for d-amphetamine-like drugs, these data reflect the importance of the hapten design on antibody specificity.

Example 9

Comparison of Protocols for Active and Passive Immunization as Treatments for D-Methamphetamine Addiction A series of male Sprague-Dawley rats are immunized with a d-methamphetamine-like hapten until high titers are achieved, or treated with anti-d-methamphetamine mAb. The rats are then repeatedly challenged with i.v. d-methamphetamine over several weeks. The ability of the antibodies to antagonize drug effects over an extended time period is assessed by behavioral measurements of response and using d-methamphetamine dose-response curves with dosing schedules that are designed to simulate repeated binge use of the drug. The rats for all of these studies are purchased with indwelling jugular venous catheters for i.v. administration of d-methamphetamine and anti-d-methamphetamine mAb.

For active immunization, one group of rats (n=6 for all groups) is immunized over a six week period prior to the start of the studies. An example immunization plan is 100 μg of the BSA-d-methamphetamine, emulsified in an equal volume of Titer-Max as adjuvant, followed at weeks 3 and 6 by a booster immunization. Ten days after the last boost, the anti-d-methamphetamine serum titers are checked in an ELISA. If the titers are elevated, behavioral testing begins on day 10-14 after the last boost.

For passive immunization, another group of rats is treated with 400 mg dose of monoclonal antibody the day before the start of the study. This dose of anti-d-methamphetamine monoclonal antibody (400 mg) should have the capacity to bind up to 2.1 mg/kg of d-methamphetamine on day 1 of the behavioral experiments, and up to 0.52 mg/kg of d-methamphetamine on day 16 (the final day of testing). A 2.1 mg/kg dose of d-methamphetamine in the rat would be about equivalent to a 150 mg binge use of d-methamphetamine in an average size human (i.e., about 150 lbs). The calculation of the d-methamphetamine (M.W. 149 g/mol) mol-eq dose of IgG assumes a 350 g rat, two IgG binding sites, a mass of 150,000 kDa, an in vivo first-order monoexponential loss of the IgG, and an IgG $t_{1/2}$ of 8.1 days (Bazin-Redureau et al., 1997).

The effectiveness of each therapy is measured by accessing the cumulative behavioral effects after administration of a range of d-methamphetamine doses over a 3 hr time period. This d-methamphetamine dosing strategy is used to simulate binge drug use and an addict's attempt to surmount the blocking effects of the antagonist by self-administration of progressively higher doses. The i.v. doses of 0.1, 0.3 and 1.0 mg/kg are administered at 0, 1.5 hrs and 3.0 hrs, respectively. This simulated binge dosing is repeated every 4 days (day 1, 4, 8, 12 and 16) for up to 16 days.

The EthoVision system, which has video tracking and digitized motion analysis, is used for continuous behavioral monitoring. d-methamphetamine-induced locomotor activity, e.g., distance traveled, percentage of the time spent moving, and animal rearing, are measured over a 6 hr period. From each day of behavioral experiments, the time to maximum effects after each dose of d-methamphetamine, the maximum effect, the area under the behavioral effect curve from the time of dosing to the end of each type of behavioral effect, and the duration of effects are calculated. The end of each behavioral effect is based on a statistical analysis of the average baseline response prior to drug administration. For instance, the point at which the animals' response has returned to 1+S.D. of the mean pre-drug response for two consecutive 2 min intervals. The data are analyzed by a two-way (dose of d-methamphetamine and time) repeated measures ANOVA, followed by a Student-Newman-Keuls post hoc test. The results are considered significant at $P<0.05$.

Example 10

Pharmacodynamic Mechanisms of Monoclonal Antibody-Based Antagonism of High Dose (+)-Methamphetamine in Rats This example demonstrates that anti-(+)-methamphetamine monoclonal antibodies antagonize (+)-methamphetamine-induced locomotor effects by altering brain distribution of (+)-methamphetamine.

Two (+)-methamphetamine-like haptens with either a six- or four-carbon spacer group were used for antibody production. The complete synthesis of the (+)-P6-METH hapten (S-(+)-4-(5-carboxypentyl) methamphetamine HCl) was previously described (Byrnes-Blake et al., 2001). The (+)-P4-METH hapten (S-(+)-4-(3-carboxypropyl) methamphetamine HCl) was synthesized in a similar fashion. Both haptens were conjugated (Davis and Preston, 1981) to bovine serum albumin (BSA) for use as an antigen.

Female BALB/c mice (Charles River Laboratories, Wilmington, Mass.) were immunized with 100 μg of the hapten-conjugates emulsified 1:1 (v/v) with TiterMax adjuvant and boosted every 4 weeks with 50 ug of the antigen. Initial immunization and subsequent boosts were administered in two 40 ul subcutaneous injections. Blood samples were taken periodically by tail bleed to measure anti-(+)-methamphetamine antibody titer by an ELISA utilizing hapten-ovalbumin conjugates. Mice with the highest anti-(+)-methamphetamine serum titer was chosen for mAb production. Standard hybridoma technology was utilized for the production of the mAb. Hybridoma cell lines were screened for anti-(+)-methamphetamine antibody production by ELISA.

A low-affinity mAb (mAb 6H8; $K_D$=250 nM) was generated from immunization with the (+)-P4-METH-BSA conjugate, and a higher-affinity mAb (mAb 6H4; $K_D$=11 nM) was generated from immunization with the (+)-P6-METH-BSA conjugate. Both antibodies were IgG$_1$ with a κ light chain.

Figure 8:
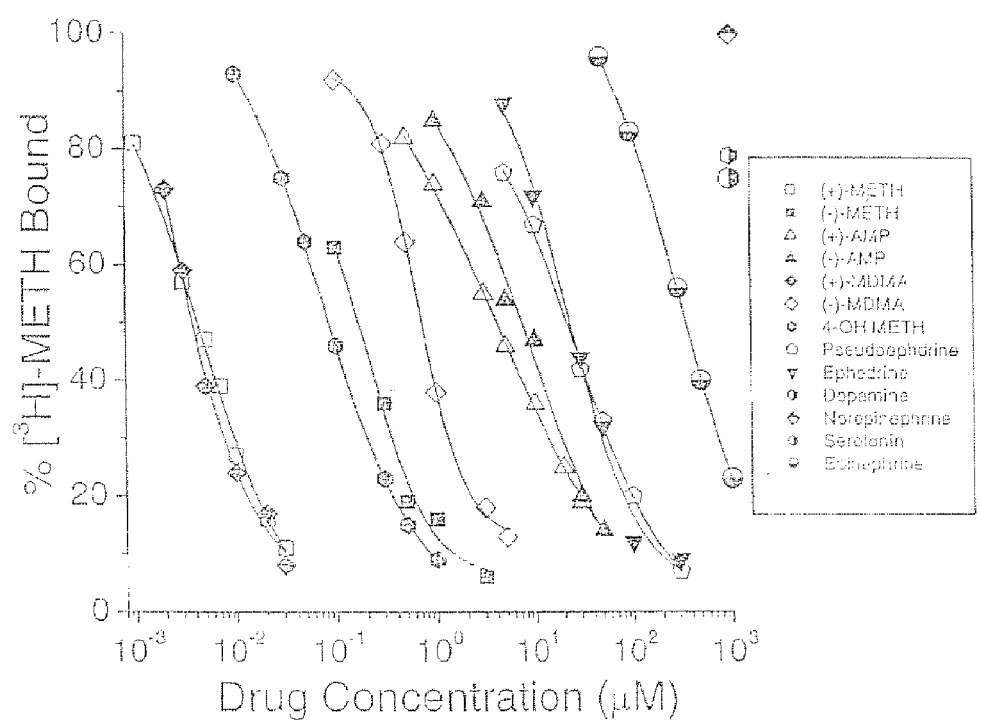
FIG. 8 shows the cross-reactivity profile of mAb6H4 determined by radioimmunoassay similar to that described by Owens et al. (1988). The percentage bound equals the percentage of $B_0$ (amount of $^3$H-(+)-methamphetamine binding in the absence of any competing unlabeled drug) corrected for nonspecific binding. The data were fit with the use of sigmoidal curves that allowed the determination of the $IC_{50}$ values (concentrations of unlabeled drug that caused a 50% inhibition of $^3$H-(+)-methamphetamine binding).

The mAbs were highly specific for (+)-methamphetamine, having <0.1% cross-reactivity with most compounds tested. The one exception was the drug of abuse MDMA or "ecstasy" to which mAb 6H4 bound with a slightly higher relative affinity than (+)-methamphetamine (9 nM vs. 11 nM) (FIG. 8). Both mAbs were also stereospecific, having an approximately 50-200 times higher relative affinity for (+)-methamphetamine and (+)-amphetamine than for the minus forms of these drugs. In addition to the compounds shown in FIG. 8, there was no significant cross-reactivity with (+)- and (−)-MDA, (+)-norpseudoephedrine, L-phenylephrine, (+)-phenylpropanolamine, β-phenylethylamine and tyramine.

The day before being administered to the animals, the mAbs were ultracentrifuged at 100,000 g for 90 min at 4° C. and at 3,300 g for 20 min. This step was used to eliminate large-molecular-weight antibody complexes that can be highly antigenic. The mAb formulations were warmed to 37° C. before i.v. administration to the animals.

Locomotor Activity in the Rat Model

Locomotor activity was used as a measure of (+)-methamphetamine's effects because 0.3-3.0-mg/kg doses of (+)-methamphetamine produced dose-dependent and reproducible increases in both distance traveled and rearing (Riviere et al., 1999). Higher doses were not used because preliminary studies showed i.v. doses ≥5.2 mg/kg led to self-mutilation, and 10-mg/kg doses were sometimes lethal. The time of mAb treatment (t=30 min) was chosen because (+)-amphetamine formation is near maximum, (+)-methamphetamine distribution to the peripheral tissues is virtually complete (Riviere et al., 1999, 2000), and the drug-induced locomotor effects are profound at this time point.

Figure 9:
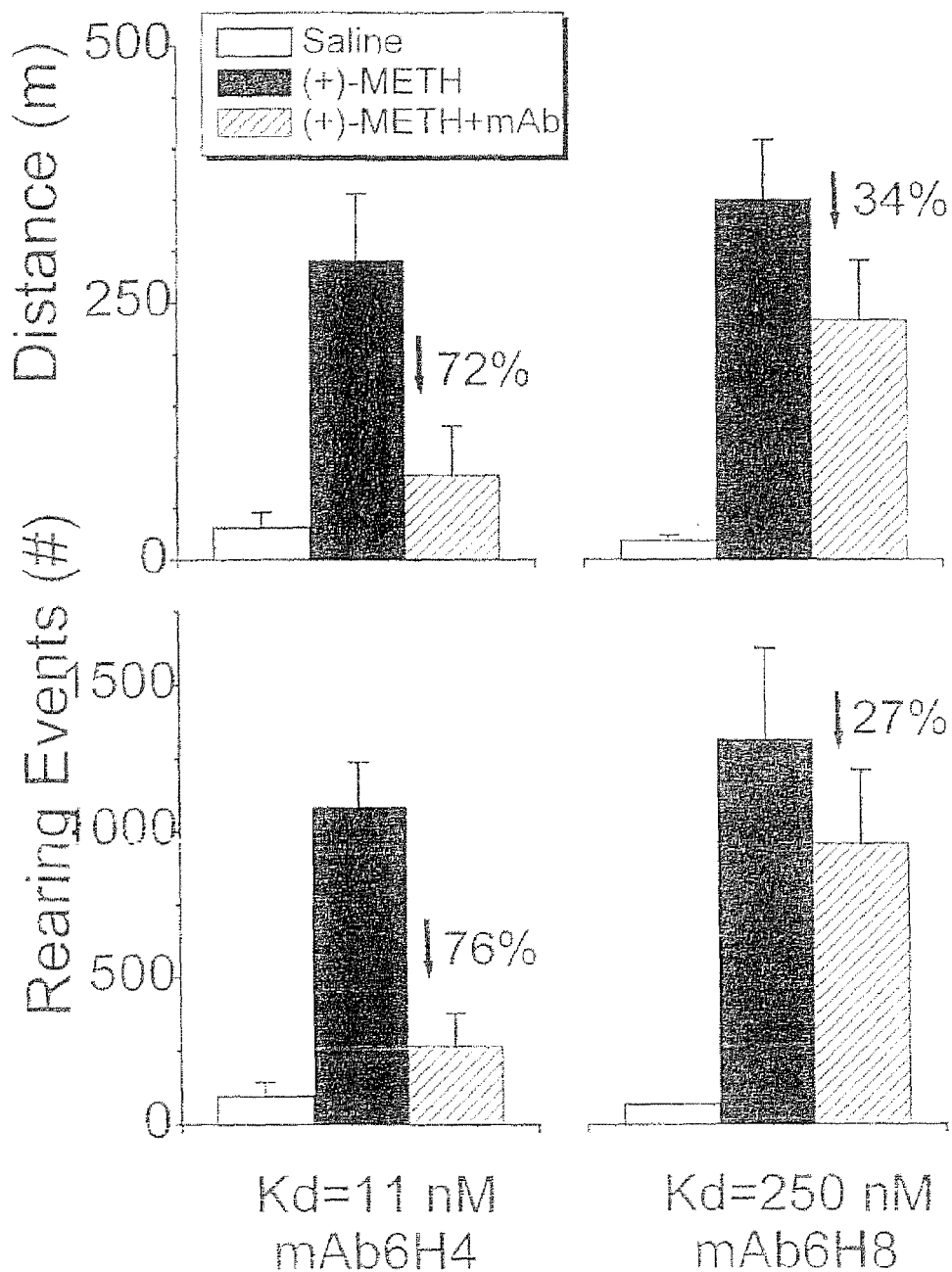
FIG. 9 compares the ability of a high (left panel) and a low affinity (right panel) mAb to reverse (+)-methamphetamine-induced stimulant effects (distance traveled and rearing behavior). Before the mAb experiments, the rats were treated on two separate days with a 1-mg/kg i.v. dose of (+)-methamphetamine followed 30 min later by buffer to establish control values (data not shown). For the mAb experiments, rats received another 1-mg/kg i.v. (+)-methamphetamine dose followed 30 min later by a high-affinity mAb or a low-affinity mAb. The data are shown as the mean +1 S.D. (n=6 per group). The arrows and percentages reflect the degree of mAb-induced reduction in (+)-methamphetamine behavioral response compared to control values.

Comparison of the Reversal of (+)-Methamphetamine-induced Locomotor Activity by a Low- and High-affinity Anti-(+)-Methamphetamine mAb To help elucidate the role of antibody affinity as a determinant of therapeutic efficacy, the low-affinity mAb (mAb 6H8) and the high-affinity mAb (mAb 6H4) were compared for their ability to reverse the locomotor activity following a 1-mg/kg i.v. (+)-methamphetamine dose. The high-affinity mAb more effectively antagonized both distance traveled and rearing than the low-affinity mAb (FIG. 9).

Figure 10:
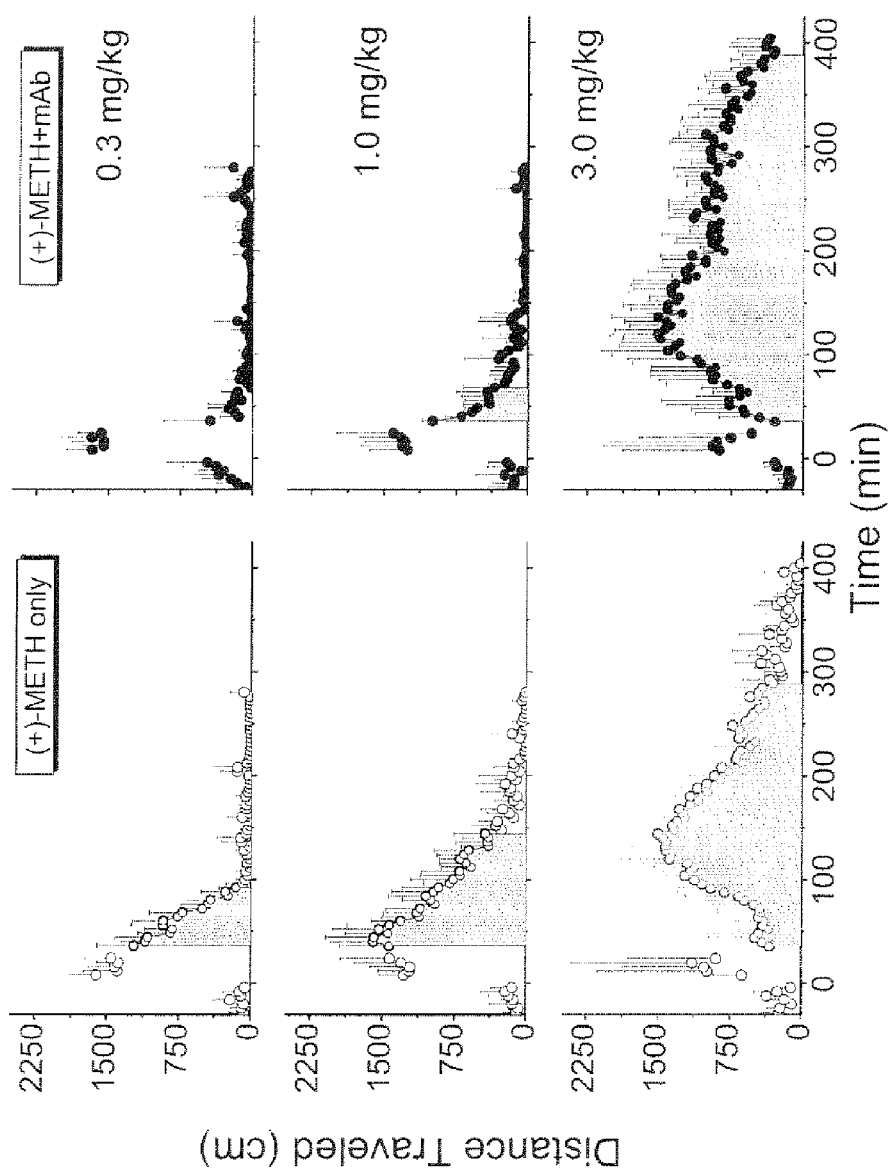
FIG. 10 shows the time course of (+)-methamphetamine-induced distance traveled in rats (n=6) with either buffer (left panel; open circles) or mAb6H4 (right panel; filled circles) treatment. The i.v. (+)-methamphetamine doses were 0.3, 1.0, and 3.0 mg/kg. The left arrow indicates the time of (+)-methamphetamine administration, and the arrowhead indicates the time of mAb6H4 administration. Shading indicates the duration of drug action above saline-induced (baseline) locomotor activity following buffer or mAb administration. The time needed to return to baseline was determined by statistical comparison of the behavior starting at t=30 min (time of treatment) with each animal's predosing behavior from −30 min to t=0.
Figure 11:
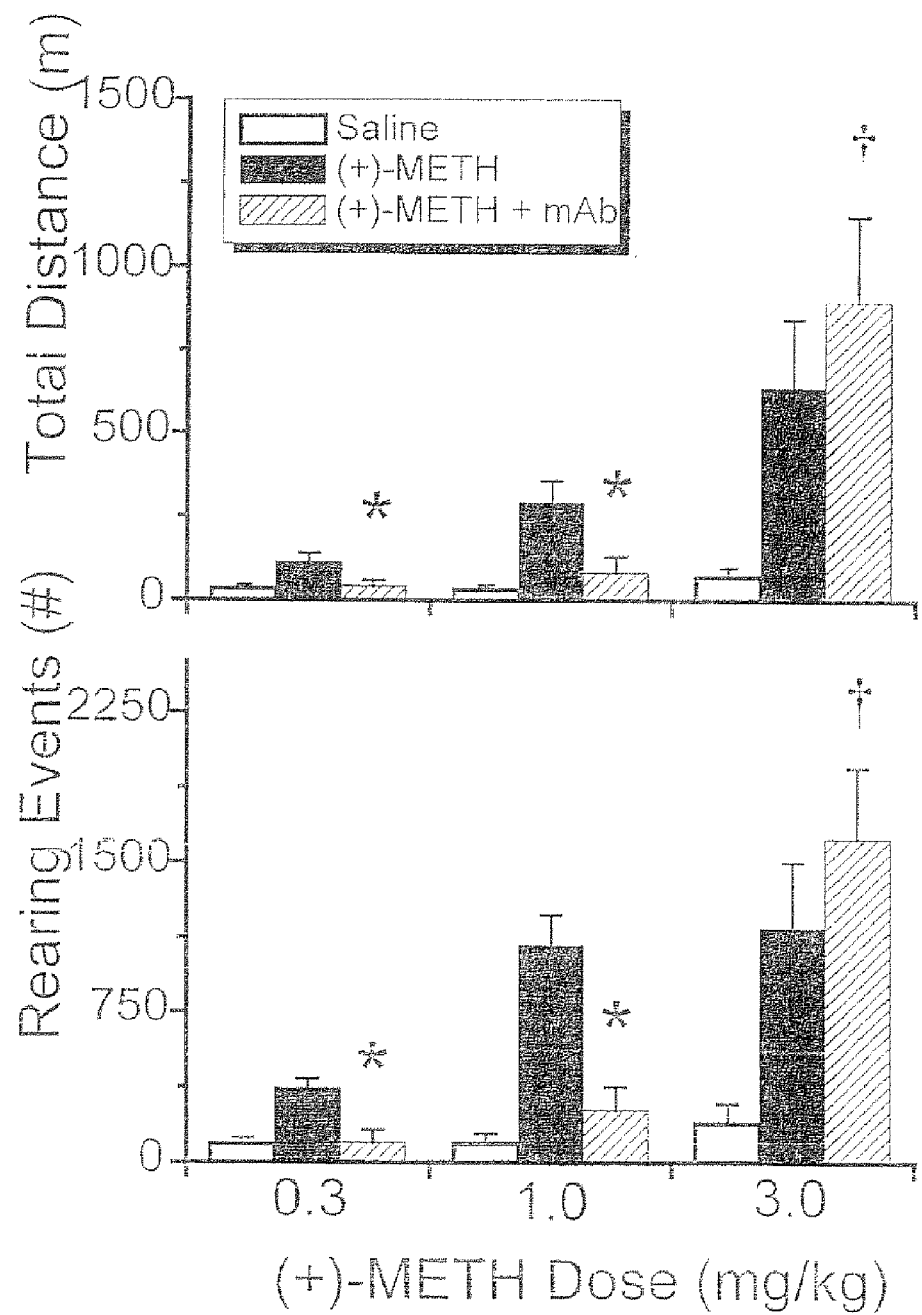
FIG. 11 shows the summary of dose-response results in groups of animals receiving 0.3, 1.0, or 3.0 mg/kg (+)-methamphetamine. The animals received saline followed 30 min later by buffer. Three days later, they received a priming dose (0.3, 1.0, or 3.0 mg/kg) of (+)-methamphetamine followed 30 min later by buffer (data not shown). This was followed 3 days later by a second (+)-methamphetamine priming dose with buffer at t=30 min. Three days later, they received a final (+)-methamphetamine dose (0.3, 1.0, or 3.0 mg/kg) followed at t=30 min by mAb6H4 (the high-affinity mAb). These data are shown as the means +1 S.D. (n=6 per group). * indicates a significant decrease in locomotor activity compared with (+)-methamphetamine; † indicates a significant increase in locomotor activity compared with (+)-methamphetamine ($p<0.05$).

Effect of the High-Affinity Anti-(+)-Methamphetamine mAb on (+)-Methamphetamine-Induced Locomotor Activity These results show the ability of a fixed mAb dose to antagonize the effects of (+)-methamphetamine at three different doses. The time-dependent pattern of time spent moving was very similar to the time-dependent pattern of distance traveled, but it appeared to be a less sensitive measure. Therefore, the results for this parameter were not reported. FIG. 10 shows the time course of both distance traveled and rearing events after (+)-methamphetamine administration both without and with mAb treatment. FIG. 11 shows a summary of the total distance traveled and rearing events during the entire experimental period for each dosing group.

For both the 0.3 and 1.0 mg/kg (+)-methamphetamine doses, the high-affinity mAb substantially reduced the locomotor activities (distance traveled and rearing events) from baseline (+)-methamphetamine activities by >60% and >70%, respectively (all p<0.05). However, there was a significant increase in both distance traveled and rearing behavior when animals received 3.0 mg/kg (+)-methamphetamine followed by the mAb (p<0.05; FIG. 11).

At the end of the experimental protocol, animals that received the 1.0-mg/kg doses of (+)-methamphetamine also received a second saline treatment followed by buffer. The saline-induced behavior was not significantly different from that obtained at the start of the study (p<0.05).

In addition to assessing mAb-induced changes in total distance traveled and the number of rearing events, changes in the duration of (+)-methamphetamine's action were also evaluated to measure the effects of mAb6H4. The duration of (+)-methamphetamine-induced locomotor effects following treatment (treatment=buffer vs. mAb) was approximately 1 h compared with 6 min for the 0.3-mg/kg dose and 2 h compared with 32 min for the 1.0-mg/kg dose. When the mAb was administered to the 3.0-mg/kg group, however, the duration of drug action increased from 4 to 6 h (FIG. 10).

Figure 12:
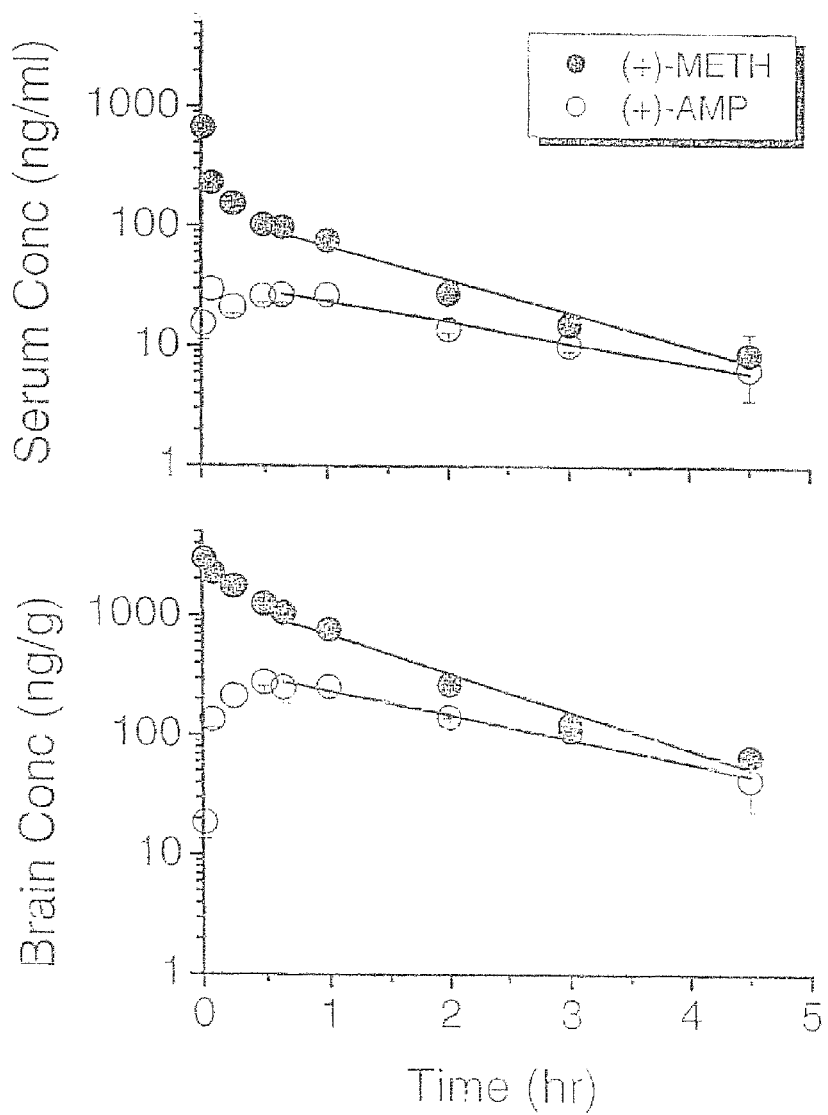
FIG. 12 shows average concentration-versus-time profiles for (+)-methamphetamine and (+)-amphetamine in serum (top panel) and brain (lower panel). The solid lines associated with the (+)-methamphetamine and (+)-amphetamine data show the linear-regression fit to the terminal log concentration-versus-time data as determined by model-independent analysis. All values are represented as the mean ±1 S.D. (n=3 per time point).

(+)-Methamphetamine and (+)-Amphetamine Pharmacokinetic Profile after (+)-Methamphetamine Administration The disposition of (+)-methamphetamine and its active metabolite, (+)-amphetamine, after a 1.0-mg/kg i.v. (+)-methamphetamine dose were similar to those of Riviere et al. (2000). The concentration-versus-time profiles of (+)-methamphetamine in serum and brain were best described by a two-compartment model with $1/y^2$ weighting. The distribution half-life of (+)-methamphetamine was 1.7 min in serum and 26 min for brain. In both serum and brain, the highest (+)-methamphetamine concentrations were achieved at the earliest measured time point (1 min; FIG. 12), followed by a biexponential decline. The metabolite (+)-amphetamine achieved apparent maximum concentrations in serum and brain at about 30 min (FIG. 12). Table 1 summarizes the pharmacokinetic values.

Figure 13:
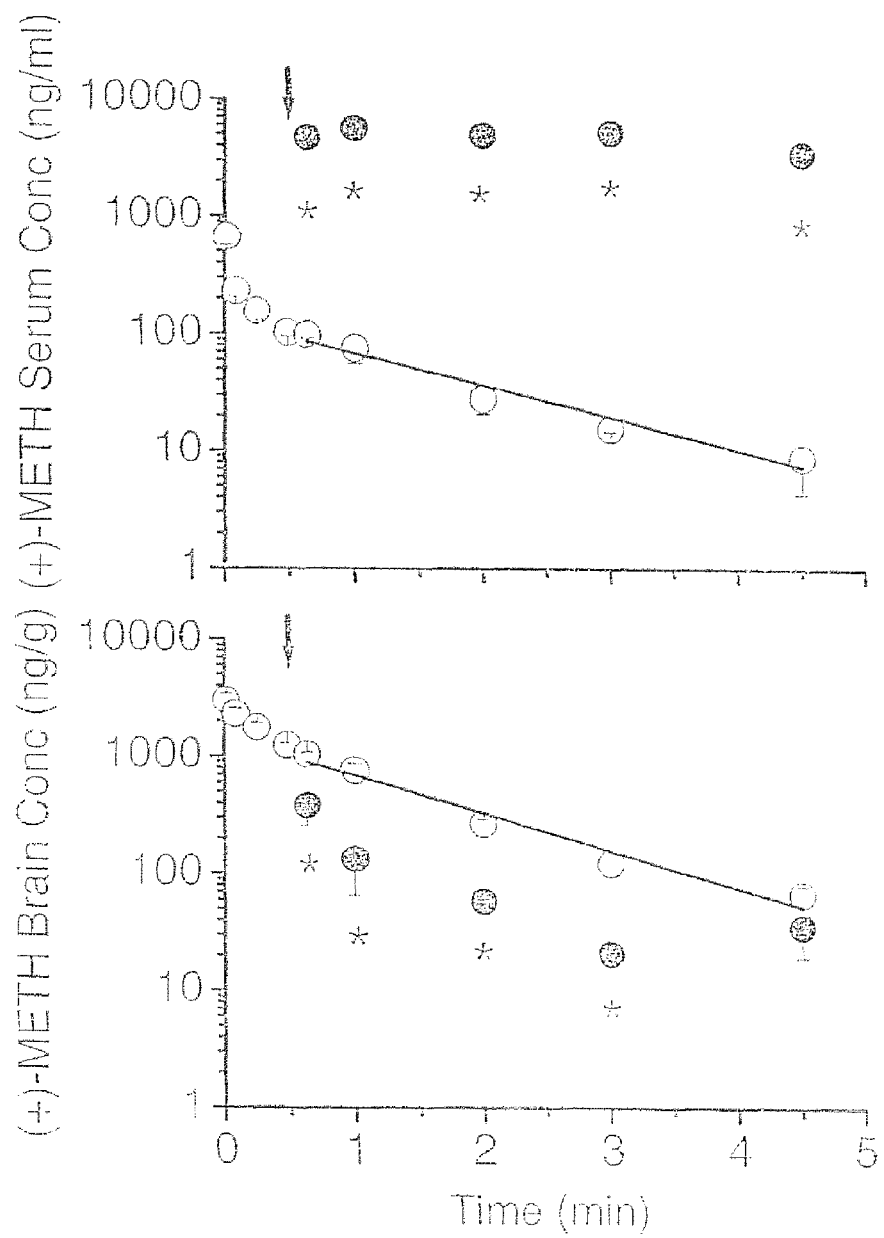
FIG. 13 shows average concentration-versus-time profiles for (+)-methamphetamine with (filled circle) and without (open circle) mAb6H4 administered at t=30 min in serum (top panel) and brain (lower panel). The solid lines associated with the data show the linear-regression fit to the terminal log concentration-versus-time data as determined by model-independent analysis. The arrow indicates the time of mAb administration. All values are represented as the mean ±1 S.D, n=3 per time point. * indicates a significant difference from control ($p<0.05$).
Figure 14:
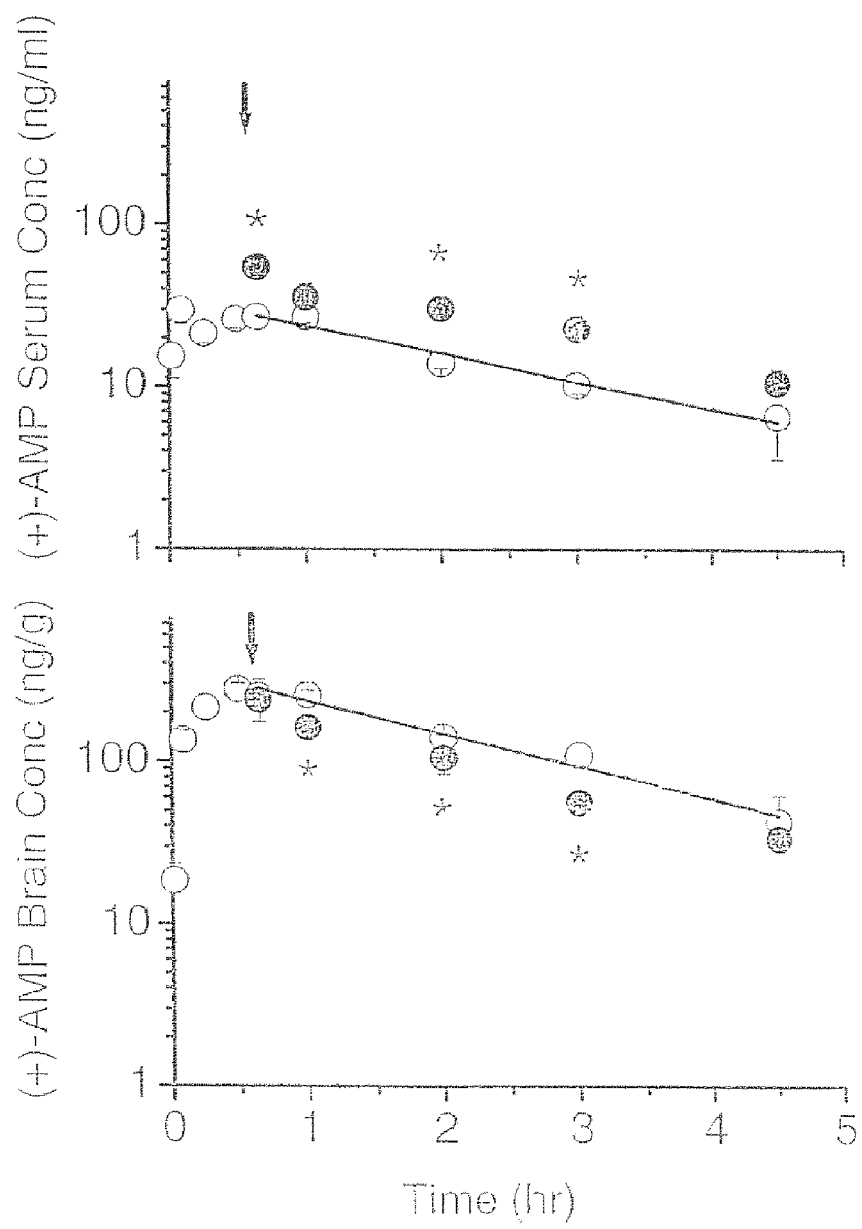
FIG. 14 shows average concentration-versus-time profiles for (+)-amphetamine with (filled circles) and without (open circles) mAb6H4 administration at t=30 min in serum (top panel) and brain (lower panel). The solid lines associated with the data show the linear-regression fit to the terminal log concentration-versus-time data as determined by model-independent analysis. The arrow indicates the time of mAb administration. All values are represented as the mean ±1 S.D. (n=3 per time point). * indicates a significant difference from control ($p<0.05$).

Effect of High-Affinity Anti-(+)-Methamphetamine mAb on the Pharmacokinetic Profiles of (+)-Methamphetamine and (+)-Amphetamine Administration of the high-affinity mAb (mAb6H4) at t=30 min after (+)-methamphetamine administration led to a substantial change in the drug's disposition. Concentrations of (+)-methamphetamine in serum were significantly higher, corresponding to lower concentrations in brain (FIG. 13). The $AUC_{38min-1.5h}$ value for the serum (+)-methamphetamine concentration-versus-time profile showed a >9000% increase, whereas the $AUC_{38min-1.5h}$ for brain showed a >70% decrease. The $t_{1/2\lambda Z}$ values in the mAb-treated animals were not determined, as the elimination phase of the concentration-time profile could not be fully characterized within the 4.5-h experiment. The (+)-methamphetamine $AUC_{brain}$-to-$AUC_{serum}$ ratio was greatly decreased due to the large increase in serum concentrations (Table 1). The mAb had a significant effect on serum and brain (+)-amphetamine concentrations at some of the time points, but the effect was not as large as that seen with (+)-methamphetamine (FIG. 14). Because of the mAb's differential effects on (+)-methamphetamine and its metabolite (+)-amphetamine, there were major changes in the molar ratio of $AUC_{AMP}$ to $AUC_{METH}$ in both serum and brain (Table 1).

TABLE 1

Parmacokinetic Parameters Of (+)-METH And Its Metabolite (+)-AMP After A 1-mg/kg i.v. (+)-METH Dose[a]

| Tissue | Drug | $T_{1/2\lambda z}$ Control | $T_{1/2\lambda z}$ Treated | $AUC_{38min-1.5h}$ Control | $AUC_{38min-1.5h}$ Treated | $AUC_{brain}$ | $AUC_{serum}$ | Molar Ratio of (+)-AMP to (+)-METH $AUC^b$ Control | Molar Ratio of (+)-AMP to (+)-METH $AUC^b$ Treated |
|---|---|---|---|---|---|---|---|---|---|
| | | h | h | ng · h/ml or ng · h/g | ng · h/ml or ng · h/g | Control | Treated | Control | Treated |
| Serum | (+)-METH | 1.08 | NC | 123 | 12,266 | 1 | 1 | 0.49 | 0.01 |
| Serum | (+)-AMP | 1.8 | NC | 55 | 73 | 1 | 1 | | |
| Brain | (+)-METH | 0.95 | NC | 1182 | 246 | 9.6 | 0.02 | 0.49 | 1.26 |
| Brain | (+)-AMP | 1.5 | NC | 530 | 284 | 9.6 | 3.4 | | |

[a]Data are shown from animals both without treatment (control) and with treatment (1-mol equivalent dose of mAb). All parameters were calculated by model-independent analysis. NC, not calculated due to inadequate sampling during the terminal phase.
[b]The molar ration of (+)-AMP to (+)-METH AUC was calculated by dividing the nmol · h/g or nmol · h/ml AUCvalues.

Discussion for Example 10

The overall goal of these studies was to determine the mechanisms associated with anti-(+)-methamphetamine mAb-based antagonism of (+)-methamphetamine-induced locomotor effects in a rat overdose model. The influence of mAb affinity on therapeutic success was first examined because there was no previous studies addressing this important issue. Two mAbs were developed for these studies. Both mAbs were of the same isotype and light chain and were highly specific for (+)-methamphetamine. They differed in only one important aspect: a 25-fold difference in $K_D$ values.

The higher-affinity mAb was two to three times more effective than the lower-affinity mAb at reducing (+)-methamphetamine-induced distance traveled and rearing events (FIG. 10). However, even the higher-affinity mAb6H4 did not achieve the maximum possible antagonism against the effects of (+)-methamphetamine, and experimental evidence suggests that another 10- to 25-fold increase in mAb affinity would be needed to significantly improve the therapy further. The hypothesis that a higher affinity mAb (e.g., $K_D$=1 nM) would offer substantial improvements is supported by other studies showing that an anti-phencyclidine mAb with a $K_D$ of 1.8 nM can completely reverse phencyclidine's locomotor effects (Hardin et al., 1998). A single dose of that antibody can reduce brain concentrations of phencyclidine for at least one month (Proksch et al., 2000). However, it should be noted that the (+)-methamphetamine rat model is complicated by the presence of a pharmacologically active metabolite, (+)-amphetamine, with which mAb6H8 and mAb6H4 do not cross-react. A mAb with increased cross-reactivity for (+)-amphetamine (or a cocktail of an anti-(+)-methamphetamine and an anti-(+)-amphetamine mAb) may improve the effectiveness of the therapy.

Due to its relatively superior effectiveness, the high-affinity mAb was used for all subsequent behavioral and pharmacokinetic studies. A fixed dose of the high-affinity mAb (equimolar to the (+)-methamphetamine body burden at 30 min after a 1-mg/kg (+)-methamphetamine dose) effectively antagonized (+)-methamphetamine-induced effects when the (+)-methamphetamine dose was equal to or less than the mAb dose (FIGS. 10 and 11). The mAb also significantly decreased the drug's duration of action at both (+)-methamphetamine doses (FIG. 10). However, when the drug dose was greater than the mAb binding capacity (i.e., at the 3.0-mg/kg), locomotor activity was increased after mAb administration compared with that seen after (+)-methamphetamine administration followed by buffer.

Several possible explanations exist for these apparent complex changes in behavior at the high (+)-methamphetamine-to-mAb ratio. First, the locomotor activity could have maximized at doses somewhere between 1 and 3 mg/kg. This is described as a so-called inverted-U-shaped dose-response curve. If this were the case, mAb administered at a dose equimolar to a 1-mg/kg (+)-methamphetamine dose could have neutralized part of the drug dose, thus shifting the dose-response curve back to the point of an apparent increase in locomotor activity. This hypothesis was tested by quantitating locomotor activity in rats after administering a 1.8-mg/kg (+)-methamphetamine dose (a half log dose between 1- and 3-mg/kg). The 1.8-mg/kg dose produced locomotor effects that were about equal to the effects of the 1- and 3-mg/kg (+)-methamphetamine doses (data not shown). Thus, the increased activity following mAb treatment in the 3.0-mg/kg-dose group could not be explained by a simple shift to the left in the (+)-methamphetamine dose-response curve.

A possible pharmacodynamic reason for the increase in the behavior is described as follows. It is quite likely that (+)-methamphetamine's multiple mechanisms of action in the brain and peripheral sites have different concentration-response relationships and are more or less susceptible to the neutralizing, beneficial effects of the mAb. Thus, when the mAb is present in limited amounts relative to the amount of drug, the mAb would presumably have the greatest effects on the most accessible and lowest-affinity effector sites. It is also possible that the mAb could preferentially neutralize the behaviorally suppressive effects, like stereotyped behavior, while allowing the stimulatory effects to predominate.

There are also pharmacokinetic and immunological explanations for the increase in total locomotor activity. Firstly, the mAb appeared to have substantially slowed (+)-methamphetamine's entry into the CNS through high-affinity binding in serum (FIG. 13). This would have led to a decreased amount of (+)-methamphetamine reaching the CNS but prolonged availability of the drug. Secondly, significant amounts of the active metabolite, (+)-amphetamine, may have accumulated because (+)-amphetamine has a longer half-life than (+)-methamphetamine in rats (Riviere et al., 1999, 2000; Cho et al., 2001; Table 1). In addition, (+)-amphetamine does not significantly cross-react with the mAb. Thirdly, the association and dissociation of (+)-methamphetamine with the mAb and its relationship to the influx and efflux of the drug in the CNS could also be factors. In an attempt to address this point, the behavioral effects following a 3-mg/kg intraperitoneal (i.p.) (+)-methamphetamine dose were compared with those of the 3-mg/kg i.v. dose. The i.p. route was chosen because it provides a model of a slower drug input into the brain and would produce greater (+)-amphetamine concentrations due to liver first-pass metabolism. The data showed that the i.p. route of administration resulted in significantly increased effects compared with those of the i.v. route. These findings suggest that the rate of drug entry in the CNS and the increased (+)-amphetamine concentrations are important factors in (+)-methamphetamine-induced locomotor activity and the effectiveness of the mAb.

Pharmacokinetic studies were conducted to help determine some of the mechanisms for the behavioral effects. These studies were carried out with a 1:1 molar ratio of (+)-methamphetamine to mAb. Serum was chosen because (+)-methamphetamine is transported to its sites of action via the bloodstream and mAbs are confined mainly to the serum volume. The brain was chosen for study because it is the major site of action contributing to (+)-methamphetamine's locomotor effects.

Immediately after the administration of mAb6H4, serum (+)-methamphetamine concentrations dramatically increased and remained high throughout the duration of the experiment (FIG. 13). The concentrations were measured for only 4.5 h so that better understanding of the pharmacokinetic processes associated with the pharmacological-effect period of (+)-methamphetamine (FIG. 10) can be obtained. The mAb also produced immediate decreases in brain (+)-methamphetamine concentrations which were sustained for at least 3 h. This immediate reduction in brain concentrations was totally consistent with the immediate reversal of (+)-methamphetamine-induced locomotor effects at the 1-mg/kg dose (FIG. 10). However, by 4.5 h, the brain concentration appeared to rebound and was then not significantly different from that of the control animals. By this point, however, the (+)-methamphetamine concentration in control and treatment animals appeared to be below the threshold concentration leading to locomotor activity. These pharmacokinetic changes for (+)-methamphetamine are consistent with a similar dramatic decrease (and rebound) in phencyclidine brain concentrations after anti-phencyclidine Fab fragment treatment in rats (Valentine and Owens, 1996). It is believed that these changes resulted from the rapid mAb-induced redistribution of drug from the brain, followed by an increase in drug concentrations due to a slower redistribution from other tissues.

The effect of the mAb on (+)-amphetamine concentrations was small, compared to its effect on (+)-methamphetamine concentrations. This is not surprising because the mAb had little cross-reactivity with (+)-amphetamine in vitro. The small mAb-induced increase in serum concentrations of (+)-amphetamine may result from increased amounts of (+)-methamphetamine in the serum available for metabolism. This hypothesis can be proved by knowing the free concentrations and serum clearance of (+)-methamphetamine. The small decrease in (+)-amphetamine concentrations in brain and the dramatic decrease of (+)-methamphetamine concentrations in brain suggest the possibility of brain conversion of (+)-methamphetamine to (+)-amphetamine. However, data are insufficient to fully support this conclusion.

These data indicate that the 70% decrease in brain (+)-methamphetamine AUC is a direct cause of the 70% decrease in behavioral effects following mAb treatment at the 1-mg/kg dose. In addition, (+)-amphetamine formation does not play a significant role in (+)-methamphetamine's pharmacological effects at this dose. This would not be the case at the 3-mg/kg dose because brain (+)-amphetamine concentrations would be approximately threefold greater at all time points. The ratio of the (+)-amphetamine AUC to the (+)-methamphetamine AUC in serum and brain of rats is about 49% (Riviere et al., 2000). However, the amounts of (+)-amphetamine in humans appear to be substantially lower (Cook et al., 1993). Therefore, the prediction of beneficial effects in humans based on rat data is somewhat hindered by the very high (+)-amphetamine-to-(+)-methamphetamine ratio in the rat.

In conclusion, the effects of mAb therapy for (+)-methamphetamine are dependent on mAb affinity, dose and specificity. Monoclonal antibodies with improved affinity for (+)-methamphetamine, and possibly increased cross-reactivity with (+)-amphetamine, could offer improvements in the effectiveness of the therapy.

Animal Protocols for Example 10

Male Sprague-Dawley rats were obtained from Hilltop Laboratories (Scottsdale, Pa.) with an indwelling jugular venous catheter (Silastic medical-grade tubing, 0.020-inch inner diameter and 0.037-inch outer diameter; Dow Corning Corporation, Midland, Mich.). Catheter patency was maintained with a saline and 25 U of heparin flushes every other morning. The rats were housed separately, and their weight was maintained between 270-300 g throughout the experiment. All animal experiments were conducted with the approval of the Institutional Animal Care and Use Committee of the University of Arkansas for Medical Sciences and were in accordance with the Guide for the Care and Use of Laboratory Animals adopted and promulgated by the National Institutes of Health.

Protocol for (+)-Methamphetamine Locomotor Activity Studies of Example 10

The parameters of distance traveled (in centimeters or meters), number of rearing events, and time spent moving (in seconds) were individually quantified for each animal. The general protocol was previously described (Hardin et al., 1998; Riviere et al., 1999). Briefly, animals were placed in polyethylene chambers that contained a bedding of dark-gray clay. Animal behavior was videotaped, and the video images were digitized and quantitated in 4-min intervals by EthoVision software (Noldus Information Technology Inc., Sterling, Va.). The duration of drug action was calculated for each parameter starting at 30 min (time of treatment) and until the locomotor activity returned to baseline. Locomotor activity was determined to have returned to baseline levels when two consecutive 4-min intervals were less than or equal to the mean+1 S.D. of the 30-min behavioral baseline observed just before drug administration.

Rats were habituated to the behavioral monitoring chambers before the start of the experimental protocol. This was accomplished by placing the rats in the chambers for a minimum of 3 h per day for 4-6 consecutive days. After the habituation phase, the rats were then randomly divided into three (+)-methamphetamine-dosing groups (n=6 rats per group). The rats in each group were dosed every three days for a total of 10 days. All saline and (+)-methamphetamine injections were administered via the jugular catheter as a 15-sec i.v. infusion.

On day 1, all groups received saline followed at 30 min by mAb buffer to obtain baseline (non-drug-induced) behavior. Then on days 4 and 7, they received a pretreatment dose of either 0.3, 1.0, or 3.0 mg/kg (+)-methamphetamine followed at 30 min by buffer. Two (+)-methamphetamine sessions were conducted because preliminary studies showed that, on average, the rats had a lower (+)-methamphetamine-induced locomotor response to the first i.v. injection of the drug than to the second and subsequent injections (data not shown). Thus, the second pretreatment drug dose was used to determine the (+)-methamphetamine-induced locomotor activity baseline.

The third and final dose of 0.3, 1.0, or 3.0 mg/kg (+)-methamphetamine was administered on the last day of the protocol. This dose was followed at t=30 min by i.v. injection of the high-affinity anti-(+)-methamphetamine mAb (mAb6H4; $K_D$=11 nM). The 30-min time point was chosen for treatment because previous studies showed that locomotor activity and active metabolite concentrations ((+)-amphetamine) in tissues are near maximum at 30 min (Riviere et al., 1999, 2000). The amount of mAb administered was 367 mg/kg, which is equimolar (assuming two binding sites per IgG molecule) to the amount of (+)-methamphetamine left in the body at t=30 min. The amount of drug remaining was determined from the serum pharmacokinetic data from Riviere et al. (1999) and by the equation: body burden=dose×$e^{-kt}$ (Rowland and Tozer, 1995). This simple monoexponential elimination phase equation could be used to calculate the body burden at 30 min because the distribution phase for (+)-methamphetamine in serum is extremely short ($t_{1/2dist}$=9 min).

All control buffer and mAb solutions were administered via the jugular venous catheter in an 8-ml volume at 2 ml/min. Three days after the end of the experimental protocol for the 1-mg/kg group, locomotor activity from a second saline administration was monitored to determine whether any changes had occurred in baseline activity.

In another study, the therapeutic effectiveness of the low-affinity mAb (mAb6H8; $K_D$=250 nM) and that of the high-affinity mAb were directly compared. Data from the 1-mg/kg group in the experiment described in the previous paragraphs (with mAb6H4) were compared with data from a group of rats (n=6) administered 1 mg/kg (+)-methamphetamine and treated at t=30 min with mAb6H8. All other aspects of the protocol were as just described.

Protocol for (+)-Methamphetamine and (+)-Amphetamine Pharmacokinetic Studies of Example 10

Before each pharmacokinetic experiment, a 1-mg/kg (+)-methamphetamine dose plus a 333-µCi/kg $^3$H-(+)-methamphetamine dose was prepared in sterile saline. This allowed the administration of approximately 100 µCi per rat by injection of 1 µl/g of rat body weight.

Male Sprague-Dawley rats were randomly placed into two groups. The first group (n=3 per time point for all pharmacokinetics studies) was the control group that did not receive antibody. Rats in this group were administered a 15-sec i.v. injection of the (+)-methamphetamine/[$^3$H]-(+)-methamphetamine solution via the jugular venous catheter and were then placed in metabolism cages (Nalge Nunc International, Rochester, N.Y.). At various predetermined times after injection (1, 5, 15, 29, and 38 min; 1, 2, 3, and 4.5 h), the rats were sacrificed. At the early time points (1 and 5 min), the rats were anesthetized before drug injection so that an immediate laparotomy could be performed to obtain blood from the inferior vena cava, and decapitation could take place at the correct time. At later time points (15 min onward), rats were anesthetized 5 min before the desired time of sacrifice (decapitation) to allow time for obtaining sufficient depth of anesthesia and for the laparotomy and blood collection to take place. Ethyl ether was used for anesthesia so that hemodynamic stability could be maintained before animal sacrifice. Immediately after blood collection, the rats were decapitated and the brain was removed. The brain was rinsed with saline, weighed, and placed in liquid nitrogen within 3 min of decapitation. Hematocrit values were obtained for each animal. The blood was allowed to clot and serum was obtained after centrifugation. The serum and brain tissues were stored at −80° C. until analyzed.

The second group was the mAb-treatment group. All aspects of the experiment were same as those described for the control group, with the following exception. At t=30 min, each rat was administered 367 mg/kg of the mAb (equimolar to the body burden of (+)-METH in the rat at 30 min). The mAb was given via the jugular venous catheter in an 8-ml volume at 2 ml/min. Because the experimental protocol was the same up until the mAb was administered, the time points before 30 min were not repeated in this group.

Analysis of Drug Concentrations of Example 10

(+)-methamphetamine and (+)-amphetamine were extracted from serum and brain with the use of a solid-phase extraction procedure. For serum analysis, 300 μl of guanidine HCl was added to 200-μl of each serum sample to denature the proteins. The samples were vortexed and placed on a gentle shaker for 30 min. Then, 120 μl of a solution containing 0.025-mg/ml (+)-methamphetamine/(+)-amphetamine internal standard were added, and each sample mixture was placed directly on solvent-conditioned Oasis HLB extraction cartridges (1 ml, 30 mg; Waters Corporation, Milford, Mass.). After sample application, the cartridges were centrifuged at 230 g for 1 min, washed with 1 ml of water, and then centrifuged. For elution of both (+)-methamphetamine and (+)-amphetamine, the cartridges were transferred to siliconized test tubes, 1 ml of methanol was added, and 1 min of centrifugation followed. Then, 1 ml of methanol:acetic acid (98:2) was added, followed by centrifugation.

To determine (+)-methamphetamine and (+)-amphetamine concentrations in the brain, tissues were homogenized for 30 sec in 5×(v/w; ml/g) ice-cold water with a tissue homogenizer (Tekmar Company, Cincinnati, Ohio). A 200-μl aliquot was then added to 300 μl of 8 M guanidine HCl. The mixture was vortexed and gently shaked for 30 min. Then, 500 μl of water, 120 μl of the (+)-methamphetamine/(+)-amphetamine internal standard, and 300 μl of a 10% $ZnSO_4$ solution (to precipitate proteins) were added. The mixture was vortexed, placed on ice for 5 min, and centrifuged at 12,500 g for 5 min.

Supernatants from the brain samples were applied to conditioned extraction cartridges and then centrifuged at 600 g for 4 min. The brain precipitates left over from the 12,500 g centrifugation were resuspended in 500 μl of water and centrifuged at 12,500 g for 3 min. The supernatants were then added to their respective extraction columns and centrifuged at 600 g for 4 min. This was followed by a 1-ml water wash, with another 4 min centrifugation at 600 g. Finally, the cartridges were placed in siliconized test tubes for sample collection. The elution process was as described for the serum samples.

After elution, the samples were taken to dryness over 3 h in a vacuum centrifuge (Savant Instruments, Inc., Farmingdale, N.Y.) with no heat or cryopumping. They were resuspended in 120 μl of 7% acetonitrile and 93% water (the HPLC starting conditions). A Waters Corporation HPLC system consisting of a pump controller, autoinjector, UV detector, Millennium software, and a Symmetry Shield RP18 (3.5 μm, 4.5×75 mm) column was used to separate (+)-methamphetamine and (+)-amphetamine for quantitation. The mobile phase was 7% acetonitrile and 93% water with 0.1% trifluoroacetic acid. Fractions (10 sec) were collected, and the $^3$H-(+)-methamphetamine and $^3$H-(+)-amphetamine containing fractions were quantified by liquid scintillation spectrometry. The serum and brain drug concentrations were determined from the ratio of unlabeled (+)-methamphetamine or (+)-amphetamine to radiolabeled tracer as previously described (Riviere et al., 1999).

Pharmacokinetic Analysis of Example 10

Brain concentrations were corrected for residual blood content in the organ with the equation: $C_{Total} = (C'_{Tissue} - (C_B * V_B))/(1-V_B)$, where $C_{Total}$ is the concentration of (+)-methamphetamine or (+)-amphetamine in the tissue corrected for blood concentration; $C'_{Tissue}$ is the tissue drug concentration before correction for blood content; $C_B$ is the drug concentration in the blood; and $V_B$ is the volume fraction of the residual blood in each tissue (Triplett et al., 1985). $V_B$ values for brain (0.037) were obtained from Khor et al. (1991).

When no mAb was present, the blood drug concentration was assumed to be equal to the serum drug concentration, as (+)-methamphetamine and (+)-amphetamine distribute equally in red blood cells and serum (Riviere et al., 2000). When the mAb was present, it was assumed (due to high-affinity mAb binding) that all of the drug was in the serum rather than in the red blood cells. The (+)-methamphetamine or (+)-amphetamine concentration in blood for this calculation was determined by multiplying each animal's serum drug concentration by 1 minus their respective hematocrits (Valentine and Owens, 1996).

To determine the distribution half-lives of (+)-methamphetamine and (+)-amphetamine, the average concentration-vs-time curves were analyzed by model-dependent methods using a nonlinear least-squares fitting routine. The data were fit to both two- and three-compartment i.v. bolus models, with y (predicted concentration), 1/y, or $1/y^2$ weighting. The best-fit line was chosen by visual inspection and analysis of the residuals. The terminal elimination half-life ($t_{1/2\lambda Z}$) was determined, where possible, from the terminal phase of the average concentration-vs-time profiles for (+)-methamphetamine and (+)-amphetamine with the use of model-independent analysis. The area under the concentration time curve (AUC) for serum and brain were determined from t=38 min (immediately after mAb treatment) to 4.5 h (last measured time point). Because we could not accurately estimate the pharmacokinetic values after mAb ($t_{1/2\lambda Z}$=8 days, Bazin-Redureau et al., 1997) administration due to the limited period of serum and brain sampling, $AUC_{38min}^{4.5h}$ values were used for comparative purposes. Nevertheless, sufficient data were collected for a comparison of pharmacodynamic changes during (+)-methamphetamine's pharmacological effect period. All pharmacokinetic analysis was performed with the use of WinNonlin V3.0 (Pharsight Corporation, Mountain View, Calif.).

Statistical Analysis for Example 10

To determine if the administration of the high-affinity mAb affects (+)-methamphetamine-induced locomotor activity, the difference between the baseline (+)-methamphetamine activity (day 7) and (+)-methamphetamine activity after treatment (day 10) was calculated. These differences were then analyzed in a one-way ANOVA context with the dose level of (+)-methamphetamine as the factor. Student's t tests of the dose means were carried out, and p-values were adjusted with Holm's correction when applicable. These analyses were performed with SAS System V8.0 software (Cary, N.C.).

For the animals dosed with 1-mg/kg (+)-methamphetamine, comparisons between saline baseline activity (day 1) and a second saline-buffer treatment at the end of the protocol were tested with a paired Student's t-test. To assess mAb-induced changes in (+)-methamphetamine and (+)-amphetamine tissue concentrations at each time point, a Student's two-tailed t test was used. These analyses were conducted with SigmaStat V1.0 software (Jandel Scientific, San Rafael, Calif.). A significance level of p<0.05 was used for all statistical analyses.

Example 11

Effects of Anti-Meth Fab on Meth-Induced Behavioral Effects

Figure 15A:
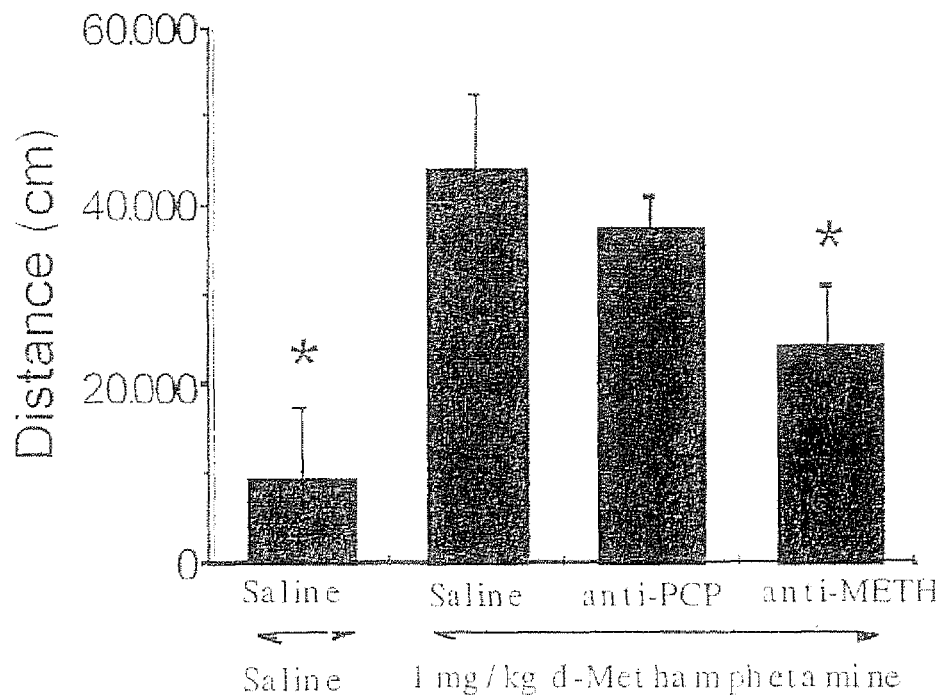
FIG. 15A further shows the distance travel from 30 minutes after saline or d-methamphetamine administration until the end of the experiment, 4.5 hours later. *$p<0.05$ compared to a 1 mg/kg dose of methamphetamine followed by the saline control treatment. †$p<0.05$ compared to a 1 mg/kg dose of methamphetamine followed by the anti-methamphetamine Fab treatment.
Figure 15B:
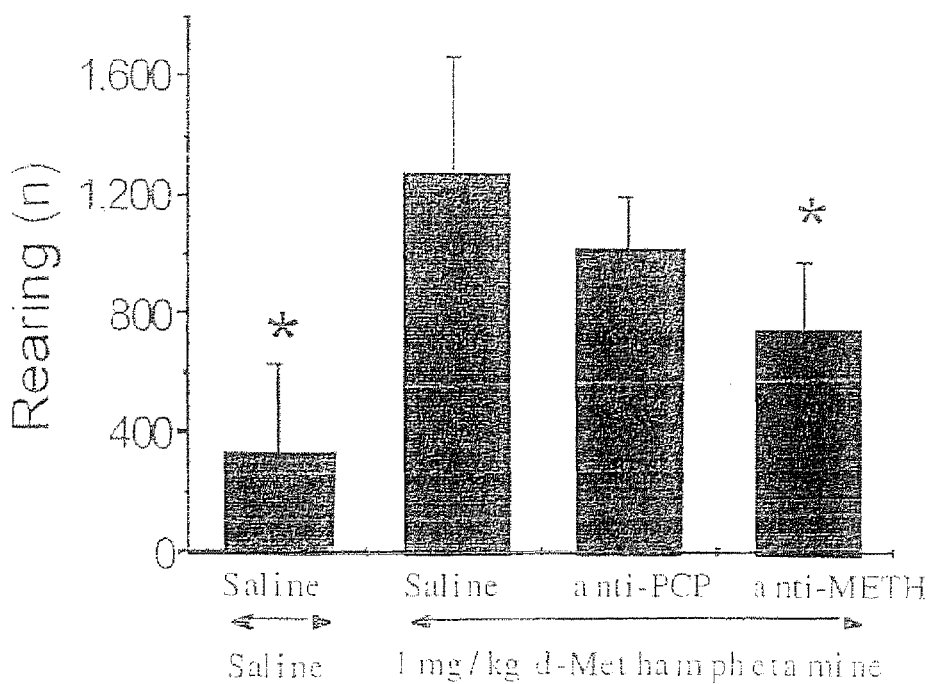
FIG. 15B further shows the number of methamphetamine-induced rearing events from 30 minutes after saline or d-methamphetamine administration until the end of the experiment, 4.5 hours later. At the 30 min the animals were treated with ether saline, anti-phencyclidine Fab or anti-d-methamphetamine Fab. *$p<0.05$ compared to a 1 mg/kg dose of methamphetamine followed by the saline control treatment.

Based on the distance traveled parameter, the duration of action of methamphetamine-induced effects following a 1 mg/kg iv dose was about two hours (116±17 min). After treatment with anti-PCP Fab the duration of activity was 111±10 min. After treatment with anti-methamphetamine Fab the duration of activity was 75±22 min. Both the distance traveled (FIG. 15A) and the number of rearing events (FIG. 15B) were significantly different from the behaviors produced by saline followed by methamphetamine administration (p<0.05). The anti-PCP Fab treatment produced some mild reductions in methamphetamine-induced locomotor activity, which were similar to the mild reductions in behavior we have found in other experiments in which polyclonal non-specific antibody is used to treat PCP-induced locomotor activity. As a percentage of the control saline treatment, the monoclonal anti-methamphetamine Fab produced a 55% decrease in the distance traveled (FIG. 15A). The number of rearing events (FIG. 15B) and the time spent moving (results not shown) were also decreased by 55% and 60%, respectively.

Since the monoclonal antibody used for these studies did not significantly bind to d-amphetamine (a psychoactive metabolite present at very high levels in the rat, but at significantly lower levels in the human) and it was a low affinity antibody (about 250 nM), the therapeutic potential for antibody based medications for overdose are quite significant. This is especially important since no therapies currently exist. With the use of improved hapten design and production of antibodies with significantly lower $K_D$ values (e.g., <30 nM), this invention should provide a significant breakthrough in treatment of overdose due to d-methamphetamine-like drugs.

Example 12

Pretreatment With Anti-(+) Methamphetamine Monoclonal Antibody to Reduce the Effects of (+)Methamphetamine Drug Abuse Rats (n=7/group) were administered a dose of 502 mg/kg of anti-methamphetamine monoclonal antibody on day 1. The following day they were administered i.v. (+)methamphetamine (1.0 mg/kg) 3 days apart on two occasions to stabilize locomotor responses and to minimize sensitization. Then 1.0 mg/kg of (+)methamphetamine was administered i.v. As shown in FIG. 16, the high-affinity anti-(+) methamphetamine monoclonal antibody significantly (P<0.05) reduced (+)methamphetamine induced effects by 42% for distance traveled (left) and by 51% for rearing events (right). The monoclonal antibody significantly shortened the duration of action of (+)methamphetamine from about 160 to 80 min. Saline control treatments conducted before and after the experimental protocol showed that baseline activity was stable over an extended period.

Example 13

Impact of Anti-D-Methamphetamine Therapy on Drug Self-Administration and Drug Discrimination as a Measure of Treating Long-Term Addiction This example describes the ability of anti-d-methamphetamine antibody to alter the d-methamphetamine dose-response curve for the discriminative stimulus effects of d-methamphetamine, thereby demonstrating possible therapeutic usefulness of antibody treatment for methamphetamine abuse.

One of the problems in designing experiments to determine if antibody treatment affects drug discrimination is that antibodies have a very long duration of action (Proksch et al, 2000). For example, the half life of a monoclonal IgG in rats is about 8 days (Bazin-Redureau et al, 1997). If the same animals are used to determine the effects of drug doses before and after antibody treatment, the presence of the antibody might disrupt further drug-discrimination training through antibody binding of the training dose and reduced access of the training dose to the brain. Should this occur, maintenance of drug-discrimination control by (+)-methamphetamine might erode. Therefore, (+)-amphetamine and cocaine were used in addition to (+)-methamphetamine as training drugs in some experiments. These drugs do not cross react with (+)-methamphetamine-specific antibodies and either of these drugs can substitute for that drug as a discriminative stimulus. Thus the specificity of the anti-(+)-methamphetamine antibody should allow continued discrimination training using cocaine or (+)-amphetamine as the training drug.

In addition, the discriminative stimulus effects of (+)-methamphetamine, (+)-amphetamine, and cocaine were compared in rats and pigeons using several routes of drug administration. After determination of the dose-response curves for these drugs, anti (+)-methamphetamine antibodies were given intravenously and all or portions of the (+)-methamphetamine dose-response curves were redetermined. In pigeons, the dose-response curves for (+)-amphetamine and cocaine were determined before and after the administration of antibody to determine the in vivo specificity of an anti (+)-methamphetamine antibody in blocking the discriminative stimulus effect of (+)-methamphetamine. Dose-response curves for (+)-amphetamine were also determined after administration of this antibody to rats.

Animal Protocols for Example 13

A total of 16 adult male Sprague Dawley rats were employed. Three rats performed poorly during drug discrimination training and two others died before sufficient data were collected. Therefore, the rodent data presented are based on 11 rats, as shown in Table 2. All rats were maintained at body weights of approximately 300 g by food pellets earned during test sessions, and supplemental feeding after test sessions and on days when the rats were not tested.

A total of 8 male White Carneau pigeons were used in these experiments. Four of the pigeons had performed extensively in previous experiments on drug discrimination (L1 and McMillan, 2001; McMillan et al., 2001b), including experiments in which the discrimination of amphetamines had been studied. These birds were maintained at 80-85% of their free-feeding weights (range 429-510 g). The second group of four birds also had performed in previous drug-discrimination experiments (McMillan et al, 2001a), although (+)-amphetamine was not used as a training drug in these experiments until the present experiments.

Water was freely available in the home cages of both rats and pigeons and the vivarium was temperature and humidity controlled with a light cycle from 0700 to 1900 and a dark cycle from 1900 to 0700. Training and testing of both species occurred between 0900 and 1200.

Rats were tested in two-lever operant chambers (Gerbrands Model 7400) enclosed in sound-attenuating chambers (Gerbrands Model 7200). Each chamber contained a house light on the chamber ceiling and stimulus lights over the two levers mounted on the front panel of the chamber. A pellet dispenser delivered 97 mg Noyes food pellets into a cup centered between the levers. Masking noise and air circulation were provided by a fan mounted in the rear wall of the sound-attenuating chamber. Programming and recording were accomplished by a MED Associates interface and microcomputer located in an adjacent room.

Testing Procedures for Example 13

Rats were conditioned to lever press by autoshaping. After responding was established when lights above the right lever were lighted during one session, responses produced food pellets until 25 pellets had been delivered. In the next session a similar procedure was followed for the left lever. Subsequently, the lights above both levers were lighted and discrimination training began. Prior to training sessions, rats were administered a drug or 0.9% saline solution and placed in the operant chamber for 10 min after which the session began. The different training drugs, doses and routes of administration employed for the three groups of rats are shown in Table 2.

TABLE 2

Testing Of Rats And Pigeons Before And After mAb6H8 Administration

| GROUP | Training Drug and Dose | n | Testing Condiditons |
|---|---|---|---|
| Rat I | 2 mg/kg (+) METH[a] | 4 | IV and IP (+) METH DRCs pre antibody IV (+) METH doses days 1 and 4 after antibody IP (+) METH doses on days 1 and 4 after second antibody administration |
| Rat II | 5 mg/kg Cocaine | 3 | IV and IP (+) METH 1 day after antibody IV (+) METH days 1 and 7 after a second antibody administration |
| Rat III | 10 mg/kg Cocaine | 4 | Cumulative IP DRCs for Cocaine, (+) METH and (+) AMP Cumulative IV DRCs for (+) METH |
| Pigeon I | 2 mg/kg (+) AMP | 4 | Cumulative iM DRCs for Cocaine, (+) METH, and (+) AMP IM (+) METH DRCs days 1 and 8 pose antibody |
| Pigeon II | 3 mg/kg (+) AMP | 4 | Cumulative IM DRCs for Cocaine, (+) METH and (+) AMP IM (+) METH DRCs day 2 and 7 post antibody |

(+) METH = (+)-methamphetamine;
(+) AMP = (+)-amphetamine;
DRC = dose-response curve;
IV = intravenous drug administration;
IP = intraperitoneal drug administration
IM = intramuscular drug administration
One rat in group Rat I was trained with 1 mg/kg rather that 2 mg/kg (+)-methamphetamine Rats were tested until responding stabilized at more than 90% of responding on the drug key after the training drug and less than 10% of responding on the drug key after saline. After responding stabilized, dose-response curves were determined for all rats for (+)-methamphetamine by both the intravenous (IV) and intraperitoneal (IP) routes before administration of the antibody. For rats in Groups I and II, single points on the dose-response curve were determined on Tuesdays and Fridays with additional training occurring on other week days. For rats in Group III cumulative dose-response curves were determined on Fridays, with additional training on other week days. Testing did not occur on Saturday or Sunday.

On test days for Groups I and II, rats were given a dose of drug and then placed in the test cage for 10 min, after which the session began. The session terminated whenever the animal completed 20 responses on one of the two levers, or after 40 min, whichever occurred first. On test days for Group III, rats were treated similarly, except that after the first food pellet was consumed, the rats were removed from the test chamber and a second dose was given. The rats were then returned to the test chamber and 10 min later the session was reinitiated. This process of cumulative dosing continued until the animals no longer responded for a period of 10 min. The cumulative doses shown in the figures represent the sum of all doses given within the session.

The pigeons used in these experiments had performed in experiments previously. Those in pigeon Group I had been used most recently in an experiment where the birds were trained using 4 response keys to discriminate among saline, 5 mg/kg pentobarbital, 5 mg/kg morphine and 2 mg/kg (+)-amphetamine. In these experiments, responses on the correct key were reinforced under a fixed-ratio 20 schedule of food presentation (Li and McMillan, 2001). These birds continued to be trained and tested in this same chamber, except that training sessions with pentobarbital and morphine were discontinued, while those with 2 mg/kg (+)-methamphetamine and saline continued.

On training days, (+)-amphetamine or saline was injected into the breast muscle and the bird was placed in the test chamber for 10 min, after which the chamber and the response keys were illuminated and the session was initiated. Training continued for 40 min or until the pigeons had received 20 reinforcers, whichever occurred first. Once a week, a cumulative dose-response curve was determined for cocaine, (+)-amphetamine, or (+)-methamphetamine. In the determination of cumulative dose-response curves, a dose of drug was administered and the pigeon was placed in the chamber for 10 min, after which the chamber and key lights were illuminated. The pigeon was tested for 5 min or until one food reinforcer had been delivered, whichever occurred first. Food was delivered following the completion of 20 responses on one of the two keys. After food had been delivered, or the session had timed out, the bird was removed from the chamber, a higher dose was administered, and the process was repeated. Cumulative dosing continued until the pigeon failed to respond during a 5-min period.

In other experiments with some of these pigeons, cumulative dose-response curves were determined for (+)-methamphetamine before, and at 1 and 8 days after, administration of the mAb6H8 antibody (pigeon Groups 1 and 2) or at 1 and 4 days after the administration of the mAb6H4 antibody (pigeon Group 2). Because only a few birds were still available for these experiments, the data for days 1-2 and days 7-8 were combined.

Drugs Used for Example 13

(+)-methamphetamine, (+)-amphetamine and cocaine were purchased from Sigma Chemical Co. as the hydrochloride salts. All doses are expressed as the salts. Drugs were dissolved in physiologic saline solution such that doses could be administered in a volume of 0.1 ml/100 g of body weight. Injections were given i.v. or i.p. to rats and intramuscularly to pigeons 10 min before test sessions. The anti (+)-methamphetamine antibody was administered at least one day before determining the discriminative stimulus effects of drugs.

Data Analysis for Example 13

The percentage of responses on the drug key during training sessions were averaged across animals and a standard deviation was plotted around these means. Dose-response curves before and after administration of the antibodies were compared using a repeated measures analysis of variance.

Results for Example 13

After responding stabilized, the baseline performance of the three groups of rats during training sessions was not significantly different, indicating that stimulus control was equivalent across the three groups. Although a two-way repeated measures ANOVA for i.v. dose-response curves for (+)-methamphetamine in groups I and II was statistically significant, subsequent Tukeys tests revealed no additional significant differences between groups, nor were there statistically significant differences in dose-response curves across groups when drugs were administered by the i.p. route. Therefore, data from the rats trained with (+)-methamphetamine and cocaine were combined for the determination of dose-response effects to increase group size.

Figure 17:
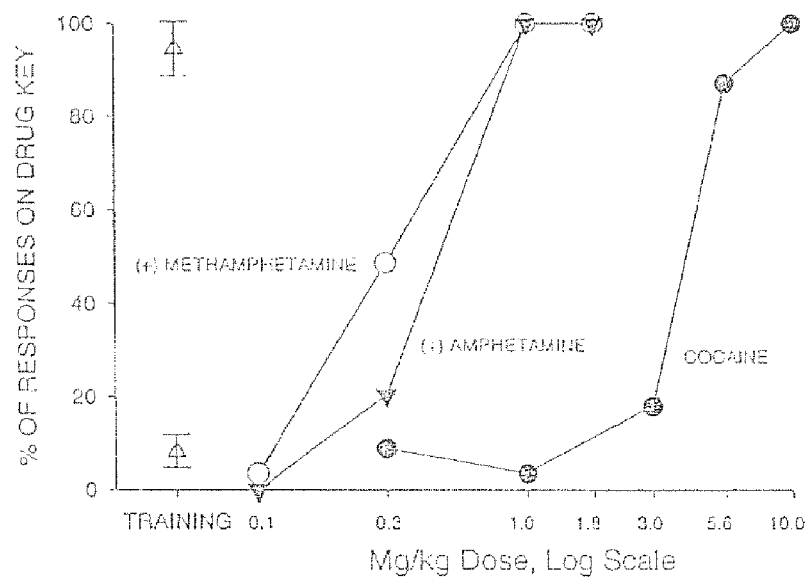
FIG. 17 shows cumulative i.p. dose-response curves for (+)-methamphetamine, (+)-amphetamine and cocaine in rats trained to discriminate 10 mg/kg cocaine from saline (Table 2, Rat Group III). Abscissa: Mg/kg dose on a log scale. Ordinate: Percentage of responses on the drug (cocaine) key. Each point on the (+)-methamphetamine and (+)-amphetamine dose-response curves represents single observations in the same four rats, while points on the cocaine dose-response curves represent duplicate observations in the same rats. Brackets at TRAINING show+/−one standard deviation around mean for six training sessions with saline and six training sessions with cocaine after responding stabilized.

FIG. 17 compares the discriminative stimulus effects of i.p. doses of (+)-methamphetamine, (+)-amphetamine and cocaine in the rats from group III. Low doses of all three drugs produced responding on the saline key, while higher doses of these drugs produced responding on the drug key. (+)-Methamphetamine and (+)-amphetamine were nearly equipotent as discriminative stimuli, but cocaine was only about one-tenth as potent as the amphetamines.

Figure 18:
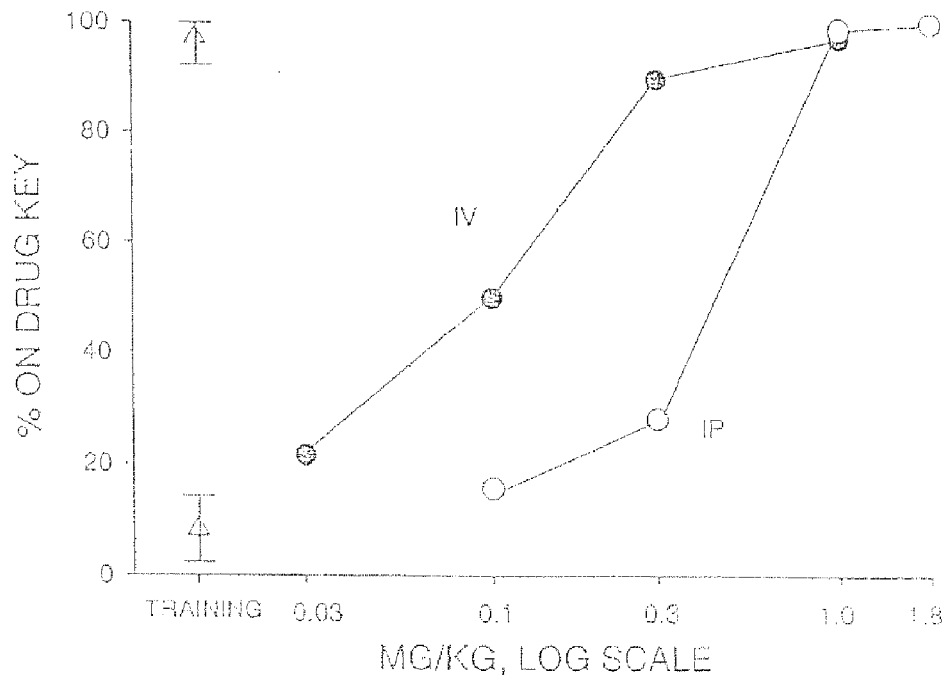
FIG. 18 shows cumulative dose-response curves for i.v. and i.p. (+)-methamphetamine in rats. Abscissa: Mg/kg (+)-methamphetamine on a log scale. Ordinate: Percentage of responses on the drug key. Each point represents single observations in each of eleven rats. The rats were trained to discriminate between saline and 10 mg/kg cocaine, or 5 mg/kg cocaine, or 1 or 3 mg/kg (+)-methamphetamine (see Table 2). Brackets at TRAINING represent six training sessions after saline and six training sessions after drug after responding stabilized.

FIG. 18 shows a comparison between the effects of i.v. and i.p. doses of (+)-methamphetamine conducted in all 11 rats. At low doses of (+)-methamphetamine responding was confined largely to the saline key. As the dose of (+)-methamphetamine increased, responding shifted to the drug key. Intravenous (+)-methamphetamine was approximately 3 times more potent than i.p. (+)-methamphetamine.

Figure 19:
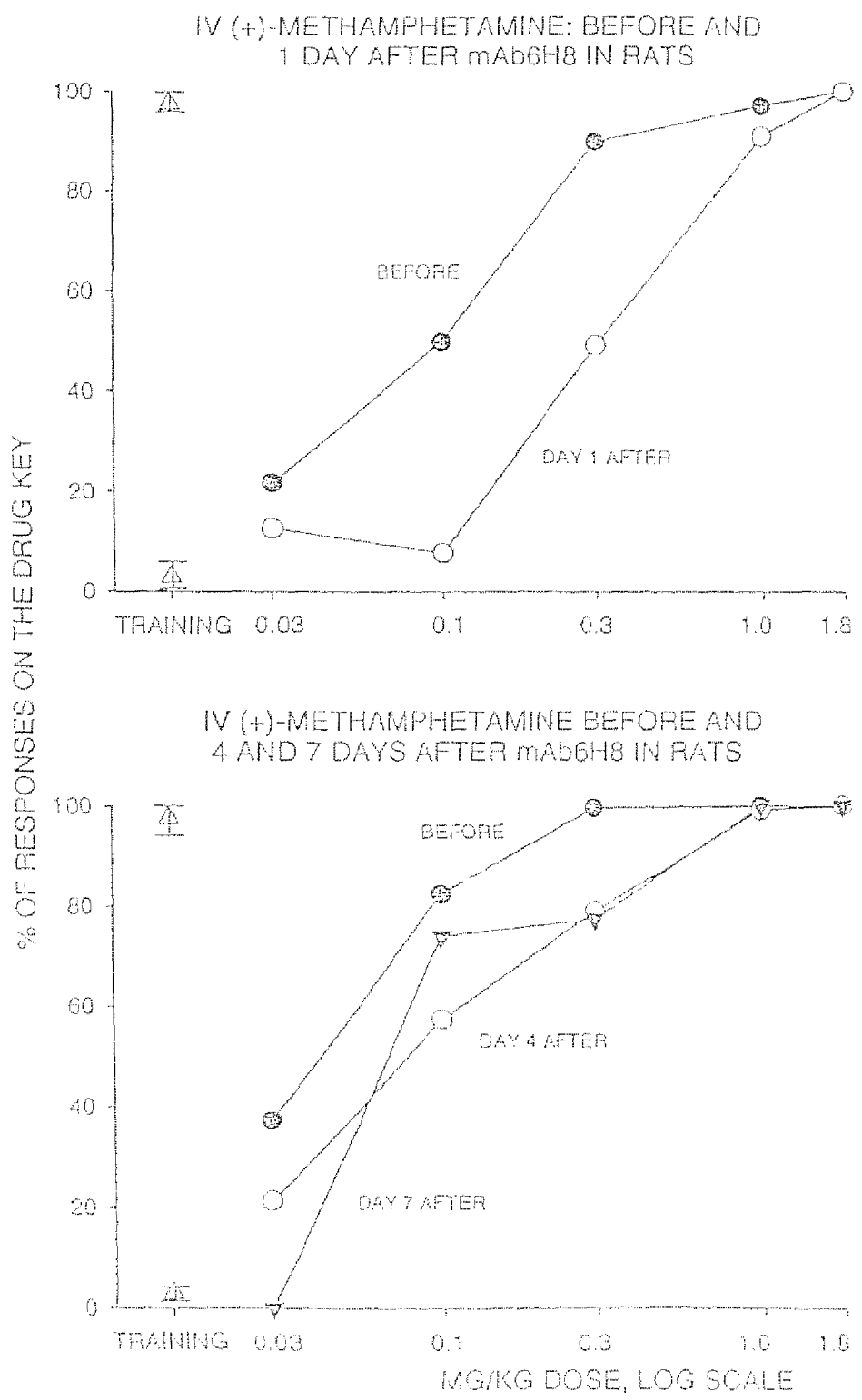
FIG. 19 shows dose-response curves for i.v. (+)-methamphetamine before and 1 day after treatment with 1 g/kg of the mAb6H8 antibody in rats (top panel) or before and 4 and 7 days after the antibody treatment (bottom panel). Abscissa: Mg/kg (+)-methamphetamine on a log scale. Ordinate: percentage of responses on the drug key. All 7 rats from Groups I and II (Table 2) contributed to the dose-response curves in the top panel, but only 5 of these rats contributed to the data in the bottom panel. Brackets at TRAINING represent six training sessions after saline and six training sessions after drug after responding stabilized.

The top frame of FIG. 19 shows the effects of i.v. (+)-methamphetamine before and 1 day after the administration of the low-affinity mAb6H8, and the bottom frame shows data from the same rats before and 4 and 7 days after administration of the mAb6H8. Administration of the antibody shifted the (+)-methamphetamine dose-response curve approximately 3-fold to the right (top frame) on the day after administration of the antibody. A one-way repeated measure ANOVA showed the dose response curves to be significantly different. The bottom frame of FIG. 19 shows the dose-response curves for i.v. (+)-methamphetamine at 4 and 7 days after administration of the antibody. Both dose-response curves after the antibody were significantly shifted to the right (p<0.05).

Figure 20:
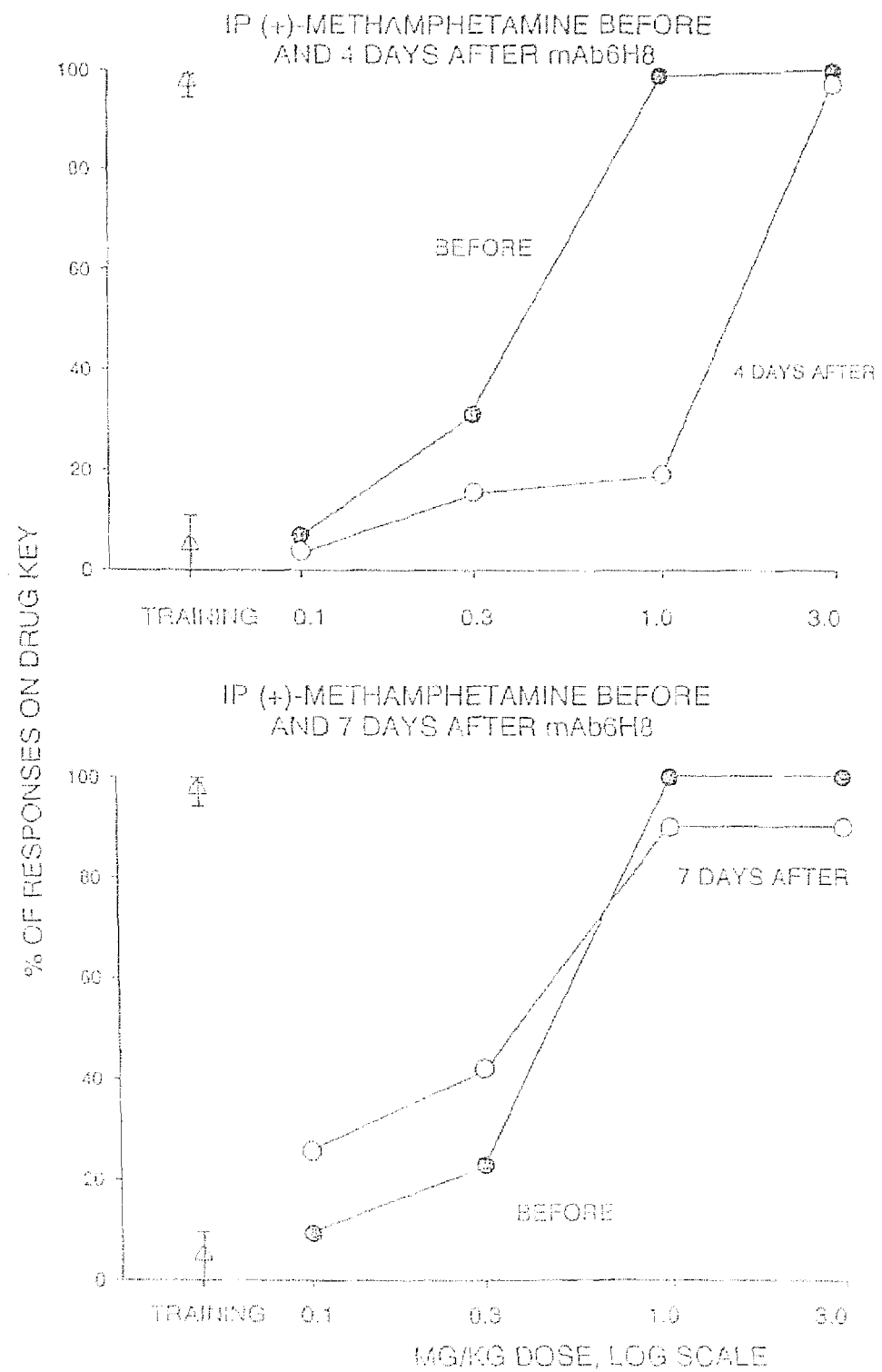
FIG. 20 shows dose-response curves for i.p. (+)-methamphetamine before and 4 days (top panel) or 7 days (bottom panel) after treatment with 1 g/kg of the mAb6H8 in rats. Abscissa: Mg/kg (+)-methamphetamine on a log scale. Ordinate: Percentage of responses on the drug key. All 7 rats from Groups I and II (Table 2) contributed to the data in the bottom panel, but only 5 of these rats contributed to the data in the top panel. Brackets at TRAINING represent six training sessions after saline and six training sessions after drug after responding stabilized.

FIG. 20 shows the i.p. (+)-methamphetamine dose-response curve before and 4 days (top frame) and 7 days (bottom frame) after administration of mAb6H8. At 4 days after administration of the antibody the (+)-methamphetamine dose-response curve was shifted approximately 3-fold to the right, a shift that was statistically significant (p=<0.05) by a repeated measures ANOVA. By day 7 there was no significant difference between the before and after dose response curves.

Figure 21:
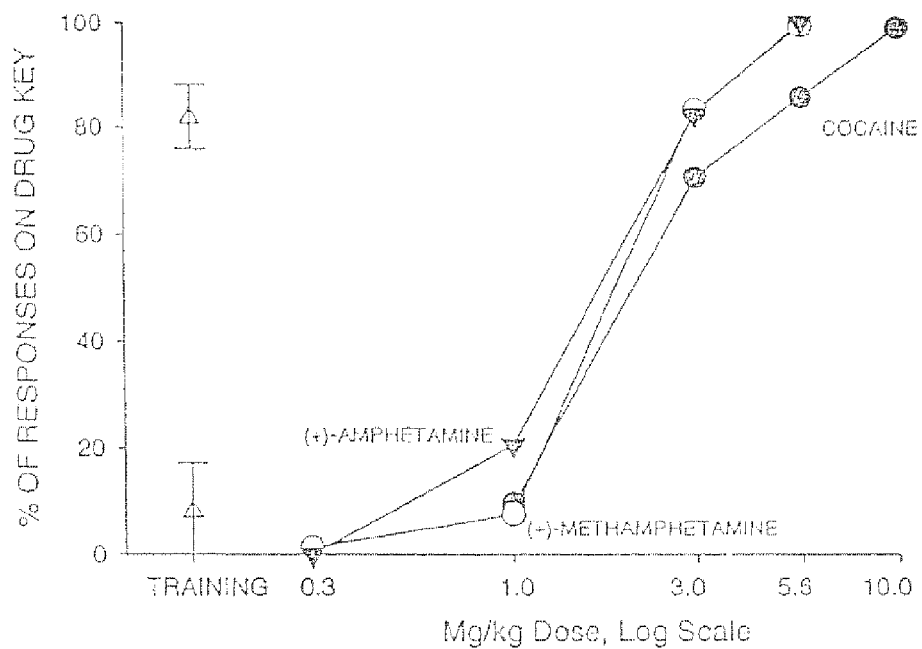
FIG. 21 shows cumulative i.m. dose-response curves for (+)-methamphetamine, (+)-amphetamine and cocaine in pigeons trained to discriminate 2 or 3 mg/kg (+)-amphetamine from saline. Abscissa: Mg/kg dose on a log scale. Ordinate: Percentage of responses on the drug [(+)-amphetamine] key. Each point on the dose-response curves represents duplicate observations in the pigeons in Group I and single observations in pigeons in Group II (Table 2), except at the highest dose of each drug where only 3 or 4 birds responded. Brackets at TRAINING show+/−one standard deviation around mean for six training sessions with saline and six training session with cocaine after responding stabilized.

FIG. 21 shows the effects of intramuscular injections of (+)-methamphetamine, (+)-amphetamine, and cocaine in pigeons trained to discriminate 2 or 3 mg/kg (+)-amphetamine from saline. Low doses of all drugs produced responding primarily on the saline key and higher doses produced responding on the drug key. (+)-Methamphetamine and (+)-amphetamine were approximately equipotent, while cocaine was about one-third as potent as the amphetamines.

Figure 22:
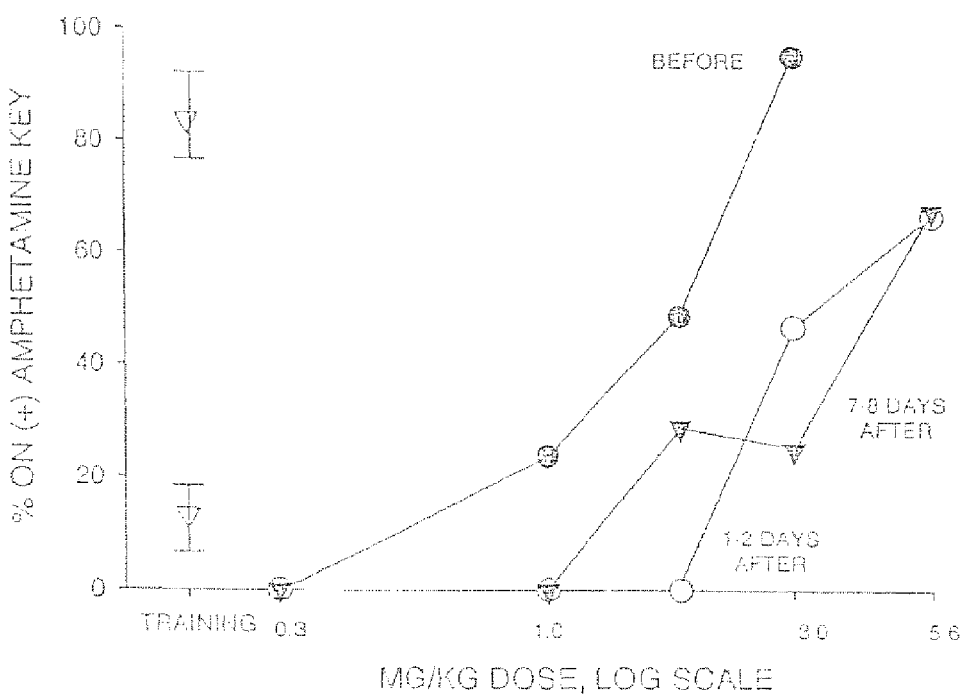
FIG. 22 shows dose-response curves for i.m. (+)-methamphetamine before and 1 and 2, or 7 and 8 days after treatment with 1 g/kg of mAb6H8 in pigeons. Abscissa: Mg/kg (+)-methamphetamine on a log scale. Ordinate: Percentage of responses on the drug key. Two pigeons from Pigeon Group 1 and four pigeons from Pigeon Group 2 contributed to these experiments. Brackets at TRAINING represent six training sessions after saline and six training sessions after drug after responding stabilized.

FIG. 22 shows the effects of intramuscular doses of methamphetamine in pigeons at 2 and 7 days after administration of mAb6H8. At 2 days after the antibody, the (+)-methamphetamine dose-response curve was shifted slightly downward and to the right relative to its original position. At 7 days after mAb6H8 the shift was 3-10 fold.

Figure 23:
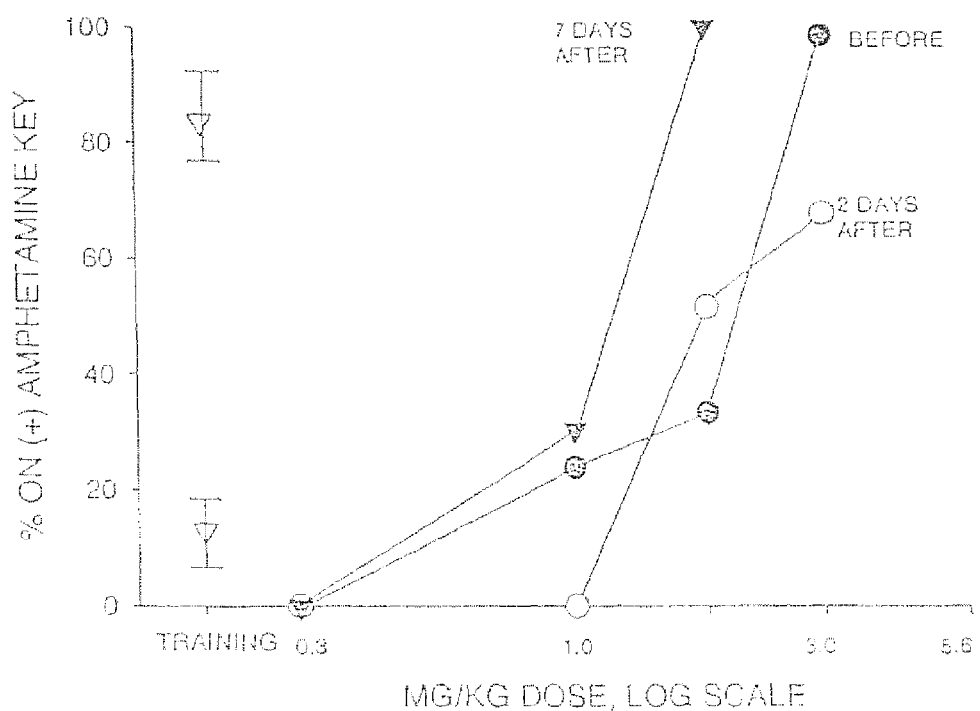
FIG. 23 shows dose-response curves for intramuscular (+)-amphetamine before and 2 or 7 days after treatment with 1 g/kg of mAb6H8 in pigeons. Abscissa: Mg/kg (+)-amphetamine on a log scale. Ordinate: Percentage of responses on the drug key. Two pigeons from Pigeon Group 1 and four pigeons from Pigeon Group 2 contributed to these experiments. Brackets at TRAINING represent six training sessions after saline and six training sessions after drug after responding stabilized.

FIG. 23 shows the effects of intramuscular (+)-amphetamine in pigeons at 2 and 7 days after mAb6H8. The dose-response curves at 2 and 7 days after mAb6H8 for (+)-amphetamine were not statistically different. The dose-response curve for responding on the drug key reached a peak at a lower dose of (+)-amphetamine 7 days after than it had before the antibody was given.

FIG. 24 shows the effects of i.v. and i.p. cocaine in rats before and 1 day after mAb6H8 (top frame) and the effects of i.m. cocaine in pigeons before and 1 day after the antibody (bottom frame). The cocaine curves were not shifted after administration of the antibody in either rats or pigeons.

Figure 25:
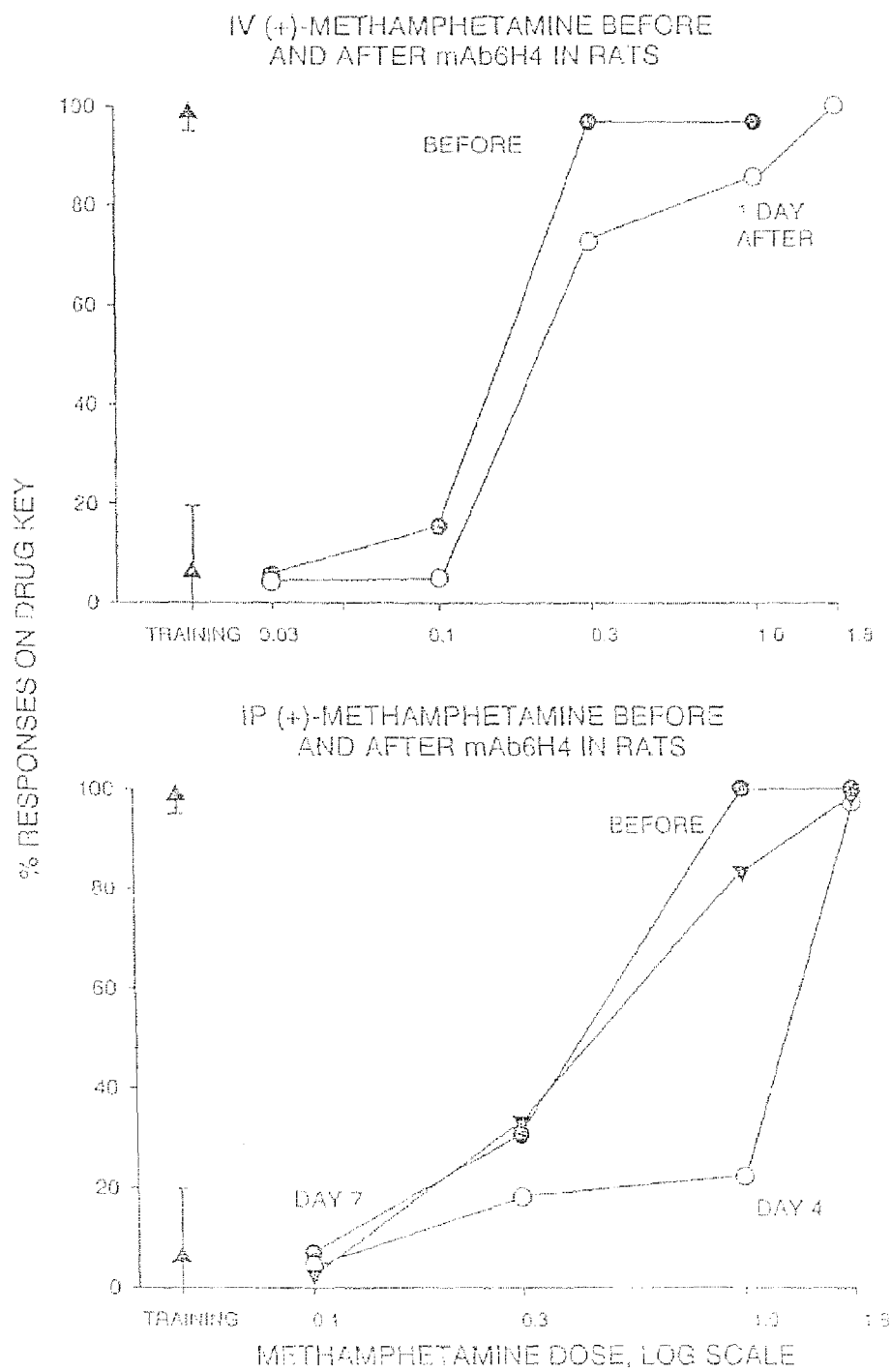
FIG. 25 shows dose-response curves for i.v. (+)-methamphetamine 1 day (top panel) or 4 and 7 days after the administration of mAb6H4 in rats. Abscissa: Mg/kg (+)-methamphetamine on a log scale. Ordinate: Percentage of responses on the drug key. Brackets at TRAINING show +/−one standard deviation around mean for six training sessions with saline and six training session with cocaine after responding stabilized.

FIG. 25 shows the effects of intravenous administration of (+)-methamphetamine to rats before and 1 day after (top frame) and at days 4 and 7 after the administration of the high-affinity mAb6H4 anti-methamphetamine antibody. The antibody shifted the (+)-methamphetamine dose-response curve slightly to the right 1 day after its administration. At day 4 the dose-response curve was shifted to the right by 3-10 fold. By day 10 after administration of the mAb6H4 the methamphetamine dose-response curve was close to its original position.

Figure 26:
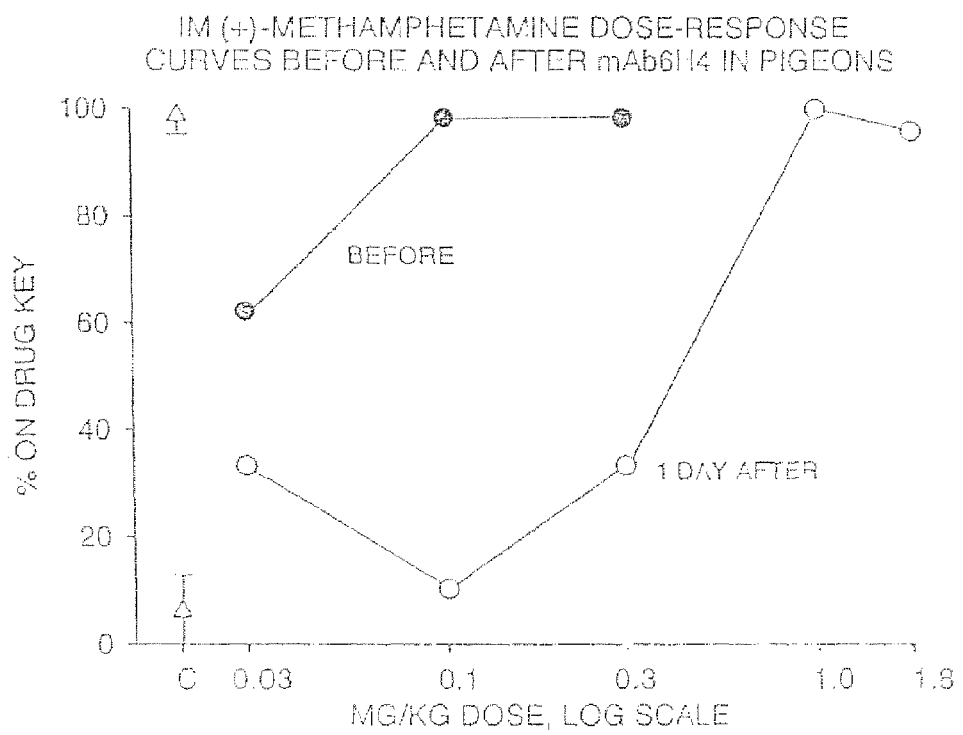
FIG. 26 shows dose-response curves for intramuscular (+)-methamphetamine before and 1 day after 1 g/kg of mAb6H4 in pigeons. Abscissa: Mg/kg (+)-methamphetamine on a log scale. Ordinate: Percentage of responses on the drug key. Three pigeons from Pigeon Group 2 contributed to these experiments. Brackets at TRAINING show +/−one standard deviation around mean for six training sessions with saline and six training session with (+)-amphetamine after responding stabilized.

FIG. 26 shows the i.m. dose-response curves for (+)-methamphetamine before and 1 day after administration of the high-affinity mAb6H4 in pigeons. The antibody shifted the dose response curve to the right by approximately 10-fold.

These results show that a low affinity ($K_D$=250 nM) anti-(+)-methamphetamine monoclonal antibody (mAb6H8) shifted the (+)-methamphetamine dose-response curve to the right by about one-half log unit. This effect was robust since it occurred in both rats and pigeons, it occurred after intravenous (rats), intraperitoneal, (rats) and intramuscular (pigeons) routes of (+)-methamphetamine administration, and it occurred when different training doses of (+)-methamphetamine, cocaine, and (+)-amphetamine were used during discrimination training. A similar shift was shown with the high affinity mAb6H4 antibody ($K_D$=10 nm).

Although only two rats and two pigeons were available to study the discriminative stimulus effects of (+)-amphetamine and cocaine before and after the administration of the mAb6H8 antibody, the failure of the anti (+)-methamphetamine antibody to shift the dose-response curves for the discrimination of either of these drugs given by several routes of administration suggests that its effects were specific for (+)-methamphetamine. The failure of the antibody to block the effects of cocaine were observed using two different routes of cocaine administration in rats (i.v. and i.p.) and by a third route in pigeons (i.m.). Therefore, despite the small number of animals used in these experiments, the generality of these findings was established. Although (+)-methamphetamine and (+)-amphetamine differ little in chemical structure and in their potency as discriminative stimuli, mAb6H8 has an approximate 2,000 times lower affinity for (+)-amphetamine, so the failure of the antibody to shift the (+)-amphetamine dose-response curve was not unexpected.

Preliminary data suggest that (+)-methamphetamine and (+)-amphetamine are nearly equipotent as discriminative stimuli in the rat. This represents a potential problem because in rats a considerable fraction of (+)-methamphetamine is metabolized to (+)-amphetamine. In fact, in the rat peak plasma levels of (+)-amphetamine are obtained within 20 min after intravenous administration of (+)-methamphetamine (Riviere et al., 1999; 2000). Conversion of (+)-methamphetamine to (+)-amphetamine in rats might explain why the shift in the (+)-methamphetamine dose-response curve was only modest in rats. It is possible that much of the (+)-methamphetamine not bound to the antibody was metabolized to (+)-amphetamine. Since the discriminative stimulus properties of (+)-methamphetamine and (+)-amphetamine are difficult to separate, the formation of (+)-amphetamine might have limited the degree to which mAb6H8 could shift the (+)-methamphetamine dose-response curve in rats. In pigeons, the anti (+)-methamphetamine antibody also shifted the (+)-methamphetamine dose-response curve about one-half log unit to the right. The metabolism of (+)-methamphetamine in pigeons is not known.

The effects of mAb6H8 lasted for a week or longer in both rats and pigeons. The half life of mAb6H8 is 7-8 days. Previous studies with anti-phencyclidine IgG antibodies have shown a functional elimination half-life of 15.4 days, which produced significant reductions in brain phencyclidine for at least 27 days (Proksch et al., 2000). The behavioral data suggest an extended functional half-life for the anti-(+)-methamphetamine antibody, but not as long as the anti-phencyclidine MAb.

In these experiments, (+)-methamphetamine, cocaine, and (+)-amphetamine were used as training drugs, and some times at different doses. Differences in dose-response curves for these drugs that were dependent on the training drug or the training dose were not observed. The fact that the dose-response curve for (+)-methamphetamine in the presence of mAb6H8 consistently shifted to the right by approximately one-half log unit despite the differences in the training drug and training dose only strengthens the generality of the findings.

In the present experiments (+)-methamphetamine and (+)-amphetamine were found to be equipotent as discriminative stimuli in rats trained to discriminate 10 mg/kg cocaine from saline. Both the amphetamines were approximately 10 times more potent than cocaine (FIG. 17). These data are similar to previous reports on the relative potency of cocaine and the amphetamines as discriminative stimuli in rats. In previous studies in cocaine-trained rats, (+)-methamphetamine and (+)-amphetamine have ranged from 3-30 times more potent than cocaine as a discrimininatve stimulus. In (+)-methamphetamine trained rats, methamphetamine was 10 times more potent than cocaine. In pigeons in the present study, (+)-methamphetamine and (+)-amphetamine also were approximately equipotent, but the amphetamines were only 2-3 times more potent than cocaine. This is similar to a previous report in pigeons trained to discriminate cocaine from saline, where little difference was found between the potency of cocaine and (+)-amphetamine. Although the present study found less difference in potency between the amphetamines and cocaine, it is possible that this difference relates to differences in the training drugs rather than the species in the present study. The rats in which the dose-response curves were determined were trained to discriminate 10 mg/kg cocaine from saline, while the pigeons in which the dose-response curves were determined were trained to discriminate 3 mg/kg (+)-amphetamine from saline.

The potency of intravenous and intraperitoneal (+)-methamphetamine was also compared in rats. These experiments were performed because preliminary experiments with the anti (+)-methamphetamine antibody suggested that it was more difficult to shift the (+)-methamphetamine dose-response in the presence of the antibody when the (+)-methamphetamine was administered intravenously instead of intraperitoneally. When more animals were tested, this observation did not hold up. However, it was established that intravenous (+)-methamphetamine was approximately 3 times more potent as a discriminative stimulus than intraperitoneal (+)-methamphetamine in rats trained to discriminate cocaine from saline.

The degree to which the 6H8 anti-(+)-methamphetamine mAb shifted the drug discrimination curve for (+)-methamphetamine was modest. Presumably, the effectiveness of the antibody would be related to its affinity (250 nM), capacity, and the on-off rates of mAb binding to (+)-methamphetamine. The mAb6H8 antibody is a low affinity antibody. Antibodies with significant improvements in the affinity constant and specificity should be more effective than mAb6H8. The high affinity mAb6H4 did appear to produce a greater shift in the dose-response curve for (+)-methamphetamine in pigeons than mAb6H8 did. The research with both mAb6H8 and mAb6H4 illustrates that anti-(+)-methamphetamine monoclonal antibodies are capable of blocking pharmacological effects of (+)-methamphetamine that are relevant to its abuse.

Example 14

Effect of Antibody-Based Therapy on D-Methamphetamine Toxicity in Large Animal Model A battery of pharmacokinetics studies and behavioral tests can be conducted to determine whether anti-d-methamphetamine Fab can reverse acute behavioral toxicity due to d-methamphetamine in large animals like large dogs or primates. These data will help to determine the ability of anti-d-methamphetamine Fab to redistribute d-methamphetamine in a large animal model and help to scale-up the therapy to humans. d-Methamphetamine can be administered to male dogs (or primates; n=6 per group, 3 males and 3 females) at 0.3 mg/kg or higher depending on results of preliminary d-methamphetamine dose-response studies. If needed for quantitation, a tracer dose of $[^3H]$-d-methamphetamine can also be administered. After the drug is fully distributed (e.g., 30-45 min), anti-d-methamphetamine Fab is administered at a 1.0 mol-eq dose to the amount of d-methamphetamine remaining in the dog (or primate) at 30 min. The exact timing and dosing depend on the outcome of the rat studies and preliminary pharmacokinetic studies in dogs or primates. Plasma and urine d-methamphetamine pharmacokinetics can be determined in each dog or primate as described above.

The same dogs (or primates) should be used for the pharmacokinetic and behavioral studies for continuity. However, the success of the experiments is not dependent on using the same dog (or primate) for all experiments (n=6). For the behavioral experiments, d-methamphetamine are administered to dogs (or primates) at 0.3 mg/kg (or higher) followed 30-45 min later by a 0.1, 0.3, or 1.0 mol-eq dose of anti-d-methamphetamine Fab. The experiments are done in a pre-determined repeated-measures, mixed-sequence design. The same measures of behavior (and the EthoVision system) as described above can be used in the studies of d-methamphetamine acute toxicity.

Example 15

Hapten Design and Antibody Selection

When generating monoclonal antibodies (mAb, plural and singular) against small molecules, the chemical composition and molecular orientation of the drug-like hapten on the antigen is a crucial determinant, as shown herein. This is especially important when attempting to discover therapeutic mAb against the drugs of abuse (+)-methamphetamine ((+)METH), (+)-amphetamine ((+)AMP) and the related compound (+)-3,4-methylenedioxymethamphetamine ((+)MDMA, the plus isomer in the racemic mixture known as MDMA or ecstasy). The goal of these studies was to design and synthesize (+)METH-like haptens with structural attributes that would make them effective for generating monoclonal antibodies for treating medical problems associated with these stimulant drugs of abuse.

For these studies, hapten spacers between (+)METH and the carrier protein were progressively lengthened from 4 to 10 atoms to increase the potential for greater interaction of the hapten with the antibody binding site and/or to increase flexibility of the spacer between the (+)METH backbone structure and the carrier. It was hypothesized that a progressive lengthening and flexibility of the spacer arm would lead to increased affinity and specificity due to increased access to the entire (+)METH-like structure. As a secondary strategy, the location of the linker attachment to the (+)METH structure (e.g., para and meta attachments) was varied in an attempt to elicit antibodies with different conformational selectivity for (+)METH-like compounds.

Chemicals and Drugs for Example 15.

All chemicals and protein antigens were purchased from Sigma (St. Louis, Mo.), unless otherwise noted. Enzymes and *E. coli* strains were purchased from Invitrogen (Carlsbad, Calif.). (+)-2', 6'-$^3$H(n)]methamphetamine ([$^3$H]-(+)METH; 23.5 Ci/mmol) and (±)-[2, 6-3H2(n)]-amphetamine ([$^3$H]-(±) AMP; 45 Ci/mmol) were obtained from the National Institute on Drug Abuse (Bethesda, Md.) after synthesis at the Research Triangle Institute (Research Triangle Park, N.C.). Other METH-like drugs used in this study were also obtained from the National Institute on Drug Abuse.

[$^3$H]-(+)METH was used as sent, but the [$^3$H]-(±)AMP was chromatographically separated to obtain [$^3$H]-(+)AMP for use in our studies of (+)AMP specificity. The separation was performed on a 150×4 mm (i.d.) 5 μm Crown Pak CR(+) column (Chiral Technologies Inc., Exton, Pa.). The mobile phase consisted of 0.1 M perchloric acid (Fisher Scientific) containing 10% (v/v) methanol. The column temperature was maintained at 15° C. The flow rate was 1.0 ml/min and the injection volume was 50 μL. Chromatographic peaks were detected using ultraviolet absorption detection at a wavelength of 210 nm. The retention times for [$^3$H]-(+)AMP and [$^3$H]-(−)AMP were 20.1 min and 24.4 min, respectively.

Haptens and Hapten-protein Conjugation for Example 15.

Five different stereospecific (+)-isomer (+)METH-like haptens were synthesized. All haptens were synthesized as HCl salts to aid in solubility, and stored as solids or powders until used. The chemical structures are shown in Table 3. The complete synthesis of one of the haptens ((+)METH P6) was previously reported (Byrnes-Blake et al., 2001, Int Immunopharmacol 1:329-338). Synthesis of an 8 carbon molecule spacer hapten was also attempted, but synthesis of this molecule proved more difficult than expected, so work on this hapten was postponed till a later date. The chemical names and abbreviations of the five haptens are:

(S)-(+)-4-(3-carboxypropyl)methamphetamine, (+)METH P4

(S)-(+)-4-(5-carboxypentyl)methamphetamine, (+)METH P6

(S)-(+)-4-(5-carboxypentyloxy)methamphetamine, (+)METH PO6

(S)-(+)-3-(5-carboxypentyloxy)methamphetamine, (+)METH MO6

(S)-(+)-3-(9-carboxynonyloxy)methamphetamine, (+)METH MO10

Each hapten was initially covalently bound to at least 2-3 different protein antigens and used for immunization of mice to test for anti-METH IgG response. The individual mouse and hapten-protein antigen combination that yielded the highest anti-(+)METH IgG titers was chosen for production of monoclonal antibodies (see details below). The following is a list of the hapten-protein conjugates that produced the mAb listed in Table 3: (+)METH P4 and (+)METH P6 conjugated to bovine serum albumin; (+)METH PO6 and (+)METH MO6 conjugated to Imject Supercarrier Immune Modulator (catonized BSA (cBSA), Pierce Biotech, Rockford, Ill.); (+)METH MO10 conjugated to ovalbumin (OVA).

All chemical reactions for covalent binding of the haptens to protein antigens followed the same general procedure. The haptens were first solubilized in either 0.1 M 2-[N-morpholino]ethanesulfonic acid buffer (pH 4.5) or dimethylformamide and then adjusted to pH 4.5 with HCl. All haptens were coupled to their respective protein antigens by a carbodiimide reaction using the cross-linker 1-ethyl-3-[3-dimethylaminopropyl]carbodiimide hydrochloride (Pierce Biotech). This chemical synthesis forms a peptide bond between the carboxyl group of the hapten linker arm and free amino groups of lysine side chains in the respective proteins. The reactions were conducted with continuous stirring under dark conditions at room temperature for 18 hrs. At the end of the reaction, all antigens were purified as described by Byrnes-Blake et al. (2003, Eur J Pharmacol 461:119-128). This purification involved dialysis against distilled water, phosphate-buffered saline (pH 7.4), and a final purification of the soluble fraction on a gel filtration column in phosphate-buffered saline (pH 7.4). Purified antigens were stored at −20° C. until needed.

Immunization, Screening, and Hybridoma Generation for Example 15.

Female BALB/c mice (Charles River Laboratories, Wilmington, Mass.) were used for all immunizations. For production of the (+)METH P6 mAb, mice were immunized subcutaneously in the hindquarters with 100 μg of the (+)METH P6 antigen emulsified 1:1 (v/v) in TiterMax adjuvant (CytRx Corporation, Norcross, Ga.) and boosted monthly with 50 μg of the antigen until a favorable titer was reached. For all other antigen immunizations, the mice were initially immunized in the hindquarters subcutaneously with 20-100 µg of antigen emulsified in Freund's complete adjuvant. The initial immunization was followed by a boost with 20-50 µg of antigen emulsified in Freund's incomplete adjuvant three weeks later followed by three boosts at six week intervals, until a favorable titer level was reached. Serum samples were taken via tail bleed periodically to measure anti-(+)METH IgG. Titers were measured by ELISA (enzyme-linked immunosorbant assay) using 96-well microtiter plates coated with the original hapten conjugated to a different protein. For example, if the original antigen was (+)METH-MO6-cBSA, (+)METH-MO6 conjugated to thyroglobulin was used to avoid selecting carrier protein-reactive antibodies. The screening for anti-(+) METH IgG response was conducted by a [$^3$H]-(+)METH radioimmunoassay (RIA), using (+)METH and (+)AMP as the inhibitors. After sufficient anti-(+)METH IgG titers were achieved, conventional hybridoma technology was utilized as described previously (Valentine et al., 1994, J Pharmacol Exp Ther 269:1079-1085). The hybridoma fusion partner for mouse B cells was cell line P3X63Ag8.653 (American Type Culture Collection, Manassas, Va.). IgG isotype and light chain identity was determined with a mouse antibody isotyping kit (Boehringer Mannheim, Indianapolis, Ind.).
Production and Purification for Example 15.

Monoclonal antibodies were produced in either a Cell-Pharm System 2500 hollow fiber bioreactor (Valentine et al., 1996, J Pharmacol Exp Ther 278:709-716); Unisyn Technologies, Inc., Hopkinton, Mass.) or in a Biostat B 10 liter bioreactor (Sartorius Corp, Edgewood, N.Y.). All antibodies were harvested and stored at −80° C. until purification. MAb were purified either by affinity chromatography using Protein-G Sepharose (Amersham Biosciences, Piscataway, N.J.), or ion exchange chromatography using SP Sepharose (Amersham Biosciences, Piscataway, N.J.) as described in Hardin et al. (1998, J Pharmacol Exp Ther 285:1113-1122), or a combination of the two methods. Following purification, all antibodies were concentrated and buffer exchanged into 15 mM sodium phosphate containing 150 mM sodium chloride (pH 6.5-7.5) as described in McMillan et al. (2002, Behav Pharmacol 13:465-473).
Determination of Immunochemical Specificity.

The cross-reactivity profiles of each mAb for methamphetamine, structurally related, and unrelated compounds, was determined by RIA in a manner similar to that described by Owens et al. (1988, J Pharmacol Exp Ther 246:472-478). An IC50 value for inhibition of [$^3$H]-(+)METH (and [$^3$H]-(+) AMP for the mAb generated against the (+)METH MO10 hapten) was determined for each ligand after fitting a sigmoidal curve to the data points. $K_D$ values for mAb were determined by the method of Akera and Cheng (1977, Biochim Biophys Acta 470:412-423).
Results for Example 15.

For these studies, the hapten spacers were progressively lengthened from 4-10 atoms to increase the potential for greater interaction of the METH-like structures with the antibody binding site and to increase the flexibility of the spacer. It was hypothesized that a progressive lengthening of the spacer arm would lead to increases in affinity due to improved access to the entire METH-like structure; and the different immobilized conformations would elicit antibodies having different conformational selectivity for (+)METH-like compounds.

The haptens were conjugated to the terminal amino groups of lysines in bovine serum albumin or ovalbumin by carbodiimide chemistry, which forms a peptide bond with the available carboxylic acid on the hapten. There were 59 lysines in bovine serum albumin, 20 in each of the four subunits of ovalbumin and even more conjugation sites were available on cationized bovine serum albumin (i.e., lmject Supercarrier Immune Modulator). However not all of the lysines or conjugation sites were available at the surface of the protein for coupling to the haptens. Preliminary optimization experiments showed that a ratio of hapten to protein of 30:1 to 90:1 yielded the best incorporation rates for the syntheses. While the hapten incorporation rate for the antigens could not be precisely determined, initial mass spectrophotometry studies indicated that an average of 4 haptens were conjugated to each molecule of protein.

Because the primary goal was to select for high-affinity mAb, the antigen dose was kept relatively low (e.g., 10-20 µg). While immunization with higher hapten-antigen doses (e.g., 50-100 µg) sometimes led to higher titers, the affinity for (+)METH was often too low. Thus a minimum dose of antigen was typically used. This strategy routinely led to immunological response in only 40-70% of animals. In more recent studies, it was discovered that a primary reason for <100% immunological response was the low incorporation rate of the hapten on protein antigens, which in part was overcome by judicious use of Freund's complete and incomplete adjuvants to boost and sustain immunological response.

Each mouse serum from each group of immunizations was routinely screened (typically 6-10 mice) after each boost to determine the maturity of the immune response and the relative immunochemical characteristics of the polyclonal serum (titer, affinity and specificity). For this, a [$^3$H]-(+)METH RIA was used. The screening assay always involved inhibitions of [$^3$H](+)METH binding with increasing doses of (+)METH and (+)AMP to determine the relative affinities for each ligand. The final choice of a specific mouse for use in generating hybridomas was based primarily on the animal with the highest titer and affinity for (+)METH. From this process of screening immune serum, 3-10 unique monoclonal antibodies were generally found from each fusion. Most importantly, a polyclonal antiserum that was positive for (+)AMP was not discovered until the MO10 hapten was used.

For producing the hybridomas, mice were chosen that had been immunized with Freund's complete adjuvant and boosted with Freund's incomplete adjuvant. The one exception was the immunizations with (+)METH P6, which used Titermax as the adjuvant. In preliminary optimization experiments, immunizations with alum precipitated antigens, Titermax adjuvant and Ribi's adjuvant were tried on several occasions. While these adjuvants generally produced high titers, it was found that the highest affinity antibodies were generated with Freund's adjuvants.

Example 16

MAb Cross Reactivity Studies

After screening over 25,000 potential hybridoma cell lines for mAb production, five mAb with the most favorable immunochemical characteristics were extensively studied for molecular properties and preclinical efficacy (see Table 3). The rest of the hybridoma cell lines were stored frozen in case of future need. The selection of a mAb for more extensive in vitro and in vivo testing was based on the desire to have a range of affinities, a range of drug specificities, and a high level of mAb production from the parent hybridoma cell line. This final criterion was needed to increase the feasibility of large scale mAb production for in vivo testing. In most cases there was one or more similar affinity or specificity mAb that were produced from the same fusion. For instance, the separate fusions that produced mAb6H4 and mAb4G9 (see Table 3) also produced mAb with virtually the same affinity and specificity, but slightly different amino acid sequences. These two particular antibodies were chosen because the parent hybridoma cell line produced significantly more mAb.

TABLE 3

Chemical Structure of Haptens, the Resulting mAb, and $K_D$ Values for Key Drugs

| Hapten Structure | Hapten Name | mAb Name (Isotype and light chain) | (+)METH $K_D$ (nM) | (+)AMP $K_D$ (nM) | (+)MDMA $K_D$ (nM) |
|---|---|---|---|---|---|
| 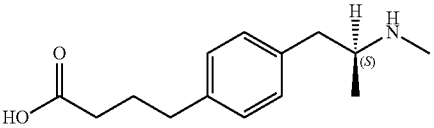 | (+)METH P4 | mAb6H8 (IgG$_1$ κ) | 250 | 41,000 | 106 |
| 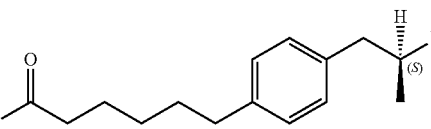 | (+)METH P6 | mAb6H4 (IgG$_1$ κ) | 11 | 4000 | 4 |
|  | (+)METH PO6 | mAb6H7 (IgG$_{2b}$ κ) | 95 | 47,000 | 87 |
|  | (+)METH MO6 | mAb9B11 (IgG$_1$ λ) | 41 | 5000 | 123 |
| 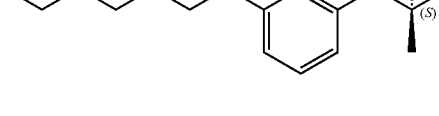 | (+)METH MO10 | mAb4G9 (IgG$_{2b}$ κ) | 34 | 140 | 140 |

Note: mAb4G9 (+)AMP value shown as 120 (51 nM with [$^3$H]–(+)AMP).

Results for Example 16

RIA was used to determine the relative affinity and cross-reactivity profile of each mAb (Tables 3 and 4). Only one of five haptens generated mAbs with the desired therapeutic potential. Immunization with the MO10 hapten resulted in production of mAb (mAb4G9) with high-affinity binding to (+)METH, (+)AMP, and (+)MDMA; little or no cross-reactivity with (−)METH-like isomers; and no significant cross-reactivity with endogenous compounds or structurally similar common medications (Tables 3 and 4). No other hapten/linker location yielded an antibody with high affinity for all three drugs of abuse.

TABLE 4

Characterization of the binding specificities of three important prototype anti-METH/MDMA or anti-METH/MDMA/AMP mAb.

| Drug | mAb6H4 (11 nM)[b] | mAb6H8 (250 nM)[b] | mAb4G9 (34 nM)[b] |
|---|---|---|---|
| (+)METH | 1.00 | 1.00 | 1.00 |
| (+)AMP | 0.001 | 0.023 | 0.34 |
| (+)MDMA | 1.25 | 3.40 | 0.29 |
| (−)METH | 0.030 | 0.011 | 0.102 |
| (−)AMP | <0.001 | 0.003 | 0.063 |
| (−)MDMA | 0.007 | 0.018 | 0.011 |
| (+)MDA | 0.001 | 0.024 | 0.090 |
| (−)MDA | <0.001 | <0.001 | 0.002 |
| 4-OH-METH | 0.588 | 0.294 | 0.106 |
| (+)pseudoephedrine | <0.001 | 0.018 | 0.004 |
| (+)norpseudoephedrine | <0.001 | <0.001 | <0.001 |
| /-phenylphrine | 0.001 | <0.001 | <0.001 |
| (+)ephedrine | <0.001 | <0.001 | <0.001 |
| (+)phenylpropanolamine | <0.001 | <0.001 | <0.001 |
| β-phenylethylamine | <0.001 | <0.001 | 0.001 |
| tyramine | <0.001 | <0.001 | <0.001 |
| dopamine | <0.001 | <0.001 | <0.001 |
| norepinepherine | <0.001 | <0.001 | <0.001 |
| serotonin | <0.001 | <0.001 | <0.001 |
| epinephrine | <0.001 | <0.001 | <0.001 |

[a] Relative potency to METH = (RIA IC50 value for METH/RIA IC50 value for test ligand). See Table 3 for the structures of the haptens used to generate these antibodies.
[b] IC50 value for METH binding from Table 3.

Since mAb4G9 was the only mAb to significantly cross-react with (+)AMP (Tables 3 and 4), its affinity for (+)AMP was examined in more detail. For this, a RIA analysis was conducted using [³H]-(+)AMP (in addition to a RIA with [³H]-(+)METH) and AMP as the inhibitor. These data showed that the actual affinity for AMP was 51 nM (Table 3), demonstrating that this mAb has virtually the same $K_D$ value for AMP and METH. [³H]-(+)MDMA was not available for determining a more accurate $K_D$ value for (+)MDMA binding, but it seems likely that the true $K_D$ value would be significantly lower than the value indicated by MDMA inhibition of [³H]-(+)METH binding in the RIA.

Attaching the linker of the hapten distal to the chiral center of the molecule yielded a refined specificity for (+)-isomers (Table 4). The relatively short length of spacer arms of haptens (+)METH P4 and (+)METH P6 (4- and 6-carbon linkers, respectively), coupled with attachments at the para-carbon of the (+)METH phenyl ring (Table 3), hindered the flexibility of haptens. This likely forced the immune system to recognize the presence of the methyl group on the nitrogen molecule of (+)METH and (+)MDMA and its absence in (+)AMP. Thus, mAb affinity was high for (+)METH and (+)MDMA, but low for (+)AMP. The hapten (+)METH PO6, like (+)METH P6, was designed with a linker attached to the para-carbon of the phenyl ring, but an oxygen was included to influence localized charge and solubility and mimic the presence of one of two oxygen atoms at the para and meta positions of the methylenedioxy group of (+)MDMA (Table 3). An oxygen attached to the phenyl ring structure was included in two other haptens, (+)METH MO6 and (+)METH MO10, but linkers were attached to the meta-carbon of the phenyl ring of (+)METH. This strategy was designed to present the oxygen of the (+)MDMA-like structure along the same spatial plane as the (+)METH molecule's chiral center. The longer (+)METH MO10 spacer was used to allow more flexibility in the hapten on the protein in hopes of discovering mAb(s) with broader recognition of (+)METH-like structures. These combined strategies resulted in the best balance of affinity and specificity.

From these studies, it was learned that 1) linkers located distal to the chiral center of this very small molecule favor generation of stereospecific antibodies, 2) a longer flexible linker arm like (+)METH MO10 favors generation of antibodies with broader selectivity for (+)METH-like compounds, and 3) spacers >6 atoms produce higher affinity mAbs. Importantly, discovery of mAb4G9 was not an isolated event, as other MO10-derived mAbs with similar specificities for (+)METH and (+)AMP have since been discovered.

Example 17

Antibody Sequence Analysis

To gain a better molecular understanding of how the primary amino acid sequence affected mAb affinity for (+)METH, related and unrelated sequence features in each mAb variable region was analyzed. Three of the mAb were IgG1 subclass and two were IgG2 (Table 3). Except for anti-METH/MDMA mAb9B11 (λ light chain), all of the mAb possessed a κ light chain.

cDNA Cloning and Sequencing of mAb for Example 17

For these studies, five prototype anti-METH mAb ranging in METH affinities from 11 to 250 nM were analyzed (Table 3). A single prototype mAb resulting from each of the haptens was chosen for detailed studies. The light chain (LC, singular and plural) cDNA of the mAb were cloned by RT-PCR using Superscript II reverse transcriptase (Invitrogen) with an exact reverse primer matching C-terminus of the light chain named MLEND1. Not (5'-GGG GCG GCC GCG CGT CTC AGG ACC TTT GTC TCT AAC-3') (SEQ ID NO:1). The light chains of mAb6H4, mAb6H8, and mAb6H7 were amplified in the forward direction with the degenerate primer ML2, and the light chain of mAb4G9 was amplified in the 5' direction with the degenerate primer ML4 (Coloma et al., 1992). The light chain of mAb9B11 was amplified in the forward direction with the primer sequence 5'-ATGGCCTGGA(T/C)TTCACTTATACTCTCTCTCCTGGCTCTC-3' (SEQ ID NO:2). The resulting cDNA was blunt-ligated into the Sma I site of the cloning vector pGEM-3Z.

The heavy chain cDNA of all IgG1 (from (+)METH P4, (+)METH P6 and (+)METH MO6) mAb were amplified using RT-PCR as described above with an exact reverse primer to the C-terminus of the heavy chain, named MHEND.NotI 5' GGG GCG GCC GCA GGG CTC CAA GGA CAC TGG GAT CAT TT 3' (SEQ ID NO:3), and a mixture of three degenerate primers based on the MHALT primers from Coloma et al. (1992, J Immunol Methods 152: 89-104). The primers were modified from the originally published sequence only by the substitution of a Nhe I restriction site for the original restriction site. The IgG2 mAb (from (+)METH PO6 and (+)METH MO10) were amplified with the reverse primer 5-CTCCCGGTCTCCGGGTAAATGA-3' (SEQ ID NO:4).

The forward sequence of the heavy chain of mAb6H8 was amplified with primer MHALT1 (Coloma et al., 1992, J Immunol Methods 152:89-104). The forward primers for mAb6H4, mAb6H7, mAb9B11, and mAb4G9 were designed from the results of N-terminal sequencing of the mature proteins (see FIGS. 27A and B for protein sequences). The primer sequences used were: 5'-GAGTGCAGCTTCAG-GAGTCAGGACCTAGC-3' (SEQ ID NO:5) for mAb6H4, 5'-GATGTAAAACTTCAGGAGTCAGGACCTG-GCCTCGTGAAACCTTCTCAGTC-3' (SEQ ID NO:6) for mAb6H7, 5'-GAGGTGCAGCTTCCGGAGTCAGGAC-CTAGC-3' (SEQ ID NO:7) for mAb9B11, and 5'-GAGTAC-CAGCTCCAGCAGTCTGGGAC-3' (SEQ ID NO:8) for mAb4G9. The cDNA was then blunt-ligated into the Sma I site of cloning vector pGEM-3Z. The resulting plasmids of all mAb cloning was transformed into *E. coli* strain DH5α and sequenced at University of Arkansas for Medical Sciences DNA Core Sequencing Facility.

All sequences were submitted to the GenBank database. The GenBank-assigned accession numbers of the light chains of mAb6H8, mAb6H4, mAb6H7, mAb9B11, and mAb4G9 are 774083, 786626, 877567, 881246, and 877579 respectively. The GenBank-assigned accession numbers of the heavy chains of mAb6H8, mAb6H4, mAb6H7, mAb9B11, and mAb4G9 are 774081, 774071, 881226, 877571, and 877573, respectively. The germ-line usage of the different mAb was determined by comparing the DNA sequences to those in the IMGT database using the web-based program V-QUEST tools (Internet address: http://imgt.cines.fr) and by visual examination of the sequences (Giudicelli et al., 2004, Nuc Acid Res 32:W435-440).

Results for Example 17.

Alignments of the amino acid sequences of the variable region of the mAb is presented in FIG. 27. An analysis of complementary determining regions revealed a high degree of diversity in both composition and length. The first light chain CDRs (L1) varied in length from 10-14 residues, and with the exception of mAb4G9, possessed a large number of serine residues (FIG. 27B). The only conserved residue in CDR L1, or any of the light chain CDRs, was the serine at position L26. The L2 CDRs were 7 residues in length except for mAb6H7, which possessed only 5 amino acids. The L3 CDRs were all 9 residues in length except mAb4G9 which had 10 residues. The CDRs of the heavy chain regions (FIG. 27A) exhibited similar lengths in CDRs H1 and H2, but little homology. CDR H1 had a conserved threonine at position H30 and either a tryptophan or tyrosine at position H33. CDRH3 differed in length from 8-16 residues. Although not immediately apparent from the alignment, all H3 regions possessed two tyrosine residues spaced five residues apart, with the second tyrosine before the tryptophan at H103.

While comparisons of CDR sequences are important, differences in CDR can be attributed to differences in germ-line sequences of particular V-region genes, and to somatic mutation within the CDRs of these V-region genes. To better understand the relative importance of the germ-line and somatic mutations, the sequenced genes were analyzed using the IMGT database (Giudicelli et al., 2004, Nuc Acid Res 32:W435-440). The analysis showed that each antibody was unique and not clonal. That is, rather than coming from one germ-line gene arrangement early in B cell development, they resulted from unique V(D)J recombination events. These unique germ-line gene rearrangements then underwent somatic DNA mutations, that were often silent, but some resulted in amino acid changes that differed from the original germ-line gene. Thus, no clear pattern of response was found.

This sequence analysis elucidated unique sequence differences in the antibody CDRs. A common feature was a conserved proline at position 95 or 95a of all CDR L3 regions, except for mAb9B11 (FIG. 27B), which had serine residue. Because of their ability to form "hinges," proline residues often lend flexibility in main chain protein sequences. This proline/serine was immediately followed by either a hydrophobic amino acid (i.e. leucine or valine as in mAb6H4 and mAb9B11, respectively) or an aromatic residue. It is possible that these residues could be important for interaction with the phenyl ring of (+)METH-like compounds via hydrophobic or pi-pi interactions, and the preceding proline could lend flexibility to adapt to different conformations.

Example 18

Molecular Modeling and Docking

Based on the results of the primary sequence alignment, three mAb (mAb6H4, mAb6H8 and mAb4G9) were chosen for structural modeling. Each CDR variable region was assigned and given a canonical classification (Al-Lazikani et al., 1997, J Mol Biol 273:927-948), except for the $H_3$CDRs, which do not possess canonical classes.

IgG Variable Region Structural Modeling and Analysis for Example 18

Molecular modeling of the three dimensional structure of the variable regions of three of the mAb was performed using the WAM antibody modeling algorithm (Whitelegg and Rees, 2000, Protein Eng 13:819-824). mAb6H4, mAb6H8, and mAb4G9 were chosen for more detailed analysis because they exhibited the full range of affinities for (+)METH and a broad range of ligand specificities for other important METH-like drugs. The primary amino acid sequences of the variable regions of the HC and LC were first submitted to the WAM antibody modeling site for alignment. The program aligned the sequences against known sequences in the database and searched for canonical classes of complementary determining regions (CDR). Based on these classifications, the program assigned a 3-dimensional structure to the framework and CDR regions by fitting the main chain to that of the closest known structures.

Ligand Docking for Example 18.

For docking simulation, the FlexX (Tripos) program was used. First, a deep pocket was identified at the interface of the CDR regions from surface modeling and electrostatic calculations in Pymol (Delano Scientific, San Carlos, Calif.) and Sybyl (Tripos). To define this region as a putative active site, residues within an area 6 Å around F L94 (for mAb6H4) or Y L94 (for mAb4G9) were selected. The METH ligand was assigned formal charges by Sybyl and the molecule was allowed partial flexibility. The program was set to find the 30 best docking conformations and return these in a consensus scoring table.

Results for Example 18.

Figure 28:
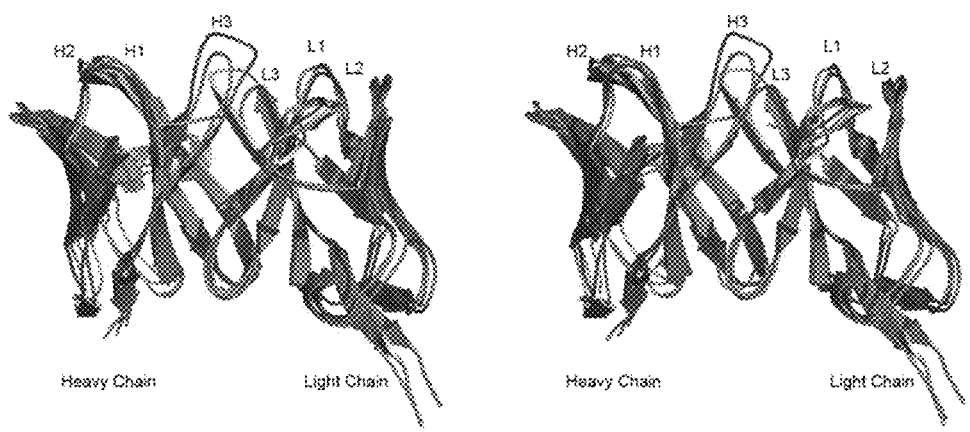
FIG. 28 presents molecular models of three anti-METH mAb. Upper panel: Stereo view of superimposed molecular models of anti-METH mAb. The variable regions of the three mAb were modeled, structurally aligned and represented in cartoon format. The framework residues are represented in blue. The CDR regions are colored according to mAb: mAb6H4, blue; mAb6H8, red; mAb4G9, green. The heavy chain, light chain, and CDR regions are labeled. Lower panel: RMSD (Å) of CDRs from the main chain conformation of mAb6H4.

The three-dimensional models exhibited classical antibody β-sheet fold conformation (FIG. 28). In general, all models showed conformity with geometrical constraints throughout the structures. The analysis indicated that less than 2% of residues had main chain ψ and φ angles in outlier regions. All three models appeared to conform reasonably well to known protein structural features and constraints, and they presented an appropriate foundation to conduct base docking analysis.

All CDRs fell within canonical classes except L3 of mAb4G9 and the $H_3$CDRs, which do not have canonical classes. The CDR H3 regions of all three antibodies were predicted to form a kinked or "hairpin," rather than extended conformation. Comparison of the models revealed conserved structural elements and some potentially important differences in the root mean square deviations (RMSD) of the CDR loop configurations (FIG. 29). The loop structure of mAb6H4 was arbitrarily chosen as a reference point to compare the differences from the other two antibodies, because it had the highest affinity for (+)METH. The L2 CDRs of all three antibodies occupied nearly the same spatial positions. The L3 regions of mAb6H4 and mAb6H8 were very similar, even though they differed in affinity for (+)METH by about 25-fold.

Based on the modeling results, docking simulation was performed with mAb6H4 and mAb4G9. According to the models (FIG. 29), a deep pocket was formed by the interaction of CDR loops H1, H2, L1 and L3 for both antibodies, with a wider pocket formed in the binding region of mAb4G9 due to a shorter $H_3$CDR. A theoretical docking of (+)METH was created into these mAb pockets and identified residues within 8 angstroms of the ligand as possible sites for ligand-mAb interaction (FIG. 29). The results of this FlexX-based docking indicated that the METH molecule was generally oriented with the hydrophobic phenyl group toward the interior of the pocket. In mAb6H4 and mAb4G9, the charged nitrogen of METH was in close proximity to a histidine at position L32 and H35 respectively.

Based on the molecular modeling analyses, the interface between (+)METH and the mAb was relatively small, (the surface area of (+)METH is 174 Å 2) with small shifts in protein conformation producing large changes in binding. As can be seen in FIG. 28, the most striking deviations appeared in the $H_3$CDR region, with over 6 Å and 7 Å RMSD in mAb6H8 and mAb4G9, respectively. The diversity in the positions of the CDR suggests that each of these antibodies exhibited a binding paradigm to (+)METH-like drugs that was somewhat independent of loop configuration. The surface rendering of the models exposed a deep pocket at the CDR interface of mAb6H4. This pocket appeared to be approximately the size of (+)METH and would likely accommodate docking of the ligand. By contrast, the potential binding pocket of mAb4G9 was wider and shallower. It is hypothesized that the longer linker arm of (+)METH MO10 combined with the changed dihedral angle of an oxygen at the meta position of the phenyl ring contributed to the formation of a larger pocket. Analysis indicated that only five of the six CDR loops, might be directly involved in binding of (+)METH-like drugs, with L2 showing little contact. The (+)METH docking simulation with FlexX indicated that the potential binding pockets were dominated by aromatic residues with some capable of making hydrogen bonds (i.e., histidine and tyrosine).

Example 19

Concurrent (+)METH Use and Immune Response

Immunization with (+)METH P6-KLH conjugate was examined in more detail to determine if active immunization would result in anti-(+)METH antibodies and if chronic (+)METH use would affect production of anti-(+)METH antibodies. These questions are important because generation of an antibody response is dependent on specific immune receptor recognition of (+)METH-conjugates, and patient use of (+)METH during immunization could block an immune response.

For these studies, male Sprague-Dawley rats were immunized with KLH (control group) or the (+)METH P6 hapten-KLH conjugate (see Table 3 for hapten structure). (+)METH P6-KLH animals were further divided into two immunized groups—one with no subsequent administration of (+)METH, the other repeatedly challenged with (+)METH (3 mg/kg ip; twice a week). Analysis of relative antibody affinities was accomplished in an ELISA by adding increasing concentrations of (+)METH to mouse immune serum in microtiter plate wells coated with a (+)METH P6-ovalbumin conjugate.

Figure 30:
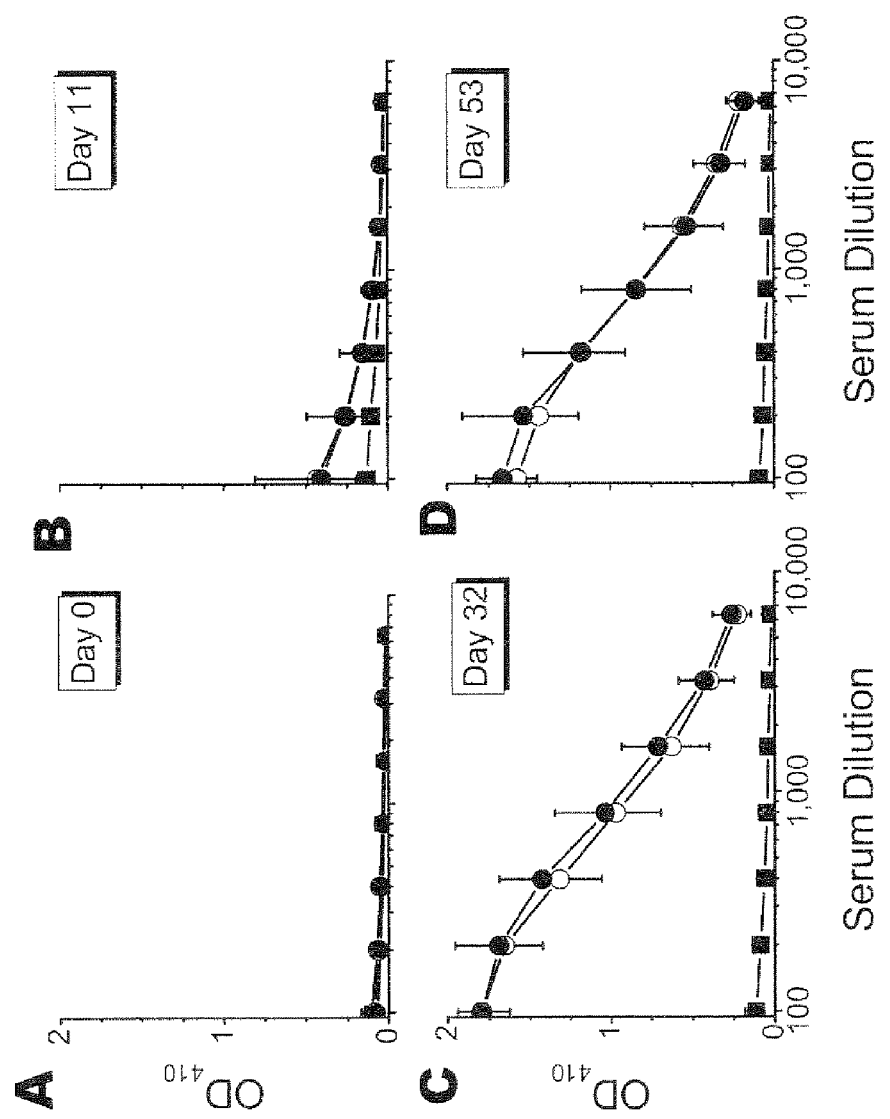
FIG. 30 illustrates immune responses to (+)METH P6 hapten-KLH conjugate. Comparison of rat anti-(+)METH antibody titers by ELISA. KLH immunized animals (■); (+)METH P6-KLH immunized animals (●); and (+)METH P6-KLH immunized animals with repeated 3 mg/kg, ip (+)METH challenges (○). (A) day 0 after immunization, (B) day 11 after immunization, (C) day 32 after immunization, (D) day 53 after immunization.
Figure 31:
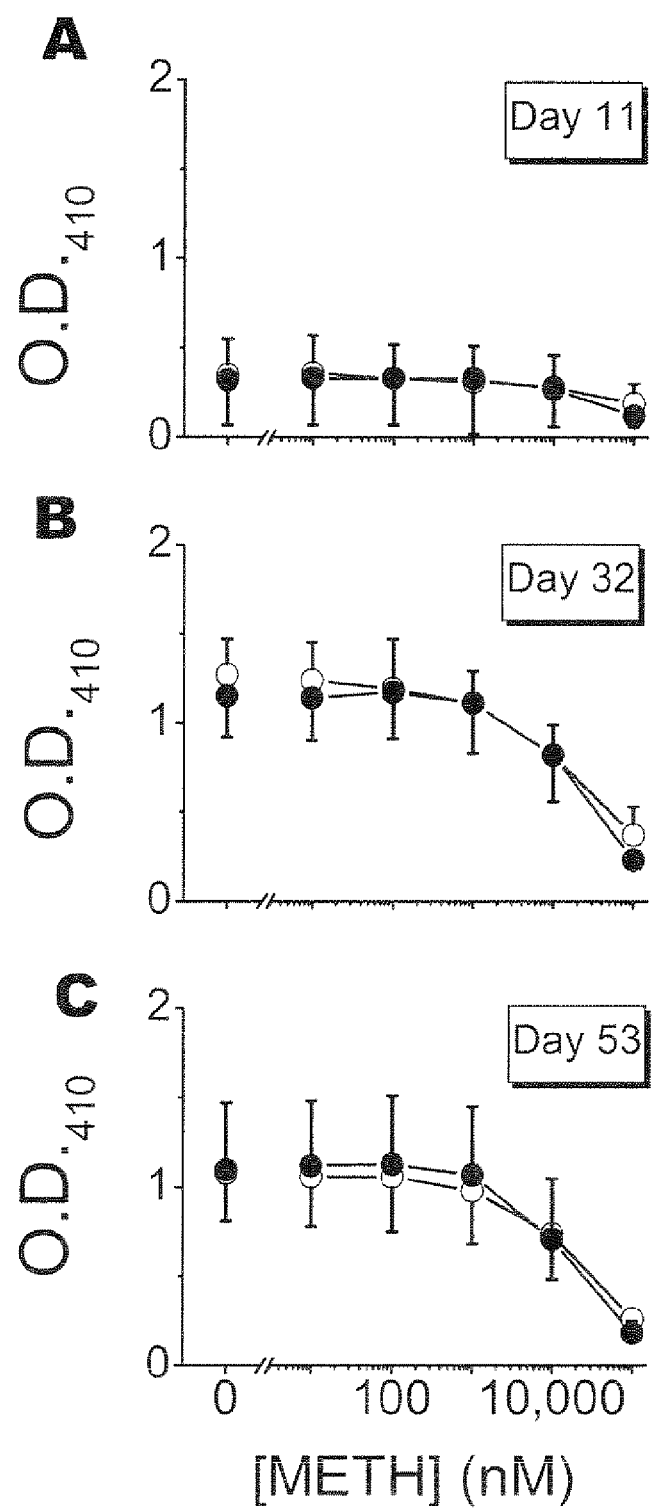
FIG. 31 presents rat serum antibody affinities for (+)METH as determined by ELISA. (+)METH P6-KLH immunized rats (●); (+)METH P6-KLH immunized rats with repeated (+)METH challenges (○). (A) day 11 after immunization, (B) day 32 after immunization, (C) day 53 after immunization.

By this measure, both groups of (+)METH P6-KLH immunized rats developed and maintained anti-(+)METH antibody titers throughout the 53-day immunization period (FIG. 30, open and closed circles) compared with control KLH-immunized rats, which had no response (squares). Repeated administration of (+)METH to immunized animals did not affect development or maintenance of anti-(+)METH titers (open circles), compared to immunized rats without a (+)METH challenge. In determining if there was a relative change in the serum antibody affinity for (+)METH in rats receiving repeated (+)METH administration, there was no difference in relative antibody affinity for (+)METH between non-challenged and (+)METH-challenged groups (FIG. 31).

Thus, challenging rats by repeated administration of (+)METH during the study did not affect antibody affinity constants for (+)METH or antibody serum titers. These studies demonstrate that chronic (+)METH use does not interfere with the quantity (titer) or quality (specificity, affinity) of the anti-(+)METH antibody response. These are important findings because many addicted patients will likely use (+)METH during their active immunization treatments.

Example 20

Anti-(+)METH mAb Alter (+)METH Pharmacokinetics in Rats

The ability of anti-(+)METH mAb6H4 (generated against (+)METH P6 hapten, see Table 3) to alter (+)METH brain concentrations was examined in two different models of (+)METH abuse (Byrnes-Blake et al., 2005, Eur J Pharmacol 521:86-94).

Figure 32:
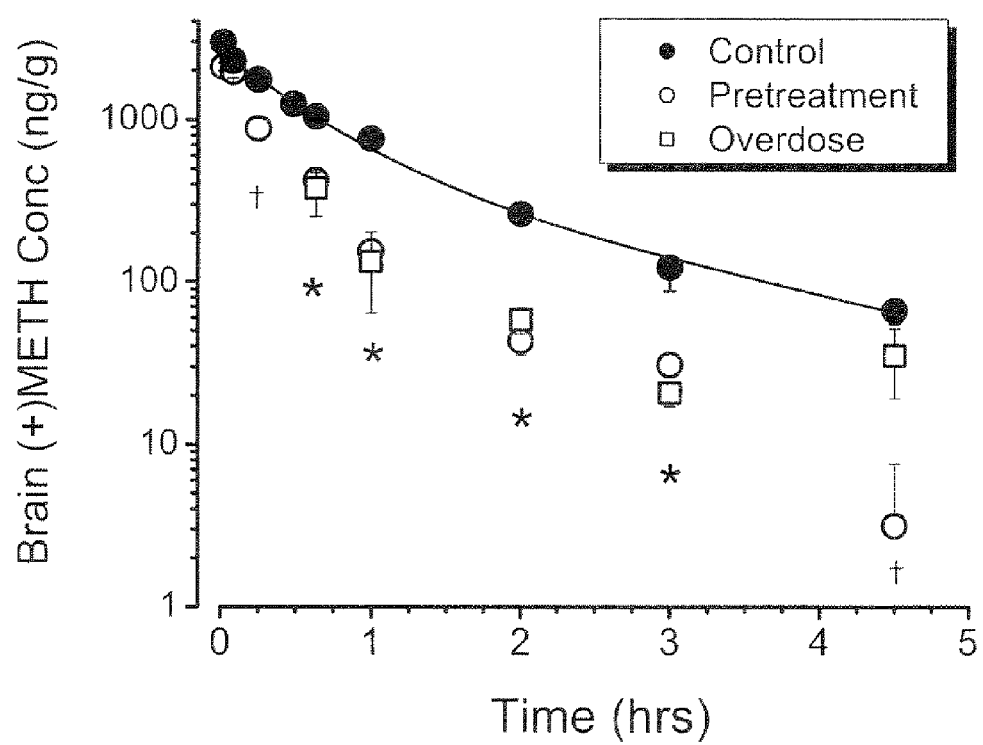
FIG. 32 illustrates clearance of brain (+)METH. Average concentration vs. time profiles for (+)METH in the brain without mAb6H4 (•), in an overdose (□), and in a pretreatment model (○). The * indicates that both the overdose and pretreatment points are statistically different from control ($P<0.05$). The † indicates that only the pretreatment time points are statistically different from the control ($P<0.05$).

The overdose model was designed to mimic a drug abuser taking a high iv (+)METH dose and treated with (+)METH mAb in the emergency room. In this model, rats received 1 mg/kg (+)METH (iv) followed 30 min later by an anti-(+)METH mAb dose. The mAb pretreatment model was designed to mimic an abuser in drug treatment administered an anti-(+)METH mAb medication at the start of behavioral modification therapy who relapses to (+)METH use. In this model, rats were pretreated with anti-(+)METH mAb6H4 and received a 1 mg/kg iv (+)METH dose the following day. This dose (without mAb) produced about 2.5 hrs of locomotor effects. Rats (3/time point) were sacrificed at varied times after (+)METH administration to determine (+)METH brain concentrations. As shown in FIG. 32, mAb6H4 decreased (+)METH brain concentrations in both models. Indeed, (+)METH brain concentrations in both models were virtually superimposable at comparable times after 30 min—the time of mAb administration in the overdose model. Both studies clearly show that antibodies against (+)METH can significantly reduce (+)METH brain concentrations over time.

Next, the "functional" half-life of each of the afore-mentioned anti-(+)METH mAbs (see Table 3) was determined. This "functional" assay compared (+)METH concentrations in the absence and presence of mAbs. By this measure, the best antibodies are those with the highest and longest increases in serum (+)METH and (+)AMP concentrations. First, it was determined that the pharmacokinetic properties of the mAbs were not different (results not shown). For instance, they all had a serum half-life of about 7-8 days, which ruled out the possibility that one or more of them were quickly cleared and thus inactivated through elimination. It also showed the potential to produce a long-acting anti-(+)METH therapy by passive or active immunization.

Figure 33:
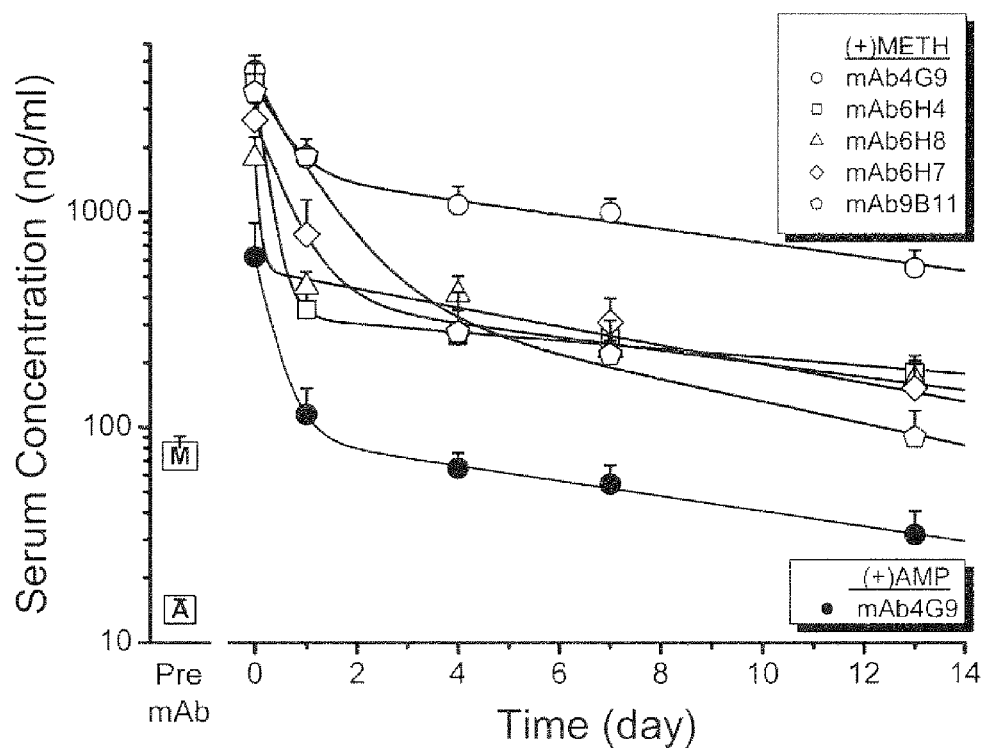
FIG. 33 presents serum concentration of (+)METH over time. (+)METH concentrations before (□ symbol with "M" inside) and after treatment (open symbols) with five different anti-(+)METH mAbs (n=3 rats/time point) and (+)AMP concentrations before (□ symbol with "A" inside) and after treatment (filled circles) with mAb4G9. (+)AMP concentrations (filled circles) are shown only for mAb4G9 because the other four mAbs did not produce long-term increases in (+)AMP concentrations. The best-fit line was determined using a weighted two-compartment pharmacokinetic model.

To conduct the "functional" studies, male rats (n=4/group) were given 14-day continuous (+)METH infusions at 5.6 mg/kg/day by sc osmotic minipumps. After achieving steady state (+)METH concentrations (at 24 hrs), each rat was treated with a dose of mAb that was equimolar in binding sites to the steady-state body burden of (+)METH. Only a single dose of mAb was administered at this time point, but (+)METH was continuously infused at a rate of 50% of the body burden per hour to maintain a (+)METH steady state. Serum samples were collected pre-mAb and at time points after mAb administration. All anti-(+)METH mAb caused significant acute increases in serum (+)METH concentrations compared with pre-mAb controls. However, there were substantial differences in serum (+)METH concentration vs. time curves for the five mAbs (FIG. 33, open symbols). Most anti-(+)METH mAbs appeared to be partially inactivated to differing degrees over time, as judged by their inability to maintain high concentrations of (+)METH in serum over time. This inactivation was particularly striking for the highest affinity mAb6H4 ($K_D$=11 nM). However, mAb4G9 ((+)METH and (+)AMP, $K_D$=34 and 51 nM, respectively) was still very effective after about 2 wks. It was also the only mAb that maintained significantly increased concentrations of (+)AMP (closed circles) and (+)METH (open circles) over time compared to pre-mAb concentrations (square symbols with "A" and "M" inside).

Example 21

Clearance in Brain and Serum

It was originally hypothesized that mAb affinity was the primary driving force for therapeutic efficacy. However, these studies revealed that the duration of action and function of the anti-(+)METH mAb in vivo was decreased based on predictions from known mAb pharmacokinetics, which was unanticipated. The first generation of haptens (e.g., (+)METH P6 and (+)METH P4) were purposely designed to produce mAbs specific for (+)METH, with virtually no cross reactivity with (+)AMP. When the second generation of haptens (e.g., (+)METH MO10) were produced with specificity for (+)METH and (+)AMP, it was discovered that the resulting mAb (mAb4G9) had the other advantages of increased duration of action and efficacy.

Figure 36:
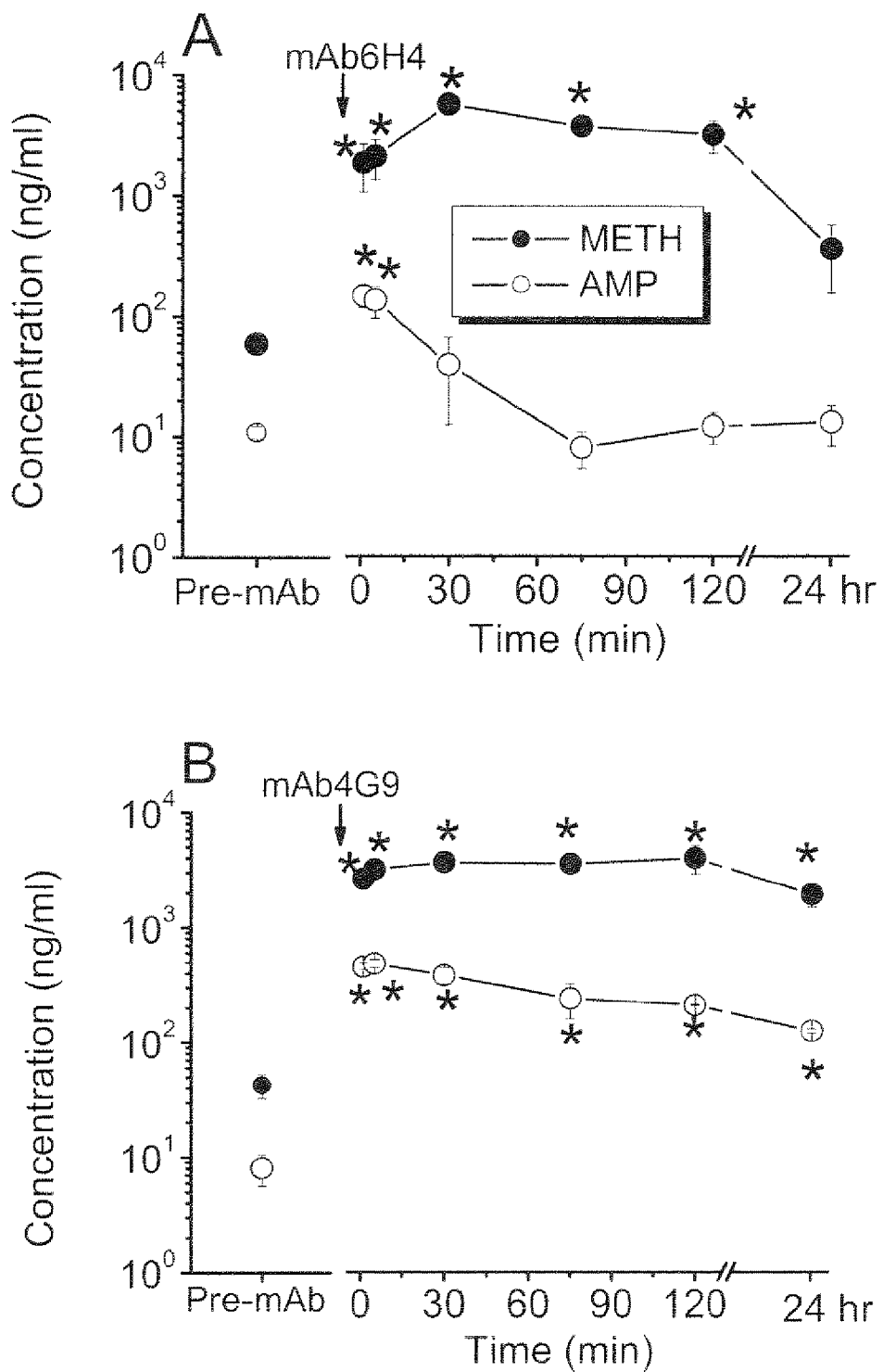
FIG. 36 depicts two graphs showing the effect of mAb6H4 (Panel A) and mAb4G9 (Panel B) on METH (closed circles) and AMP (open circles) concentrations in rat serum. METH was infused using a subcutaneous osmotic minipump and once steady state concentration were reached, anti-METH mAb was administered. Rats were sacrificed at various time points for determination of serum METH and AMP concentrations. mAb6H4 significantly increased METH serum concentrations at the 1, 5, 30, 75, and 120 min, but not at 24 hr, compared to the pre-mAb levels. AMP concentrations were increased briefly at the 1 and 5 min time points. MAb4G9 significantly increased METH and AMP serum concentrations at all time points.
Figure 37:
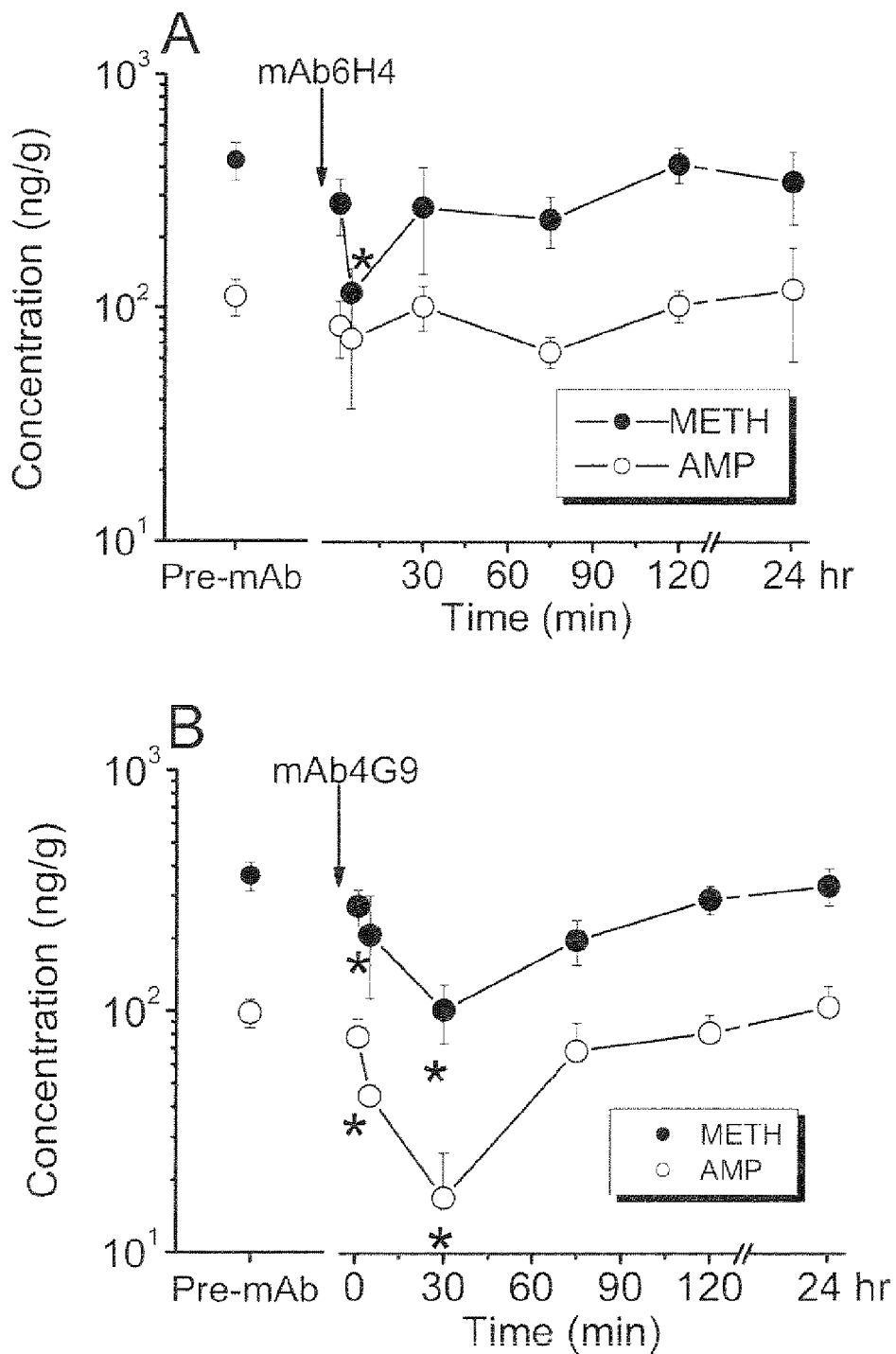
FIG. 37 depicts two graphs showing the effect of mAb6H4 (Panel A) and mAb4G9 (Panel B) on METH (closed circles) and AMP (open circles) concentrations in the rat brain. METH was infused using a subcutaneous osmotic minipump and once steady state concentrations were reached, anti-METH mAb was administered. Rats were sacrificed at various time points for determination of brain METH and AMP concentrations. METH brain concentrations were decreased only at the 5 min time point after mAb6H4 treatment, compared with pre-mAb levels. mAb6H4 had no effect on AMP brain concentrations. mAb4G9 significantly decreased METH and AMP serum concentrations at the 5 and 30 min time points, compared with pre-mAb levels; however, METH and AMP brain concentrations returned to pre-mAb levels by 75 min post-treatment.

For instance, see FIG. 37. mAb4G9, unlike mAb6H4 (generated by the P6 hapten), alters the distribution of AMP. As shown, mAb4G9 reduces both METH and AMP concentrations in the brain, which is medically important. It also repartitions AMP into the serum from other compartments (FIG. 36). mAb6H4 has little to no effect on AMP in either brain or serum because it is not broadly specific.

Furthermore, mAb4G9 has a longer functional half-life than mAb generated by previous haptens. FIG. 36 shows mAb6H4 has significantly less in vivo functionality (increased serum levels of METH/AMP is an indication of activity) by the 24 h timepoint. In contrast, mAb4G9 maintains significantly elevated serum METH and AMP concentrations 24 h after administration, indicating extended in vivo functionality.

The following, while not intending to be exhaustive, lists references cited herein:

Bazin-Redureau et al., J Pharm Pharmacol 49:277-281 (1997);
Byrnes-Blake et al., Int Immunopharmacol 1:329-338 (2001);
Cho et al., Synapse 39:161-166 (2001);
Collings, Cable News Network Feb. 13 (1996);
Cook et al., Drug Metab Dispos 21:717-723 (1993);
Davis and Preston, Anal Biochem 116:402-407 (1981);
Goding, Monoclonal Antibodies: Principles and Practice, p. 118-122, Academic Press, New York (1983);
Hardin et al., J Pharmacol Exp Ther 285:1113-1122 (1998);
Khor et al., Drug Metab Dispos 19:486-490 (1991);
Laurenzana et al., Drug Metab. Dispos. 23:271-278 (1995);
L1 and McMillan, Behav Pharmacol 12:621-628 (2001);
McMillan et al., Behav Pharmacol 12:195-208 (2001a);
McMillan et al., Pharmacol Biochem Behav 68:395-402 (2001b);
Minh-Tam et al., Anal. Biochem. 116:402-407 (1981);
Owens et al., J. Pharmacol. Exp. Ther. 246:472-478 (1988);
Proksch et al., J Pharmacol Exp Ther 292:831-837 (2000);
Rowland and Tozer, Clinical Pharmacokinetics: Concepts and Applications, 3rd ed, Williams & Wilkins, Baltimore (1995);
Riviere et al., J Pharmacol Exp Ther 291:1220-1226 (1999);
Riviere et al., J Pharmacol Exp Ther 292:1042-1047 (2000);
Tempest et al., Biotechnology 9:266-271, (1991);
Triplett et al., J Pharm Sci 74:1007-1009 (1985);
Valentine et al., J Pharmacol Exp Ther 278:709-716 (1996);
Valentine and Owens, J. Pharmacol. Exp. Ther. 278:717-724 (1996).

Any patents or publications mentioned in this specification are indicative of the levels of those skilled in the art to which the invention pertains. These patents and publications are herein incorporated by reference to the same extent as if each individual publication was specifically incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for generating a monoclonal antibody or an antigen binding fragment thereof, the method comprising generating the monoclonal antibody or the antigen binding fragment thereof using an immunogen comprising a hapten conjugated to an immunogenic carrier, wherein said hapten has the structure

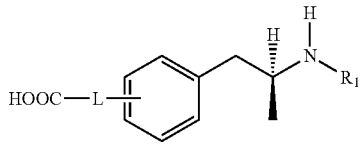

wherein said immunogenic carrier is conjugated to said hapten via the carboxylic group of the hapten, and wherein:

R1 is selected from the group consisting of hydrogen and methyl; and

L is selected from the group consisting of $\text{-}O(CH_2)_5$ attached to the benzene ring at the meta position, and $\text{-}O(CH_2)_9$ attached to the benzene ring at the meta position, wherein $\text{-}$ indicates point of attachment to the benzene ring.

2. The method of claim 1, wherein the immunogenic carrier is selected from the group consisting of KLH, ovalbumin, BSA, cationized BSA, thyroglobulin, a bacterial toxin and a bacterial toxoid.

3. The method of claim 1, wherein L is $\text{-}O(CH_2)_9$.

4. The method of claim 1, wherein L is $\text{-}O(CH_2)_5$.

5. The method of claim 1, wherein L is $\text{-}O(CH_2)_9$ attached to the benzene ring at the meta position and $R^1$ is methyl.

6. The method of claim 1, wherein L is $\text{-}O(CH_2)_5$ attached to the benzene ring at the meta position and $R^1$ is methyl.

* * * * *

SEQUENCE LISTING

```
<160> NUMBER OF SEQ ID NOS: 8

<210> SEQ ID NO 1
<211> LENGTH: 36
<212> TYPE: DNA
<213> ORGANISM: Artificial
<220> FEATURE:
<223> OTHER INFORMATION: MOUSE

<400> SEQUENCE: 1
ggggcggccg cgcgtctcag gacctttgtc tctaac                              36

<210> SEQ ID NO 2
<211> LENGTH: 40
<212> TYPE: DNA
<213> ORGANISM: Artificial
<220> FEATURE:
<223> OTHER INFORMATION: MOUSE

<400> SEQUENCE: 2
atggcctgga tcttcactta tactctctct cctggctctc                          40
```

```
<210> SEQ ID NO 3
<211> LENGTH: 38
<212> TYPE: DNA
<213> ORGANISM: Artificial
<220> FEATURE:
<223> OTHER INFORMATION: MOUSE

<400> SEQUENCE: 3
ggggcggccg cagggctcca aggacactgg gatcattt                          38

<210> SEQ ID NO 4
<211> LENGTH: 22
<212> TYPE: DNA
<213> ORGANISM: Artificial
<220> FEATURE:
<223> OTHER INFORMATION: MOUSE

<400> SEQUENCE: 4
ctcccggtct ccgggtaaat ga                                          22

<210> SEQ ID NO 5
<211> LENGTH: 29
<212> TYPE: DNA
<213> ORGANISM: Artificial
<220> FEATURE:
<223> OTHER INFORMATION: MOUSE

<400> SEQUENCE: 5
gagtgcagct tcaggagtca ggacctagc                                   29

<210> SEQ ID NO 6
<211> LENGTH: 50
<212> TYPE: DNA
<213> ORGANISM: Artificial
<220> FEATURE:
<223> OTHER INFORMATION: MOUSE

<400> SEQUENCE: 6
gatgtaaaac ttcaggagtc aggacctggc ctcgtgaaac cttctcagtc             50

<210> SEQ ID NO 7
<211> LENGTH: 30
<212> TYPE: DNA
<213> ORGANISM: Artificial
<220> FEATURE:
<223> OTHER INFORMATION: MOUSE

<400> SEQUENCE: 7
gaggtgcagc ttccggagtc aggacctagc                                  30

<210> SEQ ID NO 8
<211> LENGTH: 26
<212> TYPE: DNA
<213> ORGANISM: Artificial
<220> FEATURE:
<223> OTHER INFORMATION: MOUSE

<400> SEQUENCE: 8
gagtaccagc tccagcagtc tgggac                                      26
```